United States Patent
Breault et al.

[11] Patent Number: 5,811,459
[45] Date of Patent: Sep. 22, 1998

[54] ORTHO SUBSTITUTED AROMATIC COMPOUNDS USEFUL AS ANTAGONISTS OF THE PAIN ENHANCING EFFECTS OF E-TYPE PROSTAGLANDINS

[75] Inventors: Gloria Ann Breault, Congleton; John Oldfield, Wilmslow; Howard Tucker; Peter Warner, both of Macclesfield, all of United Kingdom

[73] Assignee: Zeneca Limited, London, United Kingdom

[21] Appl. No.: 647,977

[22] PCT Filed: Oct. 12, 1995

[86] PCT No.: PCT/GB95/02417

§ 371 Date: Jun. 4, 1996

§ 102(e) Date: Jun. 4, 1996

[87] PCT Pub. No.: WO96/11902

PCT Pub. Date: Apr. 25, 1996

[30] Foreign Application Priority Data

Oct. 12, 1994 [GB] United Kingdom ............... 9420557

[51] Int. Cl.⁶ .............. A61K 31/19; A61K 31/505; C07C 63/04; C07C 239/42

[52] U.S. Cl. ............ 514/555; 514/237.2; 514/262; 514/252; 514/340; 514/345; 514/568; 514/617; 544/174; 544/329; 544/332; 546/256; 546/268.4; 546/290; 546/298; 546/334; 548/338.1; 564/471; 564/472

[58] Field of Search ........................ 544/235, 236, 544/174, 329, 332; 549/50, 51, 52; 548/134, 136, 338.1; 546/256, 268.4, 290, 298, 334; 562/472; 564/52, 165, 171; 514/237.2, 252, 262, 340, 345, 555, 568, 617

[56] References Cited

U.S. PATENT DOCUMENTS

| | | | |
|---|---|---|---|
| 3,632,760 | 1/1972 | Shen et al. | 424/230 |
| 3,657,430 | 4/1972 | Shen et al. | 560/56 |
| 4,350,822 | 9/1982 | Albright et al. | 560/45 |
| 4,578,390 | 3/1986 | Jenson et al. | 514/456 |
| 4,937,373 | 6/1990 | Carson et al. | 560/56 |
| 5,087,743 | 2/1992 | Janssen et al. | 562/466 |
| 5,189,033 | 2/1993 | Tucker | 514/211 |
| 5,317,101 | 5/1994 | Oldfield et al. | 540/488 |
| 5,324,743 | 6/1994 | Dillard et al. | 514/456 |
| 5,409,930 | 4/1995 | Spada et al. | 514/248 |
| 5,420,270 | 5/1995 | Chandrakumar et al. | 540/488 |
| 5,441,950 | 8/1995 | Collins et al. | 514/211 |
| 5,480,883 | 1/1996 | Spada et al. | 514/249 |
| 5,530,157 | 6/1996 | Mewshaw et al. | 562/490 |
| 5,552,441 | 9/1996 | Dillard et al. | 514/569 |

FOREIGN PATENT DOCUMENTS

| | | |
|---|---|---|
| 2111035 | 6/1994 | Canada . |
| 0000816 | 2/1979 | European Pat. Off. . |
| 0122321 | 10/1984 | European Pat. Off. . |
| 0135087 | 3/1985 | European Pat. Off. . |
| 0193822 | 9/1986 | European Pat. Off. . |
| 0200101 | 12/1986 | European Pat. Off. . |
| 0218077 | 4/1987 | European Pat. Off. . |
| 372385 | 6/1990 | European Pat. Off. . |
| 0534667 | 3/1991 | European Pat. Off. . |
| 0475206 | 3/1992 | European Pat. Off. . |
| 0480641 | 4/1992 | European Pat. Off. . |
| 1560281 | 2/1980 | United Kingdom . |
| 1576007 | 10/1980 | United Kingdom . |
| WO 92/20642 | 11/1992 | WIPO . |
| WO 96/03380 | 2/1996 | WIPO . |
| WO 96/06822 | 3/1996 | WIPO . |
| WO 96/11902 | 4/1996 | WIPO . |

OTHER PUBLICATIONS

Derwent Patent Abstract of DE 2,701,854 (Abstract No. 52629Y/30).
Albright et al., J. Med. Chem. 1983, 26, 1378–1393.
Brown et al., J. Med. Chem. 1989, 32, 807–826.

*Primary Examiner*—Yogendra N. Gupta
*Attorney, Agent, or Firm*—Paul R. Darkes

[57] ABSTRACT

The invention relates to compounds of the formula (I):

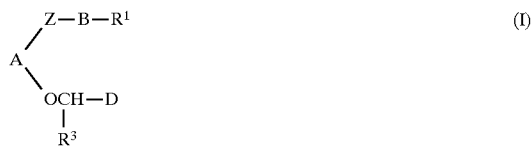

wherein A, B and D are various ring systems such as phenyl, $R^1$ includes carboxy, $R^3$ is hydrogen or $C_{1-4}$alkyl and Z is a linking group such as —$(CH(R^5))_m$— wherein m is 2, 3 or 4, and $R_5$ includes hydrogen and methyl; and pharmaceutically acceptable salts and in vivo hydrolysable esters or amides thereof, processes for preparing these compounds, pharmaceutical compositions comprising them, and their use in the treatment of pain.

11 Claims, No Drawings

ORTHO SUBSTITUTED AROMATIC COMPOUNDS USEFUL AS ANTAGONISTS OF THE PAIN ENHANCING EFFECTS OF E-TYPE PROSTAGLANDINS

This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

The compounds of the invention are useful in the treatment of pain such as the pain associated with joint conditions (such as rheumatoid arthritis and osteoarthritis), post-operative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly or in part play a pathophysiological role.

Non-steroidal anti-inflammatory drugs (NSAIDS) and opiates are the main classes of drugs in pain relief. However both possess undesireable side effects. NSAIDS are known to cause gastrointestinal irritation and opiates are known to be addictive.

We have now found a class of compounds structurally different to NSAIDS and opiates, and useful in the relief of pain.

The compounds of the invention may also possess anti-inflammatory, anti-pyretic and anti-diarrhoeal properties and be effective in other conditions in which prostaglandin $E_2$ ($PGE_2$) wholly or in part plays a pathophysiological role.

According to the invention there is provided a compound of the formula I;

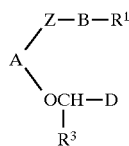
(I)

wherein:
A is optionally substituted: phenyl, naphthyl or a 5- or 6-membered heteroaryl ring system containing no more than two ring nitrogen atoms or thiadiazolyl or a bicyclic ring system of the formula:

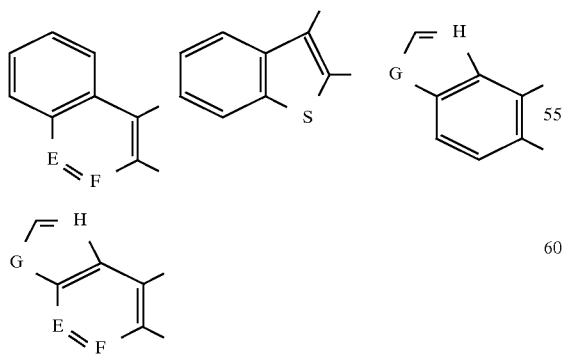

wherein E is nitrogen or CH, F is nitrogen or CH, G is sulphur or oxygen and H is nitrogen or CH;

wherein the —Z— and —OCH($R^3$)— groups are positioned in a 1,2 relationship to one another on ring carbon atoms; and provided that the ring atom in the 2-position relative to the ring carbon atom bearing the —OCH($R^3$)— group and in the 3-position relative to the ring carbon atom bearing the —Z—B—$R^1$ group is unsubstituted and, when A is naphthyl, either the —Z—B—$R^1$ group is in the 1-position and the —OCH($R^3$)— group is in the 2-position of the naphthyl group and the ring atom in the 3-position is not substituted, or the —Z—B—$R^1$— group is in the 2-position and the —OCH($R^3$)— group is in the 3-position of the naphthyl group and the ring atom in the 4-position is not substituted (according to the IUPAC system);

B is an optionally substituted 5- or 6-membered heteroaryl ring system, optionally substituted phenyl or an optionally substituted ring system of the formula:

(IA)

(IB)

(IC)

wherein 0 or 1 of J and K are ring nitrogen atoms and the remainder are ring carbon atoms and $R^4$ is $C_{1-6}$alkyl;
wherein the —Z—A and —R groups are positioned an either a 1,3 or a 1,4 relationship to one another on ring carbon atoms in B in 6 membered rings and in a 1,3 relationship to one another in ring carbon atoms in B in 5-membered rings;

D is optionally substituted: phenyl or a 5- or 6- membered heteroaryl ring system;

$R^1$ is carboxy, optionally substituted tetrazolyl, carboxy$C_{1-4}$alkyl, optionally substituted tetrazolyl$C_{1-4}$alkyl, hydroxamic acid, sulphonic acid, tetronic acid or a pharmaceutically acceptable amide (—CONR—), reverse amide (—NRCC—), acylsulphonamide (—CONRSO$_2$—), acylhydrazide (—CON(R)N ) or $C_{1-4}$alkyl substituted by a pharmaceutically-acceptable amide, reverse amide, acylsulphonamide or acylhydrazide or $R^1$ is of the formula (IIA), (IIB) or (IIC):

(IIA)

(IIB)

(IIC)

wherein X is CH or nitrogen, Y is oxygen or NH, Z is CH$_2$, NH or oxygen and $Y^1$ is oxygen or sulphur provided that there is no more than one ring oxygen and there are at least two ring heteroatoms;

$R^3$ is hydrogen or $C_{1-4}$alkyl;

Z is of the formula —$(CH(R^5))_m$—, —$(CHR^5)_p$ $CR^5=CR^5(CHR^5)_q$—, —$(CHR^5)_rC(=O)CR^5=CR^5(CHR^5)_s$— or —$(CHR^5_t)C(=O)(CHR^5)_u$—, wherein m is 2, 3 or 4, p and q are independently 0, 1 or 2 providing p+q is not greater than 2, one of r and s is 0 and the other is 1 and t and u are independently 0, 1, 2 or 3 providing t+u is not less than 1 or greater than 3;

and $R^5$ is hydrogen, methyl, ethyl, hydroxy, methoxy or ethoxy;

and N-oxides where chemically possible;

and S-oxides where chemically possible;

and pharmaceutically acceptable salts and in vivo hydrolysable esters and amides thereof.

Particular pharmaceutically acceptable amides are, for example, of the formula —$CONR^6R^7$ wherein $R^6$ is hydrogen, $C_{1-6}$alkyl, $C_{3-7}$cycloalkyl, $C_{3-7}$cyclcalkyl$C_{1-3}$alkyl, $C_{5-7}$cycloalkenyl or $C_{5-7}$cycloalkenyl$C_{1-3}$alkyl and $R^7$ is hydrogen, $C_{1-6}$alkoxycarbonyl, hydroxy or optionally substituted: $C_{1-10}$alkyl, $C_{1-10}$alkenyl, $C_{1-10}$alkynyl, $C_{3-7}$cycloalkyl, $C_{3-7}$cycloalkyl$C_{1-6}$alkyl, $C_{3-7}$cycloalkyl$C_{2-6}$ alkenyl, $C_{3-7}$cycloalkyl$C_{2-6}$alkynyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$alkyryl, 5- or 6-membered heteroaryl, 5- or 6-membered heteroaryl$C_{1-6}$alkyl, 5- or 6-membered saturated or partially saturated heterocyclyl, 5- or 6-membered saturated or partially saturated heterocyclyl$C_{1-6}$alkyl, 5- or 6-membered heteroarylium or 5- or 6-membered heteroarylium$C_{1-6}$alkyl; or wherein $R^6$ and $R^7$ together with the amide nitrogen to which they are attached ($NR^6R^7$) form an amino acid residue or ester thereof. Examples of 5- or 6-membered heteroarylium rings are pyridinium, pyriminidinium, pyrazinium, pyridazinium and imidazolium.

Particular pharmaceutically acceptable reverse amides are, for example, of the formula —$NR^6COR^8$ wherein $R^6$ is as hereinabove defined and $R^8$ is of the formula $OR^9$ wherein $R^9$ is hydrogen, optionally substituted $C_{1-6}$alkyl, 5- or 6-membered monocyclic heteroaryl or a 5- or 6-membered monocyclic saturated or partially saturated heterocyclyl, or $R^8$ is of formula $NR^{10}R^{11}$ wherein $R^{10}$ is hydrogen or $C_{1-6}$ alkyl and $R^{11}$ is optionally substituted $C_{1-6}$alkyl or $R^8$ is optionally substituted $C_{1-6}$alkyl; and wherein ring systems are optionally substituted.

Particular pharmaceutically acceptable acyl sulphonamides are, for example of the formula —$CONR^6SO_2R^{12}$ wherein $R^6$ is as hereinabove defined and $R^{12}$ is optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroylaryl$C_{1-6}$alkyl, phenyl, phenyl$C_{1-6}$alkyl, 5- or 6-membered saturated or partially saturated heterocyclyl, 5- or 6-membered saturated or partially saturated heterocyclyl$C_{1-6}$alkyl, 8-10 membered heteroaryl$C_{1-6}$alkyl or 5- or 6-membered heteroarylium$C_{1-4}$alkyl Particular acylhydrazides are, for example of the formula —$CONR_6N(R^{16})R^{17}$ wherein $R^6$ is as hereinabove defined, $R^{16}$ is hydrogen or $C_{1-6}$alkyl and $R^{17}$ is hydrogen, hydroxy or optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{5-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroaryl$C_{1-6}$alkyl, 5- or 6-membered saturated or partially saturated heterocyclyl, 5- or 6-membered saturated or partially saturated heterocyclyl$C_{1-6}$alkyl, or $R^{16}$ and $R^{17}$, together with the nitrogen atom to which they are attached, form a 4 to 8-membered saturated or partially saturated heterocyclic ring or form an amino acid residue or ester thereof.

A 5- or 6-membered heteroaryl ring system is a monocyclic aryl ring system having 5 or 6 ring atoms wherein 1, 2 or 3 ring atoms are selected from nitrogen, oxygen and sulphur.

A 5- or 6-membered saturated or partially saturated heterocyclyl is a ring system having 5 or 6 ring atoms wherein 1, 2 or 3 of the ring atoms are selected from nitrogen, oxygen and sulphur.

A 4 to 8-membered saturated or partially saturated heterocyclic ring is a ring system having 4 to 8 ring atoms wherein 1, 2 or 3 of the ring atoms are selected from nitrogen, oxygen and sulphur.

Particular 5- or 6-membered heteroaryl rings include pyrrolyl, imidazolyl, pyrazolyl, isothiazolyl, isoxazolyl, pyridyl, pyrazinyl, pyrimidinyl, pyridazinyl, thiazolyl, thiadiazolyl, thienyl, furyl and oxazolyl.

Particular 5- or 6-membered saturated or partially saturated heterocyclic ring ring systems include pyrrolidinyl, pyrrolinyl, imidazolidinyl, pyrazolidinyl, piperidyl, piperazinyl and morpholinyl.

An 8-10 bicyclic heteroaryl is a bicyclic aryl ring system having 8 to 10 ring atoms wherein 1, 2, 3 or 4 ring atoms are selected from nitrogen, oxygen and sulphur.

Examples of suitable optional substituents for $C_{1-6}$alkyl in amides, reverse amides, acylsulphonamides and acylhydrazides are hydroxy, amino, $C_{1-4}$alkoxy, halo, $C_{1-4}$alkoxycarbonyl, $C_{1-4}$alkylS(O)$_p$— (p is 0, 1 or 2), cyano, carboxy, $C_{1-4}$alkanoyl, $C_{1-4}$alkanoylamino, trifluoromethyl, pentafluoroethyl, nitro, $C_{3-7}$cycloalkyl, phenyl, 5- or 6-membered monocyclic heteroaryl, tetrazolyl, a 5- or 6-membered saturated or partially saturated heterocyclic ring and 5- or 6-membered monocyclic heteroarylium.

Particular substituents for ring systems in amides and reverse amides include, halo, trifluoromethyl, nitro, hydroxy, amino, cyano, $C_{1-4}$alkylS(O)$_p$— (p is 0, 1 or 2), carbamoyl, $C_{1-4}$alkanoylamino, $C_{1-4}$alkanesulphonamido and, when the ring system contains a saturated ring carbon (—$CH_2$—), oxo, hydroxyimino and $C_{1-4}$alkoxyimino.

Suitable ring systems of the formula (IIA), (IIB) or (IIC) include 5-oxo-4,5-dihydro-1,2,4-oxadiazole-3-yl, 3-oxo-2,3-dihydro-1,2,4- oxadiazole-5-yl, 3-thioxo-2,3-dihydro-1,2,4-oxadiazole-5-yl, 5-oxo-4,5-dihydro-1,3,4-oxadiazole-2-yl, 5-oxo-4,5-dihydro-1,2,4-triazole-3-yl, 3-oxo-2,3-dihydroisoxazole-5-yl, 5-oxo-1,5-dihydroisoxazole-3-yl and 5-oxo-2,3-dihydropyrazol-3-yl.

Amino acid residues formed from $R^6$ and $R^7$ or $R^{16}$ and $R^{17}$ together with the amide nitrogen to which they are attached and esters thereof include for example radicals of the formula —NH—CH($R^c$)—COO$R^d$ wherein $R^c$ is hydrogen, $C_{1-6}$alkyl, $C_{2-6}$alkenyl, $C_{2-6}$alkynyl, phenyl, phenyl$C_{1-3}$alkyl, 5- or 6-membered heteroaryl or 5- or 6-membered heteroaryl$C_{1-3}$alkyl and $R^d$ is hydrogen or $C_{1-6}$alkyl, wherein alkyl, alkenyl, alkynyl, phenyl and heteroaryl groups are optionally substituted. Examples of substituents include those mentioned above for ring A. In particular hydroxy.

Particular substituents for ring carbon atoms in A, include halo, trifluoromethyl, nitro, hydroxy, amino, $C_{1-4}$alkylamino, di[$C_{1-4}$alkyl]amino, cyano, $C_{1-6}$alkoxy, carboxy, allyloxy, $C_{1-6}$alkylS(O)$_p$— (p is 0, 1 or 2), phenylS (O)$_p$— (p is 0, 1 or 2), trifluoromethyl S(O)$_p$— (p is 0, 1 or 2) C$_{1-6}$alkyl (optionally substituted by hydroxy, C$_{1-4}$alkoxy, amino, halo, nitro, C$_{1-4}$alkylS(O)$_p$— (p is 0, 1 or 2), phenyl (O)$_p$— (p is 0, 1 or 2) or cyano), carbamoyl, C$_{1-4}$alkylcarbamoyl, di(C$_{1-4}$alkyl)carbamoyl, C$_{2-6}$alkenyl, C$_{2-6}$alkynyl, C$_{3-7}$cycloalkylC$_{1-3}$alkyl, C$_{3-7}$cycloalkylC$_{2-3}$alkenyl, C$_{5-7}$cycloalkenyl, C$_{5-7}$cycloalkenylC$_{2-3}$alkenyl, benzyl, benzoyl, benzyloxy, C$_{1-4}$alkoxycarbonylamino, C$_{1-4}$alkanoylamino, (wherein the alkanoyl group is optionally substituted by hydroxy), C$_{1-4}$alkanoyl(N—C$_{1-4}$alkyl)amino (wherein the alkanoyl group is optionally substituted by hydroxy), C$_{1-4}$alkanesulphonamido, benzenesulphonamido, aminosulphonyl, C$_{1-4}$alkylaminosulphonyl, di(C$_{1-4}$alkyl)aminosulphonyl, C$_{1-4}$alkoxycarbonyl, C$_{2-4}$alkanoyloxy, C$_{1-6}$alkanoyl, formylC$_{1-4}$alkyl, trifluoroC$_{1-3}$alkylsulphonyl, 1-(hydroxyimino)-1(phenyl)methyl, 1-(C$_{1-4}$alkoxyimino)-1-(phenyl)methyl, hydroxyiminoC$_{1-6}$alkyl, C$_{1-4}$alkoxyiminoC$_{1-6}$alkyl, C$_{1-6}$alkylcarbamoylamino, C$_{2-6}$alkenyl (substituted by halo), N-(amino)iminoC$_{1-4}$alkyl, N-(C$_{1-4}$alkylamino)iminoC$_{1-4}$alkyl, N-[di(C$_{1-4}$alkyl)amino]iminoC$_{1-4}$alkyl, N-(phenyl)aminoiminoC$_{1-4}$alkyl and 5-membered heteroaryl containing 1 or 2 heteroatoms selected from nitrogen, oxygen and sulphur and, when A is phenyl or a 6-membered heteroaryl ring having ring carbon atoms in the 4-position in relation to the —O—CH(R$^4$)— substitutent and in the 4-position in relation to the —Z—B—R$^1$ substitutent, suitable substituents include tetramethylene and diradicals of the formula —(CH$_2$)$_3$CO—, —(CH$_2$)$_3$C(=N—OH)— and —(CH$_2$)$_3$C(=N—OC$_{1-4}$alkyl)—, wherein the left hand side of the diradical is attached to the a carbon atom in the 4-position in relation to the —O—CH(R$^4$)— substitutent and the right hand side of the diradical is attached to a carbon atom in the 4-position in relation to the —Z—B—R$^1$ substitutent.

Particular substituents for ring carbon atoms in B include halo, trifluoromethyl, nitro, hydroxy, C$_{1-6}$alkoxy, C$_{1-6}$alkyl, amino, C$_{1-6}$alkylamino, di(C$_{1-4}$alkyl)amino, cyano, —S(O)$_p$C$_{1-6}$alkyl (p is 0, 1 or 2), C$_{1-4}$alkanoylamino, benzenesulphonamido, C$_{1-4}$alkanesulphonamido, C$_{1-6}$alkoxycarbonylamino, carbamoyl, C$_{1-4}$alkylcarbamoyl and di(C$_{1-4}$alkyl)carbamoyl.

Particular optional substituents for D are halo, trifluoromethyl, nitro, hydroxy, amino, C$_{1-4}$alkylamino, di(C$_{1-4}$alkyl)amino, C$_{1-4}$alkanoylamino, cyano, C$_{1-6}$alkoxy, allyloxy, —S(O)$_p$C$_{1-4}$alkyl (p is 0, 1 or 2), C$_{1-4}$alkanoyl or C$_{1-4}$alkyl optionally substituted by hydroxy, halo, nitro, cyano and amino.

Particular substituents for tetrazole groups include C$_{2-6}$alkanoyloxy and C$_{1-6}$alkyl.

Where a ring nitrogen atom in A, B or D can be substituted without becoming quaternised, it is unsubstituted or substituted by C$_{1-4}$alkyl.

The term alkyl when used herein includes straight chain and branched chain substituents for example methyl, ethyl, n-propyl, isopropyl, n-butyl and isobutyl. The same convention applies to other radicals, for example hydroxyiminoC$_{1-6}$alkyl includes 1-(hydroxyimino)ethyl and 2-(hydroxyimino)ethyl.

The invention also includes tautomers. For example 2-hydroxypyridine includes 2-pyridone.

Examples of C$_{1-6}$alkoxycarbonyl are methoxycarbonyl, ethoxycarbonyl and t-butoxycarbonyl; examples of carboxyC$_{1-3}$alkyl are carboxymethyl, 2-carboxyethyl, 1-carboxyethyl and 3-carboxypropyl; examples of C$_{1-6}$alkoxycarbonylC$_{1-3}$alkyl are methoxycarbonylmethyl, ethoxycarbonylmethyl and methoxycarbonylethyl; examples of tetrazolylC$_{1-3}$alkyl are tetrazolylmethyl and 2-tetrazolylethyl, examples of C$_{1-4}$alkoxy are methoxy, ethoxy, propoxy and isopropoxy; examples of C$_{2-6}$ alkenyl are vinyl and allyl; examples of C$_{2-6}$alkynyl are ethynyl and propynyl; examples of C$_{1-4}$alkanoyl are formyl, acetyl, propionyl and butyryl; examples of halo are fluoro, chloro, bromo and iodo; examples of C$_{1-4}$alkylamino are methylamino, ethylamino, propylamino and isopropylamino; examples of di(C$_{1-4}$)alkyl)amino are dimethylamino, diethylamino and ethylmethylamino; examples of —S(O)$_p$C$_{1-4}$alkyl are methylthio, methylsulphinyl and methylsulphonyl; examples of C$_{1-4}$alkylcarbamoyl are methylcarbamoyl and ethylcarbamoyl; examples of di(C$_{1-4}$alkyl)carbamoyl are dimethylcarbamoyl, diethylcarbamoyl and ethylmethylcarbamoyl; examples of C$_{1-6}$alkyl are methyl, ethyl, propyl and isopropyl; examples of C$_{3-7}$cycloalkyl are cyclopropyl, cyclobutyl and cyclohexyl; examples of C$_{3-7}$cycloalkylC$_{1-3}$alkyl are cyclopropylmethyl and cyclohexylmethyl; examples of C$_{3-7}$cycloalkylC$_{2-3}$alkenyl are cyclopropylethenyl and cyclopentylpropenyl; examples of C$_{3-7}$cycloalkylC$_{2-3}$alkynyl are cyclopropylethynyl and cyclopentylethynyl; examples of C$_{5-7}$alkenyl are cyclopentenyl and cyclohexenyl; examples of C$_{5-7}$cycloalkenylC$_{1-3}$alkyl are cyclopentenylmethyl and cyclohexenylmethyl; examples of C$_{5-7}$cycloalkenylC$_{2-3}$alkenyl are cyclohexenylethenyl and cycloheptenylethenyl; examples of C$_{5-7}$cycloalkenylC$_{2-3}$alkynyl are cyclopentenylethynyl and cyclohexenylethynyl; examples of C$_{1-4}$alkoxycarbonylamino are methoxycarbonylamino and ethoxycarbonylamino; examples of C$_{1-4}$alkanoylamino are acetamido and propionamido; examples of C$_{1-4}$alkanoyl(N—C$_{1-4}$alkyl)amino are N-methylacetamido and N-methylpropionamido; examples of C$_{1-4}$alkanesulphonamido are methanesulphonamido and ethanesulphonamido; examples of C$_{1-4}$alkylaminosulphonyl are methylaminosulphonyl and ethylaminosulphonyl; examples of di(C$_{1-4}$alkyl)aminosulphonyl are dimethylaminosulphonyl, diethylaminosulphonyl and ethylmethylaminosulphonyl; examples of C$_{1-4}$alkanoyloxy are acetyloxy and propionyloxy; examples of formylC$_{1-4}$alkyl are formylmethyl and 2-formylethyl; examples of hydroxyiminoC$_{1-6}$alkyl are hydroxyiminomethyl and 2-(hydroxyimino)ethyl; and examples of C$_{1-4}$alkoxyiminoC$_{1-6}$alkyl are methoxyiminomethyl, ethoxyiminomethyl and 2-(methoxyimino)ethyl.

Preferably A is optionally substituted:
phenyl, naphthyl, pyridyl, pyrimidyl, pyrazinyl, pyridazinyl, oxazolyl, thienyl, thiadiazolyl or thiazolyl.

Preferably ring systems of the formula (IA) are of the formula:

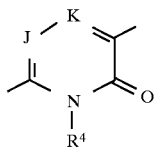

wherein J; K and R$^4$ are as hereinabove defined.

Preferably ring systems of the formula (IB) are of the formula:

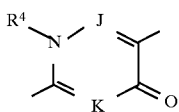

wherein J, K and $R^4$ are as hereinabove defined.

Preferably ring systems of the formula (IC) are of the formula:

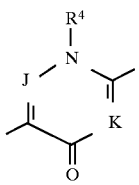

wherein J, K and $R^4$ are as hereinabove defined.

More preferably ring systems of the formula (IA) are N—$C_{1-4}$alkyl-2-oxo-1,2-dihydropyridin-3,6-diyl or 3-($C_{1-4}$alkyl)-4-oxo-3,4-dihydropyridin-2,5-diyl.

More preferably ring systems of the formula (IB) are N—$C_{1-4}$alkyl-4-oxo-1,4-dihydropyridin-2,5-diyl.

Preferably $R^4$ is methyl.

Preferably B is optionally substituted: phenyl, pyridyl, thiazolyl, thienyl, thiadiazolyl, imidazolyl, oxazolyl, pyrazinyl, pyridazinyl, pyrimidinyl, pyridone, pyridazinone, furan, pyrrole or pyrimidinone.

Preferably D is phenyl, thienyl, furyl, pyridyl, thiazolyl or oxazolyl.

More preferably A is optionally substituted: phenyl, thienyl naphthyl or thiadiazolyl.

Yet more preferably A is optionally substituted: phenyl, thienyl or naphthyl.

More preferably B is optionally substituted pyridyl, phenyl, thiazolyl, thienyl, pyrazinyl, oxazolyl, pyridazinyl or 2-pyridone optionally substituted on the ring nitrogen by a methyl group.

More preferably D is optionally substituted: phenyl, thienyl or furyl.

Preferably when D is phenyl it is unsubstituted or substituted in the meta- or para- position.

Most preferably A is optionally substituted phenyl.

Most preferably B is optionally substituted: phenyl, pyridyl, or 2-pyridone optionally substituted on the ring nitrogen by a methyl group.

Most preferably D is optionally substituted phenyl.

Preferably $R^1$ is optionally substituted tetrazolyl, carboxy$C_{1-4}$alkyl, optionally substituted tetrazolyl$C_{1-4}$alkyl, hydroxamid acid, sulphonic acid, tetronic acid or a pharmaceutically acceptable amide, reverse amide, acylsulphonamide or $C_{1-4}$alkyl substituted by a pharmaceutically-acceptable amide, reverse amide or acylsulphonamide.

Preferably pharmaceutically acceptable amides are, of the formula —$CONR^6R^7$ wherein $R^6$ is hydrogen or $C_{1-6}$alkyl and $R^7$ is hydrogen, $C_{1-6}$alkoxycarbonyl, hydroxy, optionally substituted $C_{1-6}$ alkyl, $C_{3-7}$cycloalkyl, phenyl, tetrazolyl, 5- or 6-membered heteroaryl, 5- or 6-membered monocylic saturated or partially saturated heterocyclyl and 5- or 6-membered heteroarylium, 5- or 6-membered monocyclic heteroaryl$C_{1-4}$alkyl, 5- or 6- membered saturated or partially saturated heterocyclyl$C_{1-4}$alkyl, 8–10 membered bicyclic heteroaryl$C_{1-4}$alkyl, 5- or 6-membered heteroarylium$C_{1-4}$alkyl or $C_{3-7}$cycloalkyl$C_{1-4}$alkyl, wherein ring systems are optionally substituted. Examples of 5- or 6-membered heteroarylium rings are pyridinium, pyriminidinium, pyrazinium, pyrazinium, and imidazolium.

Preferably pharmaceutically acceptable reverse amides are of the formula —$NR_6COR^8$ wherein $R^6$ is as hereinabove defined and $R^8$ is of the formula $OR^9$ wherein $R^9$ is hydrogen, optionally substituted $C_{1-6}$alkyl, 5- or 6-membered heteroaryl or a 5- or 6-membered saturated or partially saturated heterocyclyl, or $R^8$ is of formula $NR^{10}R^{11}$ wherein $R^{10}$ is hydrogen or $C_{1-6}$alkyl and $R^{11}$ is optionally substituted $C_{1-6}$alkyl or $R^8$ is optionally substituted $C_{1-6}$alkyl; and wherein ring systems are optionally substituted.

Preferably pharmaceutically acceptable acyl sulphonamides are of the formula —$CONR^6SO_2R^{12}$ wherein $R^6$ is as hereinabove defined and $R^{12}$ is optionally substituted: $C_{1-6}$ C alkyl, phenyl, 5- or 6-membered monocyclic heteroaryl, 5- or 6-membered monocyclic saturated or partially saturated heterocyclyl, 5- or 6-membered heteroaryl$C_{1-4}$alkyl, 5- or 6-membered saturated or partially saturated heterocyclyl$C_{1-4}$alkyl, 8–10 membered bicyclic heteroaryl$C_{1-4}$alkyl, 5- or 6-membered heteroarylium$C_{1-4}$alkyl or $C_{3-7}$cycloalkyl$C_{1-4}$alkyl.

More preferably $R^1$ is carboxy, optionally substituted tetrazolyl, carboxymethyl, optionally substituted tetrazolylmethyl, hydroxamic acid, sulphonic acid, tetronic acid or of the formula —$CONR^6R^7$ or of the formula —$CH_2CONR^6R^7$ wherein $R^6$ is hydrogen or $C_{1-4}$alkyl and $R^7$ is hydrogen, $C_{1-6}$alkoxycarbonyl, hydroxy, optionally substituted: $C_{1-6}$alkyl, cyclopropyl$C_{1-4}$alkyl, cyclobutyl$C_{1-4}$alkyl, cyclopenyl$C_{1-4}$alkyl, cyclohexyl$C_{1-4}$alkyl, pyridyl$C_{1-4}$alkyl, pyrimidyl$C_{1-4}$alkyl, pyrazinyl$C_{1-4}$alkyl, pyridazinyl$C_{1-4}$alkyl, tetrazolyl$C_{1-4}$alkyl, pyrrolidinyl$C_{1-4}$alkyl, morpholinyl$C_{1-4}$alkyl, imidazolium$C_{1-4}$alkyl, N-methylimidazolium$C_{1-4}$alkyl, pyridinium$C_{1-4}$alkyl, pyridyl, pyrimidyl, pyrazinyl, pyridazinyl, N-methylpyrimidinium, N-methylimidazolyl, pyridinium, pyrimidinium, tetrazolyl, phenyl, cyclopropyl, cyclobutyl, cyclopentyl, cyclohexyl or $R^1$ is of the formula —$NR^6COR^8$ or—$CH_2NR^6cor^8$ wherein $R^6$ is hereinabove defined and $R^8$ is hydroxy, pyridyloxy, pyrimidyloxy, pyrazinyloxy, pyridazinyloxy, optionally substituted $C_{1-6}$alkoxy, optionally substituted $C_{1-6}$alkylamino or optionally substituted $C_{1-6}$alkyl or $R^1$ is of the formula —$CONR^6SO_2R^{12}$ or —$CH_2CONR^6SO_2R^{12}$ wherein $R^6$ is as hereinabove defined and $R^{12}$ is $C_{1-6}$alkyl or phenyl, wherein alkyl groups and ring systems are optionally substituted.

Yet more preferably $R^1$ is carboxy, optionally substituted tetrazolyl, carboxymethyl, optionally substituted tetrazolylmethyl or of the formula —$CONR^6R^7$ or of the formula —$CH_2CONR^6R^7$ wherein $R^6$ is hydrogen or methyl and $R^7$ is hydrogen, $C_{1-6}$alkoxycarbonyl, hydroxy, $C_{1-6}$alkyl (optionally substituted by one or two substituents selected from hydroxy, amino, $C_{1-4}$alkoxy, halo, $C_{1-6}$alkoxycarbonyl, $C_{1-6}$alkylS(O)$_p$ (p is 0, 1 or 2), cyano, carboxy, $C_{1-4}$alkanoyl, $C_{1-4}$alkanoylamino, trifluoromethyl, pentafluoroethyl and nitro), cyclopropylmethyl, cyclobutylmethyl, cyclohexylmethyl, pyridylmethyl, pyrimidylmethyl, pyrazinylmethyl, pyrrolidinylmethyl, morpholinylmethyl, imidazoliumethyl or pyridiniummethyl, tetrazolylmethyl, pyridyl, N-methylpyrimidinyl, N-methylimidazolyl, tetrazolyl, phenyl (optionally substituted by hydroxy, nitro, halo, amino, methyl, ethyl, methoxy, ethoxy, cyano or trifluoromethyl), cyclopropyl, cyclobutyl, cyclohexyl or hydroxycyclohexyl, or $R^1$ is of the formula —$NR^6COR^8$ or —$CH_2NR^6CCR^8$ wherein $R^6$ is as hereinabove defined and $R^8$ is hydroxy, pyridyloxy, $C_{1-6}$alkoxy (wherein the alkyl group is optionally substituted by hydroxy, amino, halo, cyano, $C_{1-4}$alkoxy, trifluoromethyl, $C_{1-4}$alkylS(O)$_p$— (p is 0, 1 or 2), carboxy or $C_{1-4}$alkoxycarbonyl), $C_{1-6}$alkylamino (wherein the alkyl group is optionally substituted by hydroxy, amino, halo, cyano, $C_{1-4}$alkoxy, trifluoromethyl, $C_{1-4}$alkylS(O)$_p$— (p is 0, 1 or 2), carboxy, $C_{1-4}$alkoxycarbonyl or pyridyl) or $C_{1-4}$alkyl (optionally substituted by hydroxy, halo, carboxy, $C_{1-4}$alkoxycarbonyl, pyridyl or 2,4-dioxoimidazolidin-5-yl) or $R^1$ is of the formula —CONR$^6$SO$_2$R$^{12}$ or —CH$_2$CONR$^6$SO$_2$R$^{12}$ wherein $R^6$ is as hereinabove defined and $R^{12}$ is $C_{1-4}$alkyl or phenyl (wherein the alkyl and phenyl groups are optionally substituted by nitro, hydroxy, halo, amino, $C_{1-4}$alkyl, $C_{1-4}$alkoxy, cyano or trifluoromethyl).

Most preferably $R^1$ is carboxy, tetrazolyl, methanesulphonylaminocarbonyl, benzenesulphonylaminocarbonyl, (optionally substituted on the phenyl ring by nitro, hydroxy, halo, amino, $C_{1-4}$alkyl, $C_{1-4}$alkoxy, cyano ot trifluoromethyl), or $R^1$ is of the formula —CONR$^6$R$^7$ wherein $R^6$ is hydrogen or methyl and $R^7$ is propyl, 2-pyridylmethyl, 3-pyridylmethyl, 2-hydroxyethyl, tetrazolyl, tetrazolylmethyl, carboxymethyl, 1-carboxyethyl, 1-carboxypropyl or 1-carboxy-3-hydroxypropyl.

Preferred optional substituents for ring carbon atoms in A, are halo, nitro, trifluoromethyl, cyano, amino, $C_{1-6}$alkoxy, carbamoyl, $C_{1-4}$alkylcarbamoyl, di($C_{1-4}$alkyl)carbamoyl, $C_{1-4}$alkanoylamino, $C_{1-4}$alkanesulphonamido, benzenesulphonamido, $C_{1-4}$alkanoyl, $C_{1-4}$alkoxyimino$C_{1-4}$alkyl and hydroxyimino$C_{1-4}$alkyl, $C_{1-4}$alkylS(C p— or trifluoromethylS(O)p— (wherein p is 0, 1 or 2).

Preferably, when A is a 6-membered ring, it is unsubstituted or substituted in the 4-position relative to the —O—CH(R$^3$)— linking group.

Preferred optional substituents for ring carbon atoms in B are hydroxy, halo, methoxy, cyano, trifluoromethyl, amino, N-methylamino or N,N-dimethylamino.

Preferred optional substituents for D are halo, nitro, hydroxy, cyano, methyl, amino, methoxy or carbamoyl.

Preferably A is unsubstituted or substituted by one substituent.

Preferably B is unsubstituted or substituted by one substituent.

Preferably D is unsubstituted.

Preferably Z is —(CH$_2$)$_2$—, —(CH$_2$)$_3$—, —CH=CH—, —CH=CHCH$_2$—, —CH$_2$CH=CH— or —CH(Me)CH$_2$CH$_2$— wherein the left side of the linking group is attached to ring A and the right side to ring B.

Most preferably Z is —(CH$_2$)$_2$—, —(CH$_2$)— or —CH=CH—.

Preferably $R^3$ is hydrogen.

A preferred class of compounds is that of the formula (III):
wherein

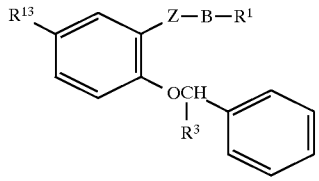

$R^1$, $R^3$, and Z are as hereinabove defined, $R^{13}$ is hydrogen, halo, trifluoromethyl, nitro, hydroxy, amino, $C_{1-4}$alkylamino, di[$C_{1-6}$alkyl]amino, cyano, $C_{1-6}$alkoxy, carboxy, allyloxy, S(O)$_p$$C_{1-6}$alkyl (p is 0, 1 or 2), S(O)$_p$— phenyl (p is 0, 1 or 2), $C_{1-6}$alkyl (optionally substituted by hydroxy, $C_{1-4}$alkoxy, amino, halo, nitro, S(O)$_p$$C_{1-4}$alkyl (p is 0, 1 or 2), S(O)$_p$-phenyl (p is 0, 1 or 2) or cyano), carbamoyl, $C_{1-4}$alkylcarbamoyl, di($C_{1-4}$alkyl)carbamoyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$ alkenyl, $C_{5-7}$cycloalkenyl, $C_{5-7}$cycloalkenyl$C_{2-3}$alkenyl, benzyl, benzoyl, benzyloxy, $C_{1-4}$alkoxycarbonylamino, $C_{1-4}$alkanoylamino, (wherein the alkanoyl group is optionally substituted by hydroxy), $C_{1-4}$alkanoyl(N—$C_{1-4}$alkyl)amino, wherein the alkanoyl group is optionally substituted by hydroxy), $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{2-4}$alkanoyloxy, $C_{1-6}$alkanoyl, formyl$C_{1-4}$alkyl, trifluoro$C_{1-3}$alkylsulphonyl, 1-(hydroxyimino)-1-(phenyl)methyl, 1-($C_{1-4}$alkoxyimino)-1-(phenyl)methyl, hydroxyimino$C_{1-6}$alkyl, $C_{1-4}$alkoxyimino$C_{1-6}$alkyl, $C_{1-6}$alkylcarbamoylamino, carboxy$C_{1-4}$alkoxy, $C_{2-6}$alkenyl (substituted by halo), N-(amino)imino$C_{1-4}$alkyl, N-($C_{1-4}$alkylamino)imino$C_{1-4}$alkyl, N-[di($C_{1-4}$alkyl)amino]imino$C_{1-4}$alkyl, N-(phenyl)aminoimino$C_{1-4}$alkyl, 5-membered heteroaryl containing 1 or 2 heteroatoms selected from nitrogen, oxygen and sulphur, tetramethylene, and diradicals of the formula —(CH$_2$)$_3$CO—, —(CH$_2$)$_3$C(=—OH)— and —(CH$_2$)$_3$C(=N—OC$_{1-4}$alkyl)— and B is phenyl or hydroxypyridyl.

Particular compounds of the present invention are:
4-[3-(2-benzyloxy-5-fluorophenyl)butyl]benzoic acid;
4-[3-(2-(4-methoxybenzyloxy)phenyl)propyl]benzoic acid;
N-(4-nitrobenzenesulphonyl)-4-[3-(2-benzyloxyphenyl)propyl]-benzenecarboxamide;
4-[3-(2-benzyloxy-5-fluorophenyl)propyl]benzoic acid;
5-[4-(2-benzyloxyphenethyl)phenyl]tetrazole;
4-2-benzyloxyphenethyl)-3-fluorobenzoic acid;
5-(4-(2-(2-benzyloxyphenyl)ethenyl)phenyl]tetrazole;
4-[3-(2-benzyloxy-5-chlorophenyl)propyl]benzoic acid;
4-[3-(2-(3-chlorobenzyloxy)phenyl)propyl]benzoic acid;
4-[3-(2-benzyloxynaphth-1-yl)propyl]benzoic acid;
4-[3-(2-benzyloxy-5-acetylphenyl)propyl]benzoic acid;
4-[3-(2-benzyloxy-5-nitrophenyl)propyl]benzoic acid;
4-[2-benzyloxy-5-chlorophenethyl]benzoic acid;
5-[4-(5-acetyl-2-benzyloxyphenethyl)phenyl]tetrazole;
5-[4-(2-benzyloxy-5-bromophenethyl)phenyl]tetrazole;
5-[6-(2-benzyloxy-5-bromophenethyl)-1-methyl-1,2-dihydro-2-oxopyridin-3-yl]tetrazole;
4-[3-(2-benzyloxy-5-(1-hydroxyiminoethyl)phenyl)propyl]benzoic acid;
4-[2-benzyloxyphenethyl]-2-hydroxybenzoic acid;
4-[3-(2-benzyloxyphenyl)propyl]-2-hydroxybenzoic acid;
4-[3-(2-benzyloxy-5-methylthiophenyl)propyl]benzoic acid;
2-[2-benzyloxy-5-bromophenethyl]-3,4-dihydro-3-ethyl-4-oxopyrimidin-5-carboxylic acid;
4-[2-(2-benzyloxyphenyl]ethenyl]-3-bromobenzoic acid;
4-[2-(2-benzyloxyphenyl)ethenyl]-3-methoxybenzoic acid;
4-[3-(2-benzyloxy-5-(2-methylpropionyl)phenyl)propyl]benzoic acid;
5-[4-(2-benzyloxy-5-chlorophenethyl)phenyl]tetrazole;
4-(2-benzyloxy-5-bromophenethyl)-2-hydroxybenzoic acid;
4-(2-benzyloxyphenethyl)-3-bromobenzoic acid;
4-[3-(2-benzyloxy-5-(1-(phenyl)hydroxyiminomethyl)phenyl)propyl]-benzoic acid;
4-(2-benzyloxy-5-bromophenylethyl)-2-methoxybenzoic acid;
4-[3-(2-benzyloxy-5-fluorophenyl)propyl]benzoic acid;
N-benzenesulphenyl-4-[3-(2-benzyloxy-5-chlorophenyl)propyl]-benzenecarboxamide;
4-[3-(2-benzyloxy-5-(1-(2-phenylhydrazino)ethyl)phenyl)propyl]benzoic acid;

4-[2-(2-benzyloxy-5-methylthiophenyl)ethenyl]-2-hydroxybenzoic acid;

5-[4-(2-benzyloxyphenethyl)-3-methoxyphenyl]tetrazole;

4-[3-(2-benzyloxyphenyl)propyl]-3-bromobenzoic acid;

5-[4-(2-benzyloxyphenethyl)-3-bromophenyl]tetrazole;

4-[3-(2-benzyloxyphenyl)propyl]-3-cyanobenzoic acid;

5-[4-(3-(2-benzyloxyphenyl)propyl)-3-bromophenyl]tetrazole;

4-(2-benzyloxy-5-methylthiophenethyl)-2-hydroxybenzoic acid;

5-[4-(3-(2-benzyloxyphenyl)propyl)-3-methoxyphenyl]tetrazole;

4-[2-benzyloxy-5-chlorophenethyl)-3-methoxy benzoic acid;

5-[4-(2-benzyloxy-5-chlorophenethyl)-3-methoxyphenyl]tetrazole;

4-(2-benzyloxy-5-methoxyphenethyl)-2-hydroxybenzoic acid; or 4-(2-benzyloxy-5-methylphenethyl)-2-hydroxybenzoic acid; or a pharmaceutically acceptable salt thereof It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses anti-hyperalgesic properties. The synthesis of optically active forms ray be carried out by standard techniques of organic chemistry well known in the art, for example by synthesis from optically active starting materials or by resolution of a racemic form. Similarly, the pain relieving effects may be evaluated using the standard laboratory techniques referred to hereinafter.

An in vivo hydrolysable ester or amide of a compound of the formula (I) containing carboxy group is, for example, a pharmaceutically acceptable ester or amide which is hydrolysed in the human or animal body to produce the parent acid, for example, a pharmaceutically acceptable ester or amide formed with a (1-6C)alcohol such as methanol, ethanol, ethylene glycol, propranol or butanol, or with a phenol or benzyl alcohol such as phenol or benzyl alcohol or a substituted phenol or benzyl alcohol wherein the substituent is, for example, a halo (such as fluoro or chloro), (1-4C)alkyl (such as methyl) or (1-4C)alkoxy (such as methoxy) group.

A suitable pharmaceutically-acceptable salt of a compound of the invention is, for example, an acid-addition salt of a compound of the invention which is sufficiently basic, for example an acid addition salt with an inorganic or organic acid such as hydrochloric, hydrobromic, sulphuric, trifluoroacetic, citric or maleic acid; or, for example a salt of a tricyclic heterocycle of the invention which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

In a further aspect the invention provides a process for preparing compounds of the formula (I) or pharmaceutically acceptable salts or in vivo hydrolysable amides or ester thereof, which comprises deprotecting a compound of the formula (VI):

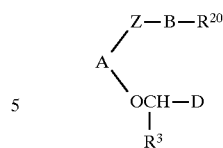

VI wherein $R^{20}$ is $R^1$ or protected $R^1$, $R^3$, Z, n, A, B and D are as hereinabove defined, and any optional substituents are optionally protected and at least one protecting group is present; and thereafter if necessary:

i) forming a pharmaceutically acceptable salt;

ii) forming an in vivo hydrolysable ester or amide;

iii) converting one optional substituent into another optional substituent.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1-4C)alkylsilyl group (especially trimethylsilyl or tert-butyldimethylsilyl), an aryldi-(1-4C)alkylsilyl group (especially dimethylphenylsilyl), a diaryl-(1-4C)alkylsilyl group (especially tert-butyldiphenylsilyl), a (1-4C)alkyl group (especially methyl), a (2-4C)alkenyl group (especially allyl), a (1-4C)alkoxymethyl group (especially methoxymethyl) or a tetrahydropyranyl group (especially tetrahydroyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2-4C) alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2-4C)alkanoyl group (especially acetyl), a (1-4C) alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group.

Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1-4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

In another aspect the compounds of the formula (I) or (VI) may be prepared:

a) converting $R^{22}$ to $R^{20}$ in a compound of the formula (VII):

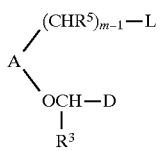
(VII)

wherein A, B, D, $R^3$, Z, and n are as hereinabove defined and $R^{22}$ is a precursor of $R^{20}$;

b) when Z is $-(CH(R^5))_m-$ by reducing a compound of the formula (VIII):

(VIII)

wherein A, B, D, $R^3$, $R^5$, $R^{20}$, n, p and a are as hereinabove defined;

c) when Z is $-(CHR^5)_t C(=O)(CHR^5)_u-$ or $(CH(R^5))_m-$ and m is 3 or 4, by reducing a compound of the formula (IX):

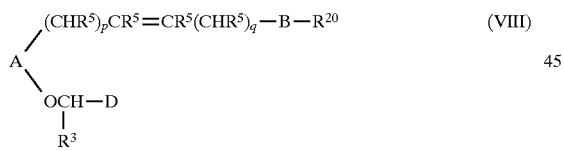
(IX)

wherein A, B, D, $R^3$, $R^5$, $R^{20}$, and n are as hereinabove defined and one of r and s is 0 and the other is 1;

d) when B is an activated heterocycle and Z is $-(CH(R^5))_m-$, by reacting a compound of the formula (X) with a compound of the formula (XI):

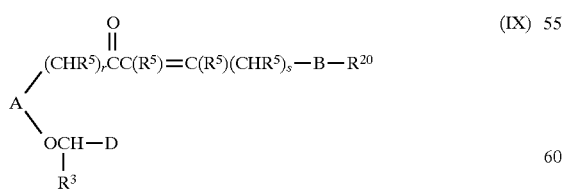
(X)

$R^5CH_2-B-R^{20}$ (XI)

wherein A, B, D, $R^3$, $R^5$, $R^{20}$, n and m are as hereinabove defined and L is a leaving group;

e) when Z is $-(CHR^5)_p CR^5=CR^5(CHR^5)_q-$, by reacting a compound of the formula (XII) with a compound of the formula (XIII):

(XII)

$R^{20}-B-(CHR^5)_{q-1}=PR^{23}R^{24}R^{25}$ (XIII)

wherein A, B, D, $R^3$, $R^5$, $R^{20}$, p, q and n are as hereinabove defined and $R^{23}$-$R^{25}$ are independently $C_{1-6}$alkyl or optionally substituted phenyl;

f) when Z is $-(CHR^5)_t CH=CH(CHR^5)$ and t is 0 or 1, by dehydrating a compound of the formula (XIV):

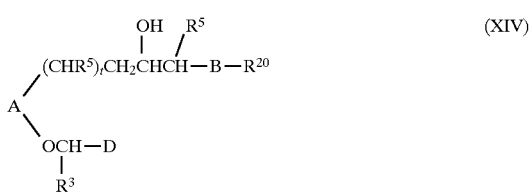
(XIV)

wherein A, B, D, $R^3$, $R^5$, $R^{20}$, and n are as hereinabove defined, and t is 0 or 1; or g) by reacting a compound of the formula (XV) with a compound of the formula (XVI):

(XV)

$L^1-CH-D$ (XVI)
|
$R^3$ wherein A, B, D, Z, $R^3$, $R^{20}$, and n are as hereinabove defined and $L^1$ is a leaving group; or h) by reacting a compound of the formula (XVII) with a compound of the formula (XVIII):

(XVII)

(XVIII)

wherein A, B, D, $R^3$, $R^5$, $R^{20}$, n, r and s are as hereinabove defined; and thereater if necessary:

i) removing any protecting groups;
ii) forming a pharmaceutically acceptable salt;
iii) forming an in vivo hydrolysable ester or amide;
iv) converting an optional substituent into another optional substituent.

Particular values for $R^{22}$ include cyano, carbamoyl, alkoxycarbonyl, carboxy and activated carboxy groups such as acid chlorides and activated esters.

The cyano group may be converted into a tetrazole ring by reacting, for example, with ammonium or tin azide in an aprotic solvent such as DMF, in a temperature range of 100° C. to 130° C. For further information on tetrazole synthesis see S. J. Wittenberger and B. J. Donner JOC, 1993, 58, 4139–4141; B E Huff et al, Tet. Lett, 1993, 50, 8011–8014; and J. V. Duncia et al, JOC 1991, 56, 2395–2400.

Alkoxycarbonyl may be converted into a carboxy group by acid or base hydrolysis. For example, base hydrolysis may be carried out in an organic solvent such as methanol or THF in a temperature range of ambient to 100° C., in the presence of sodium hydroxide or potassium hydroxide.

Acid hydrolysis may, for example, be carried out or in neat formic acid or neat trifluoroacetic acid optionally in an organic solvent such as dichloromethane.

An alkoxycarbonyl or an activated carboxy group, such as an acid chloride or activated ester, or an acyl group such as an alkanoyl group may be converted to an amide group by reacting with the appropriate amine in an inert solvent such as DMF or dichloromethane, in a temperature range of 0° C. to 150° C., preferably around ambient temperature, in the presence of a base such as triethylamine.

The compounds of the formula (VII) may be prepared using processes b), c), d), e), f) or g) from the appropriate starting materials wherein $R^7$ is replaced with $R^{10}$.

The compounds of the formula (VIII) may be reduced under standard conditions known in the art for the reduction of olefins, for example, catalytic hydrogenation using Raney nickel, platinum metal or its oxide, rhodium, zinc oxide, palladium-on-charcoal or Wilkinson's catalyst [RhCl(Ph$_3$P)$_3$] as the catalyst.

Catalyst hydrogenation is conveniently carried out in the temperature range 0° C. to 150° C., but preferably at ambient temperature at slightly above atmospheric pressure, unless the double bond is highly substituted in which case higher temperatures and pressure may be required, or Wilkinson's catalyst in which case a temperature of approximately 50° C. and pressure of approximately 50 atmospheres are preferable.

Compounds of the formula (VIII) can be prepared using process e) or process f) above.

Compounds of the formula (IX) are reduced by standard methods known in the art for the reduction of α,β-unsaturated ketones, without affecting ring B. For example, the double bond may be hydrogenated catalytically using Wilkinson's catalyst and then the ketone group reduced, if appropriate, by forming the tosyl hydrazone and reducing with sodium borohydride.

The compounds of the formula (IX) are conveniently prepared by reacting a compound of the formula (XVII) with a compound of the formula (XVIII). Suitable reaction conditions are described below.

The reaction between the compounds of the formulae (X) and (XI) is conveniently performed under standard conditions known in the art. Suitable leaving groups include halo, for example, chloro, bromo or iodo, and tosylate and mesylate.

In general the reaction is performed in an inert solvent such as hexane, tetrahydrofuran or ethyl ether, in a temperature range of −100° C. to ambient temperature, in the presence of a strong base such as butyl lithium, sec-butyl lithium, tert-butyl lithium, lithium diisopropylamide (LDA) or lithium hexamethyldisilylamide, preferably in the presence of a hindered base such as LDA or lithium hexamethyl disilylamide. For example wherein the leaving group is bromo, in tetrahydrofuran in the presence of LDA at 30° C.

The compounds of the formula (X) are conveniently prepared by reacting a compound of the formula (XVI) with a compound of the formula (XX):

wherein A and $R^5$ are as hereinabove defined and P is a hydroxy protecting group, and thereafter deprotecting the hydroxy group and converting it to a leaving group (L). Conversion of the hydroxy group to a leaving group is performed by standard processes known in the art.

For example when the leaving group is bromo, reacting the hydroxy group with phosphorous tribromide.

The reaction between compounds of the formulae (XVI) and (XX) are conveniently carried out under standard conditions known in the art for such ether-forming reactions, for example as described for the reaction between compounds of the formulae (XV) and (XVI).

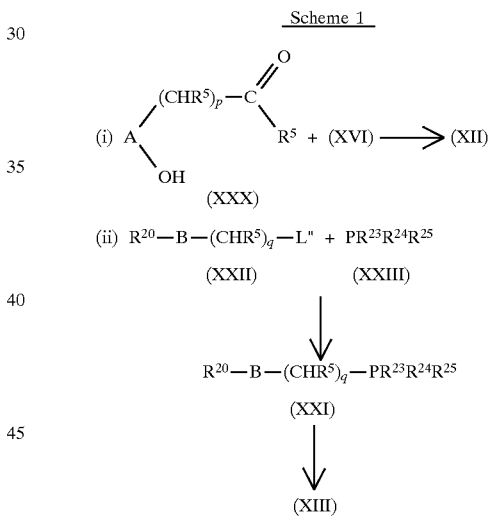

wherein B, $R^5$, $R^{20}$, $R^{23}$-$R^{25}$, p and q are as hereinabove defined and $L^{11}$ is a leaving group.

The compounds of the formulae (XII) and (XIII) are conveniently reacted together under conditions known for the Wittig reaction. For example in an inert solvent such as hexane, tetrahydrofuran, or diethyl ether in a temperature range of −78° C. to ambient. Preferably $R^{23}$-$R^{25}$ are all the same. In particular $R^{23}$-$R^{25}$ are all phenyl.

The compounds of the formula (XIII) are rarely isolatable and usually prepared in situ by deprotonating a compound of the formula (XXI) (scheme I). Deprotonazion is usually carried out in an inert solvent such as tetrahydrofruan or diethyl ether, in a temperature range of −78° C. to ambient, in the presence of a strong base. Examples of strong bases are lithium hexamethyldisilylamide, $CH_3SOCH_2^-Na^+$ and butyl lithium.

Compounds of the formula (XXI) may be prepared by reacting a compound of the formula (XXII) with a compound of the formula (XXIII) (scheme I). Suitable values for $L^{11}$ include halogen, such as chloro, bromo or iodo. Typically an inert solvent such as acetonitrile, diethyl ether, tetrahydrofuran or toluene is used and a temperature range of 50° C. or 120° C. The compounds of the formula (XXII) may be known or prepared from another compound of the formula (XXII) or a compound of the formula (XXIV):

(XXIV)

wherein B, $R^5$, $R^{20}$ and q are as hereinabove defined. For example the compound of the formula (XXIV) may be reduced to a compound of the formula (XXII) wherein $L^{11}$ is hydroxy. A compound of the formula (XXII), wherein $L^{11}$ is hydroxy, may then be converted to a compound of the formula (XXII) wherein $L^{11}$ is bromo by, for example, bromonating with N-bromosuccinimide.

Compounds of the formula (XII) are conveniently prepared by reacting together compounds of the formulae (XXX) and (XVI). The —C(=O)$R^5$ group may be protected if necessary. Reaction conditions for ether-forming reactions are known in the art, for example, those described below for the reaction between compounds of the formulae (XV) and (XVI).

Dehydration of compounds of the formula (XIV) is conveniently carried out using standard methods known in the art, for example, at elevated temperatures in the presence of sulphuric acid, phosphoric acid or aluminium oxide. The compounds of the formula (XIV) can be prepared by reacting a compound of the formula (XI) with a compound of the formula (XXV):

(XXV)

wherein A, $R^3$, $R^5$, $R^{21}$ and n are as hereinabove defined.

The reaction between compounds of the formulae (XI) and (XIV) is conveniently performed in the presence of a base such as butyl lithium, sec-butyl lithium, LDA or lithium hexamethyldisilylamide.

Compounds of the formula (XXV) are conveniently prepared by reacting together compounds of the formulae (XVI) and (XXVI)

(XXVI)

wherein A, $R^5$ and t are as hereinabove defined.

The reaction between compounds of the formulae (XVI) and (XXVI), in which of course the —C(=O)$R^5$ group may be protected, is carried out under conditions known in the art for such ether-forming reactions, for example as described for the reaction between compounds of the formulae (XV) and (XVI) below.

The ether-forming reaction between compounds of the formulae (XV) and (XVI) is typically performed in an inert solvent such as acetone or DMF, in a temperature range of ambient to 60° C., in the presence of a mild base. Suitable values for $L^1$ include tosylate, mesylate, triflate and halo, for example chloro or bromo. When $L^1$ is bromo, compounds of the formulae (XV) and (XVI) may, for example, be reacted together in DMF, at ambient temperature in the presence of a base such as potassium carbonate. When $L^1$ is hydroxy, the Mitsunobu reaction may be used (O. Synthesis, 1981, 1). For example reacting in tetrahydrofuran or toluene in the presence of diethyl azodicarboxylate and triphenylphosphine.

The compounds of the formula (XV) and XVI; may alternatively be reacted together using a phase transfer system.

Compounds of the formula (XV) may he prepared using processes a), b), c), d), e) or f) from the appropriate staring materials. Appropriate starting materials corresponding to compounds of the formulae (VII), (VIII), (IX), (X), (XII) and (XIV) have a hydroxy group (or protected hydroxy group), in place of the —OCH($R^3$)—Ph—($R^{21}$)$_n$ group.

The reaction between compounds of the formulae (XVII) and (XVIII) is conveniently carried out in the presence of a base, for example, lithium hydroxide or potassium tert-butoxide in an organic solvent such as an alcohol, for example, methanol.

The compounds of the formula (XVII) may be prepared by reacting a compound of the formula (XVI) with a compound of the formula (XIX):

(XIX)

wherein A and $R^5$ are as hereinabove defined. The reaction is conveniently carried out under standard conditions known in the art for such ether-forming reactions, for example, as described for the reaction between compounds of the formulae (XV) and (XVI).

The compounds of the formulae (XI), (XI), (XVIII), (XIX), (XX), (XXII), (XXIV), (XXVI) and (XXX) and starting materials for compounds of the formula (XV) are generally known in the art or can be made by methods analogous to or similar to those used in the examples or those known in the art for related compounds.

It is also possible to synthesise certain intermediates and even protected compounds using primarly ring synthesis. Here, reference is made to the compendiums 'The Chemistry of Heterocyclic Compounds' E. C. Taylor and A. Weissberger (published by John Wiley and Sons) and 'Comprehensive Heterocyclic Chemistry', A. R Katritzky and C. W Rees (published by Pergamon Press (Elsevier)).

Optional substituents may be converted into other optional substituents. For example an alkylthio group may be oxidised to an alkylsulphinyl or alkylsulphonyl group, a nitro group reduced to an amino group, a hydroxy group alkylated to a methoxy group, or a bromo group converted to an alkylthio group.

Various substituents may be introduced into compounds of the formulae (I) and (III) and intermediates in the preparation of compounds of the formulae (I) and (III), when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ether, a nitro group by nitration with concentrated nitric acid concentrated sulphuirc acid and bromination with bromine or tetra(n-butyl) ammonium tribromide.

It will be appreciated that, in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

As stated hereinbefore compounds of the formula (I) are antagonists of the pain enhancing effects of E-type prostaglandins and of value in the relief of mild to moderate pain which, for example, accompanies inflammatory conditions such as rheumatoid arthritis and osteoarthritis. Certain properties of the compounds may be demonstrated using the test procedures set out below:—

(a) an in-vitro guinea pig ileum assay which assesses the inhibitory properties of a test compound against $PGE_2$-induced contractions of the ileum; ileum was immersed in oxygenated Krebs solution containing indomethacin (4 $\mu$g/ml) and atropine (1 $\mu$M) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$-induced contraction of the ileum in the presence of the test compound was obtained; the $pA_2$ value for the test compound was calculated;

(b) an in-vivo assay in mice which assesses the inhibitory properties of a test compound against abdominal constriction response induced by the intraperitoneal administration of a noxious agent such as dilute acetic acid or phenylbenzoquinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):—

Test (a):- $pA_2$>5.3;

Test (b):- $ED_{30}$ in the range, for example, 0.01–100 mg/kg orally.

No overt toxicity or other untoward effects were noted in Test (b) when compounds of the formula I are administered at several multiples of their minimum inhibitory dose.

Prostaglandin receptors and in particular receptors for $PGE_2$ have been tentatively characterised by Kennedy et al. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 sensitive mediated effects were said to possess $EP_1$ receptors. Based on this compounds of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (1) or an in-vivo hydrolysable ester or amide or a pharmaceutically-acceptable salt thereof, for use in a method of treatment of the animal (including human) body by therapy.

According to a further feature of the invention there is provided the use of a compound of the formula I, or an in-vivo hydrolysable ester or amide or a pharmaceutically-acceptable salt thereof, in the manufacture of a medicament for use in the relief of pain in the animal (including human) body.

According to a further feature of the invention there is provided a method for the relief of pain in the animal (including human) body in need of such treatment which comprises administering to said body an effective amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

Although the compounds of the formula (I) are primarily of value as therapeutic agents for use in warm-blooded animals (including man), they are also useful whenever it is required to antagonise the effects of $PGE_2$ at the $EP_1$ receptor, based on test a). Thus, they are useful as pharmacological standards for use in the development of new biological tests and in the search for new pharmacological agents.

By virtue of their ability to relieve pain, the compounds of the formula I are of value in the treatment of certain inflammatory an non-inflammatory conditions which are currently treated with a cyclooxygenase-inhibitory non-steroidal anti- inflammatory drug (NSAID) such as indomethacin, ketorolac, acetylsalicyclic acid, ibuprofen, sulindac, tolmetin and piroxicam or other analgesics such as paracetamol, tramadol, Codein or in some circumstances morphine. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there as provided a pharmaceutical composition which comprises a compound of the formula (I), or an in-vivo hydrolysable ester or amide or pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with other anti-inflammatory agents such as an inhibitor of the enzyme 5-lipoxygenase (such as those disclosed in European Patent Applications Nos. 0351194, 0375368, 0375404, 0375452, 037547, 0381375, 0385662, 0385663, 0385679, 0385680).

The compounds of the formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, neurokinin and calcitonin gene related peptides (CGRP), or an alpha$_2$-adrenoceptor agonist, a GABA$_B$ receptor agonist, a calcium channel blocker, a sodium channel blocker, a CCK$_B$ receptor antagonist, or an antagonist or modulator of the action of glutamate at the NMDA receptor may usefully also be present in a pharmaceutical composition of the invention.

The compounds of the present invention may also be administered in bone diseases such as osteoporosis alone or in combination with calcitonin and bisphosphonates and estrogens.

The invention will now be illustrated in the following non-limiting Examples in which, unless otherwise stated:—

(i) evaporations were carried out by rotary evaporations in vacuo and work-up procedures were carried out after removal of residual solids by filtration;

(ii) yields are given for illustration only and are not necessarily the maximum attainable;

(iii) the end-products of the formula I have satisfactory microanalysis and their structures were generally confirmed by NMR and mass spectral techniques;

(iv) intermediates were not generally fully characterised and purity was assessed by thin layer chromatographic, infra-red (IR) or NMR analysis;

(v) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(vi) the following abbreviations have been used:
DMF N,N-dimethylformamide;
THF tetrahydrofuran;
DMSO dimethylsulphoxide;
DIBAL diisobutylaluminium hydride;
DEAD diethylazodicarboxylate.

EXAMPLE 1

4-[3-(2-Benzyloxyphenyl)propyl)benzoic acid (A) To a solution of methyl 4-[3-(2-benzyloxyphenyl)-propyl]benzoate (0.7 g) in ethanol was added 2M sodium hydroxide (1.45 ml). The mixture was stirred for 18 hours, evaporated to dryness and mixed with 1M HCl (50 ml) and ethyl acetate (50 ml). The solutions were separated and the organic solution washed with brine (50 ml), dried (magnesium sulphate), filtered and evaporated. The residue was purified by chromatography on silica gel using ethyl acetate: hexane (1:1) as eluant. There was thus obtained 4-[3-(2-benzyloxyphenyl)propyl]benzoic acid (391 mg) m.p. 109°-111° C.

The methyl 4-[3-(2-benzyloxyphenyl)propyl]benzoate was obtained as follows:

(B) A mixture of 2-hydroxyacetophenone (79 g), benzyl bromide (99.3 g) and potassium carbonate (80 g) in acetone (250 ml) was heated at reflux for 24 hours, filtered and the solvent evaporated. The residue was distilled (bp 138°-140° C., 0.05 mmHg and there was thus obtained 2-benzyloxyacetophenone (124 g).

(C) A mixture of methyl 4-formylbenzoate (36.28 g), 2-benzyloxyacetophenone (50 g) and potassium t-butoxide (2 g) in methanol (150 ml) was stirred for 3 hours. The precipitate that formed was filtered off. On standing further solid precipitated from the filtrates and was filtered off and combined with the first solid. There was thus obtained methyl 4-[3-(2-benzyloxyphenyl)-3-carbonyl-1(E)-propenyl]benzoate (74.2 g).

(D) A mixture of 4-[3-(2-benzyloxyphenyl)-3-carbonyl-1 (E)-propenyl]benzoate (35 g), 10% Pd-carbon (7 g), acetic acid (350 mil) and trifluoroacetic acid (7 ml) was warmed at 30° C. under 10 atm. of hydrogen for 18 hours, filtered and the filtrates evaporated. The residue was triturated with hexane and dried to give methyl 4-(3-(2-hydroxyphenyl)propyl]benzoate (26 g).

(E) First alternative method to synthesise methyl 4-[3-(2-hydroxyphenyl)propyl]benzoate. A mixture of 4-[3-(2-benzyloxyphenyl)-3-carbonyl-1(E)-propenyl]benzoate (25 g) and 11% Pd-carbon (2.5 g) in ethyl acetate (300 ml) was stirred under atmosphere of hydrogen for 18 hours, filtered and the solvent evaporated. There was thus obtained methyl 4-(3-(2-hydroxyphenyl)-3-carbonylpropyl]benzoate (21 g).

(F) To a stirred suspension of zinc powder (21 g) in water (50 ml) was added mercuric dichloride (1.5 g). After 20 minutes concentrated HCl (25 ml) was added and the mixture stirred for 2 minutes, the aqueous solution decanted off and a solution of methyl 4-[3-(2-hydroxyphenyl)-3-carbonylpropyl]benzoate (21 g) in methanol (100 ml) added followed by concentrated HCl (50 ml). The mixture was heated at reflux for 3 hours, cooled and the supernatant decanted off. The zinc residues were washed with diethyl ether (3×50 ml) and the combined organic washings and the supernatant were washed with water (100 ml), dried (magnesium sulphate), filtered and evaporated. The resulting oil was triturated with hexane to give methyl 4-[3-(2-hydroxyphenyl)propyl]benzoate (15.3 g) as a white solid.

(G) Second alternative method to synthesise methyl 4-[3-(2-hydroxyphenyl)propyl]benzoate. To a mixture of 2-(4-carboxyphenyl)-ethyltriphenylphosphonium bromide (prepared in the standard way from 4-(2-bromoethyl) benzoic acid and triphenylphosphine) (9.4 g) in THF (70 ml) was added lithium hexamethyldisilazide (40 ml, 1.0M solution in THF). After 1 hour a solution of 2-benzyloxybenzaldehyde (commercially available, or prepared from salicylaldehyde and benzyl bromide using the method described below to synthesise 4-[3-(2- hydroxyphenyl)propyl]benzoate) (4.0 g) in THF (40 ml) was added and the mixture stirred for 2 hours and poured into water (100 ml) and diethyl ether (100 ml). The aqueous layer was separated and washed with ethyl acetate (3×50 ml), acidified with 1 M HCl to pH1, and extracted with ethyl acetate (2×50 ml). The combined ethyl acetate extracts were washed with water 50 ml), dried (magnesium sulphate), filtered and evaporated to an orange oil (6 g).

(H) To a solution of the oil in methanol (100 ml) was added thionyl chloride (1.3 ml) at 0° C. The mixture was stirred for 2 hours, evaporated and the residue dissolved in ethyl acetate (100 ml), washed with sodium bicarbonate solution (50 ml) and brine (50 ml), the organic layer separated, dried (magnesium sulphate), filtered and evaporated. The resulting residue was purified by chromatography on silica gel using ethyl acetate: hexane (2:3) as eluant. There was thus obtained a straw coloured oil (4.2 g). 1.5 g of this material was converted to methyl 4-[3-(2-hydroxyphenyl)propyl]benzoate using the hydrogenation method described above (for the conversion of 4-[3-(2-benzyloxyphenyl)-3-carbonyl-1(E)-propenyl)benzoate to methyl 4-[3-(2-hydroxyphenyl)-3-carbonylpropyl]benzoate using ethanol as the reaction solvent). There was thus obtained methyl 4-[3-(2-hydroxy-phenyl)propyl] benzoate (1.1 g) as a white solid after purification by subjecting to chromatography on silica gel using ethyl acetate as eluant.

(I) To a solution of 4-[3-(2-hydroxyphenyl)propyl] benzoate (1.0 g) in DMF (20 ml) was added potassium carbonate (0.76 g) and benzyl bromide (0.66 ml). The mixture was stirred for 18 hours, poured into water (100 ml) and ethyl acetate (100 ml). The ethyl acetate solution was washed with water (3×100 ml), dried (magnesium sulphate), filtered and evaporated. The residue was purified by subjecting to chromatography on silica gel using diethyl ether: hexane (1:9) as eluant. There was thus obtained methyl 4-[3-(2-benzyloxy-phenyl)propyl]benzoate (0.7 g) as an oil.

EXAMPLE 2

The process described in Example 1 was repeated with the appropriate methyl 4-(3-(2-benzyloxyphenyl)propyl) benzoates to give the compounds described in the following table with appropriate modifications described in the notes below. The methyl 4-[3-(2-benzyloxyphenyl)propyl] benzoate precursors were prepared from methyl 4-(3-(2-hydroxyphenyl)propyl]benzoate and the appropriate benzyl halide using the method described in Example 1 for the preparation of methyl 4-[3-(2-benzyloxyphenyl)propyl] benzoate.

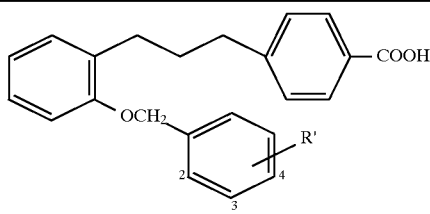

| Compd No | R' | m.p. | Footnote |
|---|---|---|---|
| 1 | 4-F | 79–80 | |
| 2 | 4-OMe | 128–129 | |
| 3 | 4-NO2 | 168–170 | |
| 4 | 4-Me | 119–120 | |
| 5 | 2-Me | 131–132 | |
| 6 | 3-Cl | 109–110 | |
| 7 | 2-Cl | 110.5–111 | |
| 8 | 4-Cl | 126.5–127.5 | |
| 9 | 3-NH2 | 125.5–126 | a |
| 10 | 3-NHCOMe | 198–198.5 | b |
| 11 | 3-OAllyl | 76.5–77.5 | c |
| 12 | 4-OAllyl | 92.5–93.5 | d |
| 13 | 3-OH | 103.5–104 | c,e |
| 14 | 2-OAllyl | 126–126.5 | f | a:- Methyl 4-[3-(2-(3-aminophenylmethyloxy)phenyl)propyl]-benzoate was prepared from methyl 4-[3-(2-(3-nitrophenylmethyloxy)-phenyl) propyl]benzoate (prepared from methyl 4-[3-(2-hydroxyphenyl)-propyl] benzoate and 3-nitrobenzyl chloride) as follows:
A mixture of methyl 4-[3-(2-(3-nitrophenylmethyloxy)-phenyl)propyl] benzoate (0.25 g), tin (II) chloride dihydrate (0.7 g) in ethanol (10 ml) was heated at 70° C. for 45 minutes, cooled and poured onto ice. The pH of the solution was adjusted to 8 with sodium bicarbonate and extracted with ethyl acetate (2 × 50 ml). The combined organics were washed with brine (50 ml), dried (magnesium sulphate), filtered and evaporated. The residue was purified by subjecting to chromatography on silica gel using ethyl acetate: hexane (1:9) as eluant. There was thus obtained methyl 4-[3-(2-(3-aminophenylmethyloxy)phenyl)propyl] benzoate (185 mg).
b:- Methyl 4-[3-(2-(3-methylcarbonylaminophenylmethyloxy)-phenyl) propyl]benzoate was prepared from methyl 4-[3-(2-(3-aminophenylmethyloxy)phenyl)propyl]benzoate (preparation described in note a) as follows:
To a mixture of methyl 4-[3-(2-(3-aminophenylmethyloxy)-phenyl)propyl] benzoate (0.2 g), triethylamine (0.19 ml) in dichloromethane (10 ml) at 5° C. was added acetic anhydride (0.08 ml). The mixture was stirred for 18 hours, the solvent evaporated, the residue dissolved in ethyl acetate (50 ml), and washed with 1M HCl (50 ml), sodium bicarbonate solution (50 ml) and brine (50 ml), dried (magnesium sulphate), filtered and evaporated. There was thus obtained methyl 4-[3-(2-(3-methyl-carbonylaminophenyl-methyloxy)-phenyl)propyl]benzoate (173 mg).
c:- (A) 3-Allyloxybenzyl chloride was obtained as follows:
A mixture of 3-hydroxybenzaldehyde (6 g), allyl bromide (6.25 g), and potassium carbonate (8.82 g) in DMF (30 ml) was stirred for 18 hours, poured into water (100 ml) and extracted with diethyl ether (3 × 150 ml). The combined organic extracts were washed with water (2 × 150 ml) and brine (2 × 150 ml), dried (magnesium sulphate) filtered and evaporated to give 2-allyloxybenzaldehyde (7.2 g).
(B) To a solution of 3-allyloxybenzaldehyde (7.2 g) in methanol (50 ml) at 0° C. was added sodium borohydride (1 g) in portions. The mixture was stirred for 30 minutes, evaporated, dissolved in 5% acetic acid and extracted with diethyl ether (3 × 100 ml), washed with water (2 × 100 ml), and sodium bicarbonate (2 × 100 ml), dried (magnesium sulphate), filtered and evaporated to give 3-allyl-oxybenzyl alcohol (7.26 g).
(C) To a solution of 3-allyloxybenzyl alcohol (7.2 g) in dichloromethane (100 ml) at 0° C. was added thionyl chloride (4.8 ml) in dichloromethane dropwise and a drop of DMF and the mixture stirred at ambient temperature for 1.5 hours, and poured into cold sodium bicarbonate solution. The organic layer was washed with sodium bicarbonate (2 × 100 ml), dried (magnesium sulphate), filtered and evaporated to give 3-allyloxybenzyl chloride (8.3 g).
d:- 4-Allyloxybenzyl chloride was made from 4-hydroxy-benzaldehyde using the methods in note c.
e:- Methyl 4-[3-(2-(3-hydroxyphenylmethyloxy)phenyl)propyl]-benzoate was obtained from methyl 4-[3-(2-(3-allyloxyphenylmethyl-oxy)phenyl)propyl]benzoate as follows:
To a solution of methyl 4-[3-(2-(3-allyloxy-phenylmethyloxy)phenyl) propyl]benzoate (0.66 g) and 2,2-dimethyl-1,3-dioxane-4,6-dione (0.46 g) in DMF (12 ml) was added palladium tetrakistriphenylphosphine (0.11 g) in DMF (12 ml) and the mixture was stirred for 18 hours in the dark with argon bubbling through the solution. The mixture was poured into ethyl acetate (100 ml) washed with water (2 × 100 ml), and sodium bicarbonate (2 × 100 ml), dried (magnesium sulphate), -continued

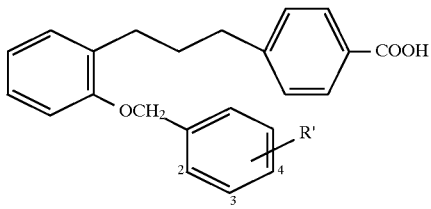

Compd No    R'    m.p.    Footnote filtered and evaporated. The residue was purified by subjecting to chromatography on silica gel using ethyl acetate: hexane (1:9, 2:8) as eluant. There was thus obtained methyl 4-[3-(2-(3-hydroxyphenyl-methyloxy)phenyl)propyl]benzoate (440 mg).
f:- 2-Allyloxybenzyl chloride was made from 2-hydroxy-benzaldehyde using the methods in note c.

a: Methyl 4-[3-(2-(3-aminophenylmethyloxy)phenyl) propyl]-benzoate was prepared from methyl 4-[3-(2-(3-nitrophenylmethyloxy)-phenyl)propyl] benzoate (prepared from methyl 4-[3-(2-hydroxyphenyl)-propyl]benzoate and 3-nitrobenzyl chloride) as follows:

A mixture of methyl 4-[3-(2-(3-nitrophenylmethyloxy)-phenyl)propyl]benzoate (0.25 g), tin (II) chloride dihydrate (0.7 g) in ethanol (10 ml) was heated at 70° C. for 45 minutes, cooled and poured onto ice. The pH of the solution was adjusted to 8 with sodium bicarbonate and extracted with ethyl acetate (2×50 ml). The combined organics were washed with brine (50 ml), dried (magnesium sulphate), filtered and evaporated. The residue was purified by subjecting to chromatography on silica gel using ethyl acetate hexane (1:9) as eluant. There was thus obtained methyl 4-[3-(2-(3-aminophenylmethyloxy)phenyl)propyl]benzoate (185 mg). b: - Methyl 4-[3-(2-(3-methylcarbonylaminophenylmethyloxy)-phenyl) propyl] benzoate was prepared from methyl 4-[3-(2-(3-aminophenylmethyloxy)phenyl)propyl]benzoate (preparation described in note a) as follows:

To a mixture of methyl 4-[3-(2-(3-aminophenylmethyloxy)-phenyl)propyl]benzoate (0.2 g), triethylamine (0.19 ml) in dichloromethane (10 ml) at 5° C. was added acetic anhydride (0.08 ml). The mixture was stirred for 18 hours, the solvent evaporated, the residue dissolved in ethyl acetate (50 ml), and washed with 1M HCl (50 ml), sodium bicarbonate solution (50 ml) and brine (50 ml), dried (magnesium sulphate), filtered and evaporated. There was thus obtained methyl 4-[3-(2-(3-methylcarbonylaminophenyl-methyloxy)-phenyl)propyl] benzoate (173 mg).

c:- (A) 3-Allyloxybenzyl chloride was obtained as follows: A mixture of 3-hydroxybenzaldehyde (6 g), allyl bromide (6.25 g), and potassium carbonate (8.82 g) in DENT (30 ml) was stirred for 18 hours, poured into water (100 ml) and extracted with diethyl ether (3×150 ml). The combined organic extracts were washed with water (2×150 ml) and brine (2×150 ml), dried (magnesium sulphate) filtered and evaporated to give 2-allyloxybenzaldehyde (7.2 g).

(B) To a solution of 3-allyloxybenzaldehyde (7.2 g) in methanol (50 ml) at 0° C. was added sodium borohydride (1 g) in portions. The mixture was stirred for 30 minutes, evaporated dissolved in 5% acetic acid and extracted with diethyl ether (3×100 ml) , washed with water (2×100 ml), and sodium bicarbonate (2×100 ml), dried (magnesium sulphate), filtered and evaporated to give 3-allyloxybenzyl alcohol (7.26 g).

(C) To a solution of 3-allyloxybenzyl alcohol (7.2 g) in dichloromethane (100 ml) at 0° C. was added thionyl chloride (4.8 ml) in dichloromethane dropwise and a drop of DMF and the mixture stirred at ambient temperature for 1.5 hours, and poured into cold sodium bicarbonate solution. The organic layer was washed with sodium bicarbonate (2×100 ml), dried (magnesium sulphate), filtered and evaporated to give 3-allyloxybenzyl chloride (8.3 g).

d:- 4-Allyloxybenzyl chloride was made from 4-hydroxybenzaldehyde using the methods in note c.

e:- Methyl 4-[3-(2-(3-hydroxyphenylmethyloxy)phenyl) propyl]-benzoate was obtained from methyl 4-[3-(2-(3-allyloxyphenylmethyl-oxy)phenyl)propyl]benzoate as follows:

To a solution of methyl 4-[3-(2-(3-allyloxy-phenylmethyloxy)phenyl)propyl]benzoate (0.66 g) and 2,2-dimethyl-1,3-dioxane-4,6-dione (0.46 g) in DMF (12 ml) was added palladium tetrakistriphenylphosphine (0.11 g) in DMF (12 ml) and the mixture was stirred for 18 hours in the dark with argon bubbling through the solution. The mixture was poured into ethyl acetate (100 ml) washed with water (2×100 ml), and sodium bicarbonate (2×100 ml), dried (magnesium sulphate), filtered and evaporated. The residue was purified by subjecting to chromatography on silica gel using ethyl acetate:hexane (1:9, 2:8) as eluant. There was thus obtained methyl 4-[3-(2-(3-hydroxyphenylmethyloxy) phenyl)propyl]benzoate (440 mg).

f:- 2-Allyloxybenzyl chloride was made from 2-hydroxybenzaldehyde using the methods in note c.

EXAMPLE 3

(A) The process described in Example 1 was repeated with the appropriate methyl 4-[3-(2-benzyloxyphenyl) alkyllbenzoates or 4-[3-(2-benzyloxyphenyl)alkyl) phenylethanoates to give the compounds described in the following table with appropriate modifications described in the notes below.

(B) The substituted methyl 4-[2-hydroxyphenylalkyl]-benzoate and 4-(2-hydroxyphenylalkyllphenylethanoate compounds were obtained from the corresponding 2-benzyloxybenzaldehyde using a similar method to that of example 1 (B) or benzyloxyphenylacetaldehydes obtained from the corresponding 2-hydroxybenzaldehydes and phosphonium salts using the second alternative method to synthesise methyl 4-[3-(2-hydroxyphenyl)propyl]-benzoate described in Example 1 unless stated otherwise in the notes.

(C) The methyl 4-[3-(2-benzyloxyphenyl)alkyl]benzoate precursors were prepared from the substituted methyl 4-(2-hydroxyphenyl)-alkyl]benzoate or 4-(2-hydroxyphenyl) alkyl]phenylethanoate compounds and benzyl bromide using the method describe example 1 for the preparation of methyl 4-[3-(2-benzyloxyphenyl-propyl]benzoate unless stated otherwise in the notes.

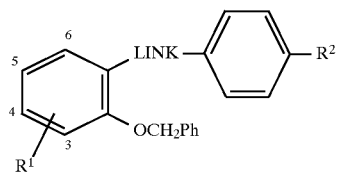

| Compd No. | R1 | Link | R2 | m.p. | Foot-note |
|---|---|---|---|---|---|
| 1 | H | $CH_2CH_2$ | $CO_2H$ | 143–144 | a |
| 2 | H | $CH_2CH_2$ | $CH_2CO_2H$ | 88–89 | b |
| 3 | 5-Cl | $CH_2CH_2$ | $CH_2CO_2H$ | 91–92 | b |
| 4 | 5-F | $CH_2CH_2CH_2$ | $CO_2H$ | 102–103 | |
| 5 | 5-Cl | $CH_2CH_2CH_2$ | $CO_2H$ | 95.5–96.5 | |
| 6 | 5-OMe | $CH_2CH_2CH_2$ | $CO_2H$ | 102–103 | |
| 7 | 6-OMe | $CH_2CH_2CH_2$ | $CO_2H$ | 90–91 | |
| 8 | 4-OMe | $CH_2CH_2CH_2$ | $CO_2H$ | 121–121.5 | |
| 9 | 6-F | $CH_2CH_2CH_2$ | $CO_2H$ | 92–93 | |
| 10 | 3,5-diCl | $CH_2CH_2CH_2$ | $CO_2H$ | 163–163.5 | |
| 11 | 5-$NO_2$ | $CH_2CH_2CH_2$ | $CO_2H$ | 161–163 | c |
| 12 | 5-$NH_2$ | $CH_2CH_2CH_2$ | $CO_2H$ | 152–155 | d |
| 13 | 5-NHCOMe | $CH_2CH_2CH_2$ | $CO_2H$ | 181–183 | e |
| 14 | 5-$NHCO_2Et$ | $CH_2CH_2CH_2$ | $CO_2H$ | 165–167 | f |
| 15 | 5-$NHSO_2Ph$ | $CH_2CH_2CH_2$ | $CO_2H$ | 159–161 | g |
| 16 | 5-NHMe | $CH_2CH_2CH_2$ | $CO_2H$ | 153–154 | h |
| 17 | 5-$NEt_2$ | $CH_2CH_2CH_2$ | $CO_2H$ | 67–68 | i |
| 18 | 5-COMe | $CH_2CH_2CH_2$ | $CO_2H$ | 147–147.5 | j |
| 19 | 5-CO-nPentyl | $CH_2CH_2CH_2$ | $CO_2H$ | 136–136.5 | k |
| 20 | 5-n-Hexyl | $CH_2CH_2CH_2$ | $CO_2H$ | 91.5–92 | l |
| 21 | 5-Br | $CH_2CH_2CH_2$ | $CO_2H$ | 115–118 | m |
| 22 | 5-CN | CH2CH2CH2 | $CO_2H$ | 134–135 | n |
| 23 | 5-CHO | $CH_2CH_2CH$ | $CO_2H$ | 126–127 | o |
| 24 | 5-$CH_2OH$ | $CH_2CH_2CH_2$ | $CO_2H$ | 102–103 | p |
| 25 | 5-C(NOH)Me | $CH_2CH_2CH_2$ | $CO_2H$ | 166.5–167.5 | q |
| 26 | 5-C(NOH)H | $CH_2CH_2CH_2$ | $CO_2H$ | 143.5–144 | r |
| 27 | 5-C(NOMe)Me | $CH_2CH_2CH_2$ | $CO_2H$ | 121–122 | s |
| 28 | 5-Cl | $CH_2CH_2$ | $CO_2H$ | 145–147 | a |
| 29 | 5-$NO_2$ | $CH_2CH_2$ | $CO_2H$ | 183–184 | a,t |
| 30 | 5-SOMe | $CH_2CH_2CH_2$ | $CO_2H$ | 101–102 | u |
| 31 | 5-$SO_2Me$ | $CH_2CH_2CH_2$ | $CO_2H$ | 185 | v |
| 32 | H | $CH_2CH_2CH_2$ | $CONHCH_2CO_2H$ | 101–102 | w |
| 33 | H | $CH_2CH_2CH_2$ | $CONH(CH_2)_2CO_2$ | 115–116 | x |
| 34 | 5,6-CH=CH—CH=CH— | $CH_2CH_2CH_2$ | $CO_2H$ | 128–130 | |
| 35 | 5,6-$(CH_2)_4$— | $CH_2CH_2CH_2$ | $CO_2H$ | 138–139 | y |
| 36 | 3-$NO_2$ | $CH_2CH_2CH_2$ | $CO_2H$ | 117–119 | |
| 37 | 5-C(O)$CHMe_2$ | $(CH_2)_3$ | $CO_2H$ | 135–137 | z |
| 38 | 5-C(=N—OH)$CHMe_2$ | $(CH_2)_3$ | $CO_2H$ | 170–176 | (aa) |
| 39 | 5-COEt | $(CH_2)_3$ | $CO_2H$ | 116–118 | (ab) |
| 40 | 5-COPh | $(CH_2)_3$ | $CO_2H$ | 142–144 | (ac) |
| 41 | 5-C(=N—OH)Et | $(CH_2)_3$ | $CO_2H$ | 168–170 | (aa) |
| 42 | 5-C(=N—OH)Ph | $(CH_2)_3$ | $CO_2H$ | 180–189 | (aa) |
| 43 | 5-C(=$NNHCONH_2$)$CH_3$ | $(CH_2)_3$ | $CO_2H$ | 158–160 | (ad) |
| 44 | 5-C(=$NHNH_2$)$CH_3$ | $(CH_2)_3$ | $CO_2H$ | 174–180 | (ae) |
| 45 | 5-C(=NHNHPh)$CH_3$ | $(CH_2)_3$ | $CO_2H$ | 143–147 | (af) |
| 46 | 5-$CH_2OMe$ | $(CH_2)_3$ | $CO_2H$ | 81–84 | (ag) |
| 47 | 5-$CH_2SMe$ | $(CH_2)_3$ | $CO_2H$ | 107.5–111 | (ah) |
| 48 | 5-$CH_2SO_2Me$ | $(CH_2)_3$ | $CO_2H$ | 159.5–164 | (ai) |
| 49 | 5-$CH_2SOMe$ | $(CH_2)_3$ | $CO_2H$ | 137.5–140.5 | (ai) |
| 50 | (S—C=N—CH=C—O ring) | $(CH_2)_3$ | $CO_2H$ | 177.5–181.5 | (aj) |
| 51 | 5-$NEt_2$ | $(CH_2)_3$ | $CO_2H$ | 67–68 | (ak) |
| 52 | 5-Br | $(CH_2)_2$ | $CO_2H$ | 166–167 | (al) | a: (4-Carboxyphenylmethyl)triphenylphosphonium bromide was prepared in the standard way from 4-(bromomethyl)benzoic acid and triphenylphosphine.

b: (4-Carboxymethylphenylmethyl)triphenylphosphonium bromide was prepared in the standard way from 4-(bromomethyl)phenylacetic acid and triphenylphosphine.

c: Methyl 4-[3-(2-hydroxy-5-nitrophenyl)propyl]benzoate was prepared from methyl 4-[3-(2-hydroxyphenyl)propyl]benzoate (see Example 1) as follows:
Nitric acid (15M, 3.13 ml) was added to acetic anhydride (12.52 ml) a 0° C. and the mixture stirred for 15 minutes, then added to a stirred solution of methyl 4-[3-(2-hydroxy-phenyl)propyl]benzoate (12.89 g) in acetic anhydride (300 ml) at 0° C. and stirred for 18 hours. The solvent was evaporated and the resulting yellow oil purified by chromatography on -continued

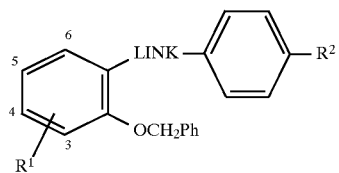

| Compd No. | R1 | Link | R2 | m.p. | Footnote |
|---|---|---|---|---|---| silica gel using ethyl acetate:hexane (1:9 to 1:1 gradient) as eluant to give methyl 4-[3-(2-hydroxy-3-nitrophenyl)propyl]benzoate (5.4 g) and methyl 4-[3-(2-hydroxy-5-nitrophenyl)propyl]benzoate (7.5 g).

d: Methyl 4-[3-(2-benzyloxy-5-aminophenyl)propyl]benzoate was prepared from methyl 4-[3-(2-benzyloxy-5-nitrophenyl)propyl]benzoate using the process described in Example 2, note a.

e: Methyl 4-[3-(2-benzyloxy-5-methylcarbonylaminophenyl)propyl]benzoate was prepared from methyl 4-[3-(2-benzyloxy-5-aminophenyl)-propyl]benzoate by the method described in Example 2, note b.

f: Methyl 4-[3-(2-benzyloxy-5-ethoxycarbonylaminophenyl)propyl]benzoate was prepared from methyl 4-[3-(2-benzyloxy-5-aminophenyl)-propyl]benzoate by the method described in Example 2, note b using ethyl chloroformate in the place of acetic anhydride as the acylating agent.

g: Methyl 4-[3-(2-benzyloxy-5-phenylsulphonamidophenyl)propyl]benzoate was prepared from methyl 4-[3-(2-benzyloxy-5-aminophenyl)-propyl]benzoate as follows:
To a mixture of methyl 4-[3-(2-benzyloxy-5-aminophenyl)-propyl]benzoate (0.3 g) and potassium carbonate (170 mg) was added benzenesulphonyl chloride (0.15 ml) and the mixture stirred for 18 hours, poured into ethyl acetate (50 ml) and washed with 1M HCl (50 ml), sodium bicarbonate (50 ml) and brine (50 ml). The organic solution was dried (magnesium sulphate), filtered and evaporated. The residue was purified by subjecting to chromatography on silica gel using ethyl acetate:hexane (3:7) as eluant. There was thus obtained methyl 4-[3-(2-benzyloxy-5-phenylsulphonamidophenyl)propyl]benzoate (150 mg).

h: Methyl 4-[3-(2-benzyloxy-5-(trifluoromethylcarbonylamino)-phenyl)propyl]benzoate was synthesised from methyl 4-[3-(2-benzyloxy-5-aminophenyl)propyl]benzoate using the method described in Example 2, note b using trifluoromethylacetic anhydride in the place of acetic anhydride as the acylating agent.
To a mixture of NaH (50% by weight in oil) (20 mg) in DMF (5 ml) was added methyl 4-[3-(2-benzyloxy-5-(trifluoromethylcarbonylamino)phenyl)propyl]benzoate (200 mg).
After 1 hour, MeI (0.2 ml) was added and the mixture stirred for 18 hours. The mixture was poured into 1M HCl (50 ml), and extracted with ethyl acetate (2 × 25 ml). The organics were washed with brine (50 ml), dried (magnesium sulphate), filtered and evaporated. There was thus obtained methyl 4-(3-(2-benzyloxy-5-(N-methyl-trifluoromethylcarbonylamino)phenyl)-propyl]benzoate (200 mg). 4-[3-(2-Benzyloxy-5-methylaminophenyl)propyl]benzoic acid was obtained from methyl 4-[3-(2-benzyloxy-5-(N-methyltrifluoromethylcarbonyl-amino)phenyl)propyl]benzoate by the standard hydrolysis method.

i: Methyl 4-[3-(2-benzyloxy-5-(N,N-diethylamino)phenyl)propyl]-benzoate was obtained from methyl 4-[3-(2-benzyloxy-5-aminophenyl)-propyl]benzoate as follows:
To a mixture of methyl 4-[3-(2-benzyloxy-5-aminophenyl)-propyl]benzoate (250 mg) in DMF (10 ml) was added potassium carbonate (200 mg) and ethyl iodide (0.16 ml).
The mixture was stirred for 18 hours, poured into ethyl acetate (50 ml) and washed with brine (50 ml), dried (magnesium sulphate), filtered and evaporated. The residue was purified by chromatography on silica gel using ethyl acetate:hexane (3;7) as eluant. There was thus obtained methyl 4-[3-(2-benzyloxy-5-(N,N-diethylamino)phenyl)propyl]benzoate (150 mg).

j: Methyl 4-[3-(2-hydroxy-5-acetylphenyl)propyl]benzoate was obtained from methyl 4-[3-(2-hydroxyphenyl)propyl]benzoate as follows:
To a cooled (0° C.) solution of aluminium chloride (311 mg) in nitrobenzene (5 ml) was added methyl 4-[3-(2-hydroxyphenyl)propyl]-benzoate (0.6 g) then acetyl chloride (0.16 ml). The mixture was heated at 50° C. for 3 hours, aluminium chloride (622 mg) added and the mixture was heated at 50° C. for a further 3 hours. The mixture was poured into 1M HCl (100 ml) and ethyl acetate (100 ml), the organic layer washed with sodium bicarbonate (100 ml) and brine (100 ml), dried (magnesium sulphate), filtered and evaporated. The residue was purified by subjecting to chromatography on silica gel using ethyl acetate:dichloromethane (0:100, 5:95 gradient) as eluant. There was thus obtained methyl 4-[3-(2-hydroxy-5-acetylphenyl)propyl]benzoate (360 mg).

k: Methyl 4-[3-(2-hydroxy-5-hexanoylphenyl)propyl]benzoate was obtained from methyl 4-[3-(2-hydroxyphenyl)propyl]benzoate by the method described in note j using hexanol chloride in place of acetyl chloride.

l: Methyl 4-[3-(2-benzyloxy-5-hexylphenyl)propyl]benzoate was obtained from methyl 4-[3-(2-benzyloxy-5-hexanoylphenyl)propyl]-benzoate (synthesised from methyl 4-[3-(2-hydroxy-5-hexanoylphenyl)-propyl]benzoate using the benzylation method described in Example 1B) as follows:
To a solution of methyl 4-[3-(2-benzyloxy-5-hexanoylphenyl)-propyl]benzoate (280 mg) in trifluoroacetic acid (0.47 ml) was added triethylsilane (0.49 ml) and the mixture stirred for 18 hours.
Trifluoroacetic acid (0.47 ml) and triethylsilane (0.49 ml) were added and the mixture stirred for a further 4 hours. The reaction mixture was purified by subjecting to -continued

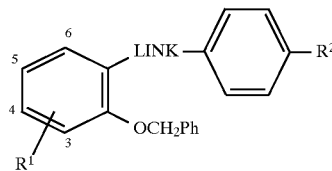

| Compd No. | R1 | Link | R2 | m.p. | Foot-note |
|---|---|---|---|---|---| chromatography on silica gel using dichloromethane as eluant. There was thus obtained methyl 4-[3-(2-benzyloxy-5-hexylphenyl)propyl]benzoate (210 mg).

m: Methyl 4-[3-(2-hydroxy-5-bromophenyl)propyl]benzoate was obtained from methyl 4-[3-(2-hydroxyphenyl)propyl]benzoate as follows:
To a mixture of methyl 4-(3-(2-hydroxyphenyl)propyl]benzoate (1.5 g) in chloroform (25 ml) was added tetrabutylammonium tribromide (3.12 g). The mixture was stirred for 2 hours, washed with sodium thiosulphate (100 ml), and water (3 × 100 ml), dried (magnesium sulphate), filtered and evaporated. The residue was purified by chromatography on silica gel using ethyl acetate:hexane (3:7) as eluant. There was thus obtained methy 4-[3-(2-hydroxy-5-bromophenyl)-propyl]-benzoate (1.9 g).

n: Methyl 4-[3-(2-benzyloxy-5-cyanophenyl)propyl]benzoate was obtained from methyl 4-[3-(2-benzyloxy-5-bromophenyl)propyl]benzoate as follows:
A mixture of methyl 4-[3-(2-benzyloxy-5-bromophenyl)propyl]benzoate (0.5 g) and CuCN (250 mg) in DMF (20 ml) was heated at reflux for 18 hours, poured into ethylene diamine (20 ml) and water (60 ml) and extracted with ethyl acetate (3 × 100 ml). The combined extracts were washed with brine (100 ml), dried (magnesium sulphate), filtered and evaporated to give methyl 4-[3-(2-benzyloxy-5-cyanophenyl)propyl]benzoate (290 mg).

o: Methyl 4-[3-(2-hydroxy-5-formylphenyl)propyl]benzoate was obtained from methyl 4-[3-(2-hydroxyphenyl)propyl]-benzoate as follows:
To a mixture of methyl 4-[3-(2-hydroxyphenyl)propyl]-benzoate in dichloromethane (12 g) at −5° C. was added titanium tetrachloride (1M solution in dichloromethane, 97.8 ml) then 1,1-dichloromethyl methylether (4.83 ml) in dichloromethane (50 ml). The mixture was stirred for 2 hours at −5° C. then 3 hours at ambient temperature, poured into ice and concentrated HCl (2 ml) was added. The mixture was stirred with diethyl ether (200 ml) for 30 minutes, the layers separated and the aqueous layer extracted with ethyl acetate (3 × 200 ml). The combined organic solutions were dried (magnesium sulphate), filtered and evaporated. The residue was purified by chromatography on silica gel using ethyl acetate: dichloromethane (0:100 to 10:90 gradient) as eluant. Two products were isolated, methyl 4-[3-(2-hydroxy-3-formylphenyl)propyl]-benzoate (2.40 g) eluted first, and methyl 4-[3-(2-hydroxy-5-formyl-phenyl)propyl]benzoate (6.39 g) eluted second.

p: Methyl 4-[3-(2-benzyloxy-5-hydroxymethylphenyl)propyl]-benzoate was obtained from methyl 4-[3-(2-benzyloxy-5-formylphenyl)-propyl]benzoate as follows:
A mixture of methyl 4-[3-(2-benzyloxy-5-formylphenyl)-propyl]benzoate (0.97 g) and sodium borohydride (142 mg) in ethanol (10 ml) was stirred at 0° C. for 30 minutes at ambient temperature for 1 hour, the solvent was evaporated, the residue mixed with ethyl acetate (100 ml) and washed with 1M HCl (100 ml), sodium bicarbonate (100 ml) and brine (100 ml), dried (magnesium sulphate), filtered and evaporated. The residue was purified by subjecting to chromatography on silica gel using ethyl acetate:dichloromethane (0:100 to 5:95 gradient) as eluant. There was thus obtained methyl 4-[3-(2-benzyloxy-5-hydroxymethylphenyl)propyl]benzoate (0.94 g).

q: Methyl 4-[3-(2-benzyloxy-5-(acetyloxime)phenyl)propyl]-benzoate was obtained from methyl 4-[3-(2-benzyloxy-5-acetylphenyl)-propyl]benzoate as follows:
A mixture of methyl 4-[3-(2-benzyloxy-5-acetylphenyl)-propyl]benzoate (402 mg) and hydroxylamine hydrochloride (139 mg) in pyridine (5 ml) was heated at 60° C. for 2 hours, evaporated and the residue was purified by subjecting to chromatography on silica gel using ethyl acetate:dichloromethane (5:95) as eluant. There was thus obtained methyl 4-[3-(2-benzyloxy-5-(acetyloxime)phenyl)propyl]-benzoate (0.38 g).

r: Methyl 4-[3-(2-benzyloxy-5-(formyloxime)phenyl)propyl]-benzoate was obtained from methyl 4-[3-(2-benzyloxy-5-formylphenyl)-propyl]benzoate by a similar method to that described in note q.

s: Methyl 4-[3-(2-benzyloxy-5-(O-methylacetyloxime)phenyl)-propyl]benzoate was obtained from methyl 4-[3-(2-benzyloxy-5-(acetyloxime)-phenyl)propyl]benzoate as follows:
A mixture of methyl 4-[3-(2-benzyloxy-5-(acetyloxime)-phenyl)propyl]benzoate (390 mg) and NaH (50% by weight in oil) (60 mg) was stirred for 30 minutes. MeI (0.23 ml) was added and the mixture stirred for 2 hours. A further 100 mg of NaH (50% by weight in oil) and 1 ml of MeI was added and the mixture stirred for 18 hours, poured into 1M HCl (100 ml) and extracted with ethyl acetate (100 ml) and the solvent evaporated. The residue was purified by chromatography on silica gel using dichloromethane:hexane (0:100 to 80:20 gradient) as eluant. There was thus obtained methyl 4-[3-(2-benzyloxy-5-(acetyloxime)phenyl)propyl]benzoate (150 mg).

t: Methyl 4-[2-(2-hydroxy-5-nitrophenyl)ethyl]benzoate was prepared from methyl 4-[3-(2-hydroxyphenyl)ethyl]benzoate by a similar method to that described in note c.

u: Methyl 4-[3-(2-benzyloxy-5-methanesulphinyl)phenyl)propyl]benzoate was obtained from the corresponding methylthio compound (see example 7) by a modification of the method in example 49 in which mCPBA was added at 0° C. and the reaction terminated when all the methylthio compound was consumed.

v: Methyl 4-[3-(2-benzyloxy-5-methanesulphonylphenyl)propyl]benzoate ester

-continued

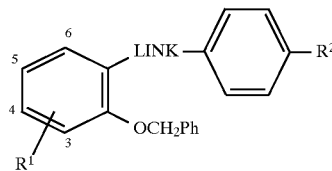

| Compd No. | R1 | Link | R2 | m.p. | Foot-note |
|---|---|---|---|---|---| was obtained from the corresponding methylthio compound (see example 7) by a similar method to that of Example 49.

w: The ethyl ester was obtained using a similar method to that described in Example 45 (compound 51).

x: The ethyl ester was obtained using a similar method to that described in Example 45 (compound 52).

y: Methyl 4-[3-(2-hydroxy-5,6,7,8-tetrahydro-1-naphthyl)propyl]benzoate was obtained as a by-product from the reduction of methyl 4-[3-(2-benzyloxy-1-naphthyl)-2-propenyl]benzoate and methyl 4-[3-(2-benzyloxy-1-naphthyl)-1-propenyl]benzoate (mixture of double bond isomers) obtained as an intermediate to compound 34 (Example 3).

z: Methyl 4-[3-(2-hydroxy-5-(2-methylpropionyl)phenyl)propyl]benzoate was obtained from methyl 4-[3-(2-hydroxyphenyl)propyl]benzoate using and 2-methylpropionyl chloride using the method described in Example 3 Footnote j.

aa: The methyl 4-[3-(2-benzyloxy-5-hydroxyiminoalkylphenyl)propyl]-benzoates were obtained from the corresponding methyl 4-[3-(2-benzyloxy-5-alkanoylphenyl)propyl]benzoate compounds by a similar method to that of Example 3, Footnote q as a mixture of the Z and E isomers.

ab: Methyl 4-[3-(2-hydroxy-5-propionylphenyl)propyl]benzoate was obtained from methyl 4-[3-(2-hydroxyphenyl)propyl]benzoate and EtCOCl using a similar method to that of Example 3, Footnote j.

ac: Methyl 4-[3-(2-hydroxy-5-benzoylphenyl)propyl]benzoate was obtained from methyl 4-[3-(2-hydroxyphenyl)propyl]benzoate and PhCOCl using a similar method to that of Example 3, Footnote j.

ad: Methyl 4-[3-(2-benzyloxy-5-(1-semicarbazonoethyl)phenyl)propyl]benzoate (mpt. 158–160° C.) was obtained as follows:-
A mixture of methyl 4-[3-(2-benzyloxy-5-acetylphenyl)propyl]benzoate (0.5 g), $NH_2CONHNH_2$. HCl (0.14 g) and pyridine (5 drops) in methanol (20 ml) was heated under reflux for 90 minutes, cooled and the resulting white solid isolated by filtration and washed with ethanol and ether.

ae: Methyl 4-[3-(2-benzyloxy-5-(1-hydrazonoethyl)phenyl)propyl]benzoate was obtained as follows:-
A mixture of methyl 4-[3-(2-benzyloxy-5-acetylphenyl)propyl]benzoate (0.5 g) and hydrazine hydrate (1.2 ml) in ethanol (20 ml) was heated at reflux in a soxhlet apparatus using $Na_2SO_4$ as the drying agent, for 3 hours. The solvent was evaporated and the residue extracted with EtOAc and washed with saturated aqueous $NaHCO_3$ solution.

af: Methyl 4-[3-(2-benzyloxy-5-(1-phenylhydrazonoethyl)phenyl)propyl]benzoate was obtained using a similar method to that of Example 3 Footnote ae, with the modification that 3 drops of glacial acetic acid were added to the reaction mixture.

ag: Methyl 4-[3-(2-benzyloxy-5-methoxymethylphenyl)propyl]benzoate was obtained as follows:-
To a solution of methyl 4-[3-(2-benzyloxy-5-hydroxymethylphenyl)propyl]benzoate (5.31 g) in methanol (100 ml) was added 4-methylbenzenesulphonic acid (3.11 g). The reaction was heated at reflux for 18 hours, the solvent evaporated, the residue dissolved in EtOAc, washed with brine and the solvent evaporated to give methyl 4-[3-(2-benzyloxy-5-methoxymethylphenyl)propyl]benzoate (3.64 g).

ah: To a stirred solution of methyl 4-[3-(2-benzyloxy-5-hydroxymethyl-phenyl)propyl]benzoate (1.57 g) in $CH_2Cl$ (15 ml), at −20° C., was added methanesulphonyl chloride (0.37 ml), triethylamine (0.84 ml) and DMAP (0.29 g). The reaction was stirred at −20° C. for 5 hours, diluted with $CH_2Cl_2$ (50 ml) and washed with water, saturated aqueous $NaHCO_3$ and brine. The organic layer was dried ($MgSO_4$), filtered and evaporated to give a white solid (1.37 g).
To the white solid (1.37 g) in DMF (10 ml) was added sodium thiomethoxide (0.24 g) in DMF (10 ml). The reaction mixture was stirred for 8 hours, the solvent evaporated and the residue washed with water and extracted with ethyl acetate. The organic solution was washed with brine, dried ($MgSO_4$), filtered and evaporated, to give methyl 4-[3-(2-benzyloxy-5-methanethiomethylphenyl)propyl]benzoate (0.68 g) which crystallised on standing.

ai: Methyl 4-[3-(2-benzyloxy-5-methanesulphinylmethylphenyl)propyl]benzoate and methyl 4-[3-(2-benzyloxy-5-methanesulphonylmethylphenyl)propyl]benzoate were prepared as a mixture from the methyl 4-[3-(2-benzyloxy-5-methanethiomethylphenyl) propyl]benzoate using a similar method to that of Example 49 and separated by MPLC, eluting with ethyl acetate.

aj: Methyl 4-[3-(2-benzyloxy-5-(oxazol-5-yl)phenyl]benzoate was prepared as follows:-
To a mixture of methyl 4-[3-(2-benzyloxy-5-formylphenyl)propyl]benzoate (0.75 g) and potassium carbonate (0.696 g) in methanol (60 ml) was added tosylmethyl isocyanide (0.54 g). The reaction was heated at reflux for 30 minutes, the solvent evaporated -continued

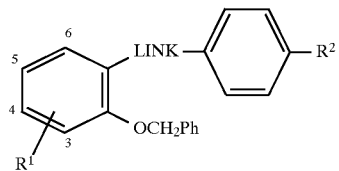

| Compd No. | R1 | Link | R2 | m.p. | Footnote |
|---|---|---|---|---|---| and the residue partitioned between water and $CH_2Cl_2$. The $CH_2Cl_2$ was washed with $H_2O$, dried ($MgSO_4$), filtered and evaporated. The residue was purified by MPLC, eluting with 3% $EtOAC/CH_2Cl_2$ to give methyl 4-[3-(2-benzyloxy-5-(oxaxol-5-yl)phenyl]benzoate (290 mg).

ak: Methyl 4-[3-(2-benzyloxy-5-(diethylamino)phenyl)propyl]benzoate was prepared as follows:-
To a mixture of methyl 4-[3-(2-benzyloxy-5-aminophenyl)propyl]benzoate (250 mg) in DMF (5 ml) was added potassium carbonate (0.2 g) and iodoethane (0.16 ml). The reaction was stirred for 18 hours, diluted with EtOAc, washed with water and brine, dried ($MgSO_4$), filtered and evaporated. The residue was purified by flash chromatography to give the methyl 4-[3-(2-benzyloxy-5-(diethylamino)phenyl)propyl]benzoate as an oil (150 mg).

al: Methyl 4-[2-(2-benzyloxy-5-bromophenyl)ethyl]benzoate was prepared from methyl 4-[2-(2-hydroxyphenyl)ethyl]benzoate using a similar method to that of Example 3 Footnote m.

a:- (4-Carboxyphenylmethyl)triphenylphosphonium bromide was prepared in the standard way from 4-(bromomethyl)benzoic acid and triphenylphosphine.

b:- (4-Carboxymethylphenylmethyl)triphenylphosphonium bromide prepared in the standard way from 4-(bromomethyl)phenylacetic acid and triphenylphosphine.

c:- Methyl 4-[3-(2-hydroxy-5-nitrophenyl)propyl]benzoate was prepared from methyl 4-[3-(2-hydroxyphenyl)propyl]benzoate (see Example 1) as follows:

Nitric acid (15M, 3.13 ml) was added to acetic anhydride 12.52 ml) at 0° C. and the mixture stirred for 15 minutes, then added to a stirred solution of methyl 4-[3-(2-hydroxyphenyl)-propyl]benzoate (12.89 g) in acetic anhydride (300 ml) at 0° C. and stirred for 18 hours. The solvent was evaporated and the resulting yellow oil purified by chromatography on silica gel using ethyl acetate: hexane (1:9 to 1:1 gradient) as eluant to give methyl 4-[3-(2-hydroxy-3-nitrophenyl)propyl]benzoate (5.4 g) and methyl 4-[3-(2-hydroxy-5-nitrophenyl)propyl]benzoate (7.5 g).

d:- Methyl 4-[3-(2-benzyloxy-5-aminophenyl)propyl]benzoate was prepared from methyl 4-[3-(2-benzyloxy-5-nitrophenyl)propyl]benzoate using the process described in Example 2, note a.

e:- Methyl 4-[3-(2-benzyloxy-5-methylcarbonylaminophenyl)propyl]benzoate was prepared from methyl 4-[3-(2-benzyloxy-5-aminophenyl)-propyl]benzoate by the method described in Example 2, note b.

f:- Methyl 4-[3-(2-benzyloxy-5-ethoxycarbonylaminophenyl)propyl]benzoate was prepared from methyl 4-[3-(2-benzyloxy-5-aminophenyl)-propyl]benzoate by the method described in Example 2, note b using ethyl chloroformate in the place of acetic anhydride as the acylating agent.

g:- Methyl 4-[3-(2-benzyloxy-5-phenylsulphonamidophenyl)propyl]benzoate was prepared from methyl 4-[3-(2-benzyloxy-5-aminophenyl)-propyl] benzoate as follows:

To a mixture of methyl 4-[3-(2-benzyloxy-5-aminophenyl)-propyl]benzoate (0.3 g) and potassium carbonate (170 mg) was added benzenesulphonyl chloride (0.15 ml) and the mixture stirred for 18 hours, poured into ethyl acetate (50 ml) and washed with 1M HCl (50 ml), sodium bicarbonate (50 ml) and brine (50 ml). The organic solution was dried (magnesium sulphate), filtered and evaporated. The residue was purified by subjecting to chromatography on silica gel using ethyl acetate: hexane (3:7) as eluant. There was thus obtained methyl 4-(3-(2-benzyloxy-5-phenylsulphonamidophenyl)propyl)benzoate (150 mg).

h:- Methyl 4-[3-(2-benzyloxy-5-(trifluoromethylcarbonylamino)-phenyl)propyl]benzoate was synthesised from methyl 4-[3-(2-benzyloxy-5-aminophenyl)propyl]benzoate using the method described in Example 2, note b using trifluoromethylacetic anhydride in the place of acetic anhydride as the acylating agent.

To a mixture of NaH (50% by weight in oil) (20 mg) in DMF (5 ml) was added methyl 4-[3-(2-benzyloxy-5-(trifluoromethylcarbonylamino)phenyl)propyl]benzoate (200 mg). After 1 hour, MeI (0.2 ml) was added and the mixture stirred for 18 hours. The mixture was poured into 1M HCl (50 ml), and extracted with ethyl acetate (2×25 ml). The organics were washed with brine (50 ml), dried (magnesium sulphate), filtered and evaporated. There was thus obtained methyl 4-[3-(2-benzyloxy-5-(N-methyl-trifluoromethylcarbonylamino)phenyl)-propyl]benzoate (200 mg).

4-[3-(2-Benzyloxy-5-methylaminophenyl)propyl]benzoic acid was obtained from methyl 4-[3-(2-benzyloxy-5-(N-methyltrifluoromethylcarbonylamino)phenyl)propyl) benzoate by the standard hydrolysis method.

i:- Methyl 4-[3-(2-benzyloxy-5-(N,N-diethylamino)phenyl) propyl]-benzoate was obtained from methyl 4-[3-(2-benzyloxy-5-aminophenyl)-propyl]benzoate as follows:

To a mixture of methyl 4-(3-(2-benzyloxy-5-aminophenyl)-propyl]benzoate (250 mg) in DMF (10 ml) was added potassium carbonate (200 mg) and ethyl iodide (0.16 ml). The mixture was stirred for 18 hours, poured into ethyl acetate (50 ml) and washed with brine (50 ml), dried (magnesium sulphate), filtered and evaporated. The residue was purified by chromatography on silica gel using ethyl acetate: hexane (3;7) as eluant. There was thus obtained methyl 4-[3-(2-benzyloxy-5-(N,N-diethylamino)phenyl) propyl)benzoate (150 mg).

j:- Methyl 4-[3-(2-hydroxy-5-acetylphenyl)propyl]benzoate was obtained from methyl 4-[3-(2-hydroxyphenyl)propyl] benzoate as follows:

To a cooled (0° C.) solution of aluminium chloride (311 mg) in nitrobenzene (5 ml) was added methyl 4-[3-(2- hydroxyphenyl)propyl]-benzoate (0.6 g) then acetyl chloride (0.16 ml). The mixture was heated at 50° C. for 3 hours, aluminium chloride (622 mg) added and the mixture was heated at 50° C. for a further 3 hours. The mixture was poured into 1M HCl (100 ml) and ethyl acetate (100 ml), the organic layer washed with sodium bicarbonate (100 ml) and brine (100 ml), dried (magnesium sulphate), filtered and evaporated. The residue was purified by subjecting to chromatography on silica gel using ethyl acetate: dichloromethane (0:100, 5:95 gradient) as eluant. There was thus obtained methyl 4-[3-2-hydroxy-5-acetylphenyl)propyl] benzoate (360 mg).

k:- Methyl 4-[3-(2-hydroxy-5-hexanoylphenyl)propyl] benzoate was obtained from methyl 4-(3-(2-hydroxyphenyl) propyl]benzoate by the method described in note j using hexanoyl chloride in place of acetyl chloride.

l:- Methyl 4-[3-(2-benzyloxy-5-hexylphenyl)propyl] benzoate was obtained from methyl 4-[3-2-benzyloxy-5-hexanoylphenyl)propyl]-benzoate (synthesised from methyl 4-[3-(2-hydroxy-5-hexanoylphenyl)-propyl]benzoate using the benzylation method described in Example 1 B) as follows:

To a solution of methyl 4-[3-(2-benzyloxy-5-hexanoylphenyl)-propyl]benzoate (280 mg) in trifluoroacetic acid (0.47 ml) was added triethylsilane (0.49 ml) and the mixture stirred for 18 hours. Trifluoroacetic acid (0.47 ml) and triethylsilane (0.49 ml) were added and the mixture stirred for a further 4 hours. The reaction mixture was purified by subjecting to chromatography on silica gel using dichloromethane as eluant. There was thus obtained methyl 4-[3-(2-benzyloxy-5-hexylphenyl)propyl]benzoate (210 mg).

m:- Methyl 4-[3-(2-hydroxy-5-bromophenyl)propyl] benzoate was obtained from methyl 4-[3-(2-hydroxyphenyl) propyl]benzoate as follows:

To a mixture of methyl 4-[3-(2-hydroxyphenyl)propyl] benzoate (1.5 g) in chloroform (25 ml) was added tetrabutylammonium tribromide (3.12 g). The mixture was stirred for 2 hours, washed with sodium thiosulphate (100 ml), and water (3×100 ml), dried (magnesium sulphate), filtered and evaporated. The residue was purified by chromatography on silica gel using ethyl acetate:hexane (3:7) as eluant. There was thus obtained methy 4-[3-(2-hydroxy-5-bromophenyl)-propyl]benzoate (1.9 g).

n:- Methyl 4-[3-(2-benzyloxy-5-cyanophenyl)propyl] benzoate was obtained from methyl 4-[3-(2-benzyloxy-5-bromophenyl)propyl]-benzoate as follows:

A mixture of methyl 4-[3-(2-benzyloxy-5-bromophenyl) propyl]-benzoate (0.5 g) and CuCN (250 mg) in DMF (20 ml) was heated at reflux for 18 hours, poured into ethylene diamine (20 ml) and water (60 ml) and extracted with ethyl acetate (3×100 ml). The combined extracts were washed with brine (100 ml), dried (magnesium sulphate), filtered and evaporated to give methyl 4-[3-(2-benzyloxy-5-cyanophenyl)propyl]-benzoate (290 mg).

o:- Methyl 4-(3-(2-hydroxy-5-formylphenyl)propyl] benzoate was obtained from methyl 4-[3-(2-hydroxyphenyl) propyl]benzoate as follows:

To a mixture of methyl 4-[3-(2-hydroxyphenyl)propyl]-benzoate in dichloromethane (12 g) at −5° C. was added titanium tetrachloride (1 M solution in dichloromethane, 97.8 ml) then 1,1-dichloromethyl methylether (4.83 ml) in dichloromethane (50 ml). The mixture was stirred for 2 hours at −5° C. then 3 hours at ambient temperature, poured into ice and concentrated HCl (2 ml) was added. The mixture was stirred with diethyl ether (200 ml) for 30 minutes, the layers separated and the aqueous layer extracted with ethyl acetate (3×200 ml). The combined organic solutions were dried (magnesium sulphate), filtered and evaporated. The residue was purified by chromatography on silica gel using ethyl acetate: dichloromethane (0:100 to 10:90 gradient) as eluant. Two products were isolated, methyl 4-[3-(2-hydroxy-3-formylphenyl)propyl]- benzoate (2.40 g) eluted first, and methyl 4-[3-(2-hydroxy-5-formyl-phenyl) propyl]benzoate (6.39 g) eluted second.

p:- Methyl 4-[3-(2-benzyloxy-5-hydroxymethylphenyl) propyl]-benzoate was obtained from methyl 4-[3-(2-benzyloxy-5-formylphenyl)-propyl]benzoate as follows:

A mixture of methyl 4-[3-(2-benzyloxy-5-formylphenyl) -propyl]benzoate (0.97 g) and sodium borohydride (142 mg) in ethanol (10 ml) was stirred at 0° C. for 30 minutes at ambient temperature for 1 hour, the solvent was evaporated, the residue mixed with ethyl acetate (100 ml) and washed with 1M HCl (100 ml), sodium bicarbonate (100 ml) and brine (100 ml), dried (magnesium sulphate), filtered and evaporated. The residue was purified by subjecting to chromatography on silica gel using ethyl acetate: dichloromethane (0:100 to 5:95 gradient) as eluant. There was thus obtained methyl 4-[3-( 2-benzyloxy-5-hydroxymethylphenyl)propyl]benzoate (0.94 g)

q:- Methyl 4-[3-(2-benzyloxy-5-(acetyloxime phenyl) propyl]-benzoate was obtained from methyl 4-[3-(2-benzyloxy-5-acetylphenyl)-propyl]benzoate propyl] benzoate as follows:

A mixture of methyl 4-[3-(2-benzyloxy-5-acetylphenyl)-propyl]benzoate (402 mg) and hydroxylamine hydrochloride (139 mg) in pyridine (5 ml) was heated at 60° C. for 2 hours, evaporated and the residue was purified by subjecting to chromatography on silica gel using ethyl acetate: dichloromethane (5:95) as eluant. There was thus obtained methyl 4-[3-(2-benzyloxy-5-(acetyloxime)phenyl)-propyl]benzoate (0.38 g).

r:- Methyl 4-[3-(2-benzyloxy-5-(formyloxime)phenyl) propyl]-benzoate was obtained from methyl 4-[3-(2-benzyloxy-5-formylphenyl)-propyl]benzoate by a similar method to that described in note q.

s:- Methyl 4-[3-(2-benzyloxy-5-(O-methylacetyloxime) phenyl)-propyl]benzoate was obtained from methyl 4-[-(2-benzyloxy-5-(acetyloxime)-phenyl)propyl]benzoate as follows:

A mixture of methyl 4-[3-(2-benzyloxy-5-5acetyloxime) -phenyl)propyl]benzoate (390 mg) and NaH (50% by weight in oil) (60 mg) was stirred for 30 minutes. MeI (0.23 ml) was added and the mixture stirred for 2 hours. A further 100 mg of NaH (50% by weight in oil) and 1 ml of MeI was added and the mixture stirred for 18 hours, poured into 1M HCl (100 ml) and extracted with ethyl acetate (100 ml) and the solvent evaporated. The residue was purified by chromatography on silica gel using dichloromethane: hexane (0:100 to 80:20 gradient) as eluant. There was thus obtained methyl4-[3-(2-benzyloxy-5-(acetyloxime)pheny)propyl] benzoate (150 mg).

t:- Methyl 4-[2-(2-hydroxy-5-nitrophenyl)ethyl]benzoate was prepared from methyl 4-[3-(2-hydroxyphenyl)ethyl] benzoate by a similar method to that described in note c.

u:- Methyl 4-[3-(2-benzyloxy-5-methanesulphinyl)phenyl) propyl]benzoate was obtained from the corresponding methylthio compound (see example 7) by a modification of the method in example 49 in which mCPBA was added at 0° C. and the reaction terminated when all the methylthio compound was consumed.

v:- Methyl 4-[3-(2-benzyloxy-5-methanesulphonylphenyl) propyl]benzoate ester was obtained from the corresponding methylthio compound (see example 7) by a similar method to that of Example 49.

w:- The ethyl ester was obtained using a similar method to that described in Example 45 (compound 51).

x:- The ethyl ester was obtained using a similar method to that described in Example 45 (compound 52).

y:- Methyl 4-[3-(2-hydroxy-5,6,7,8-tetrahydro-1-naphthyl) propyl]benzoate was obtained as a by-product from the reduction of methyl 4-[3-(2-benzyloxy- -naphthyl)-2-propenyl]benzoate and methyl 4-[3-(2-benzyloxy-1-naphthyl)-1-propenyl]benzoate (mixture of double bond isomers) obtained as an intermediate to compound 34 (Example 3).

z:- Methyl 4-[3-(2-hydroxy-5-(2-methylpropionyl)phenyl) propyl]benzoate was obtained from methyl 4-[3-(2-hydroxyphenyl) propyl]benzoate using and 2-methylpropionyl chloride using the method described in Example 3 Footnote j.

aa:- The methyl 4-[3-(2-benzyloxy-5-hydroxyiminoalkylphenyl) propyl]-benzoates were obtained from the corresponding methyl 4-[3-(2-benzyloxy-5-alkanoylphenyl)propyl]benzoate compounds by a similar method to that of Example 3, Footnote q, as a mixture of the Z and E isomers.

ab:- Methyl 4-[3-(2-hydroxy-5-propionylphenyl)propyl] benzoate was obtained from methyl 4-[3-(2-hydroxyphenyl) propyl]benzoate and EtCOCl using a similar method to that of Example 3, Footnote j.

ac:- Methyl 4-[3-(2-hydroxy-5-benzoylphenyl)propyl] benzoate was obtained from methyl 4-[3-(2-hydroxyphenyl) propyl]benzoate and PhCOCl using a similar method to that of Example 3, Footnote j.

ad:- Methyl 4-[3-(2-benzyloxy-5-(1-semicarbazonoethyl) phenyl)propyl]benzoate (mpt. 158°-160° C.) was obtained as follows:—
A mixture of methyl 4-[3-(2-benzyloxy-5-acetylphenyl) propyl]benzoate (0.5 g), NH$_2$CONHNH$_2$. HCl 0.14 g) and pyridine (5 drops) in methanol (20 ml) was heated under reflux for 90 minutes, cooled and the resulting white solid isolated by filtration and washed with ethanol and ether.

ae:- Methyl 4-[3-(2-benzyloxy-5-(1-hydrazonoethyl) phenyl) propyl]benzoate was obtained as follows:—
A mixture of methyl 4-[3-(2-benzyloxy-5-acetylphenyl) propyl]benzoate (0.5 g) and hydrazine hydrate (1.2 ml) in ethanol (20 ml) was heated at reflux in a soxhlet apparatus using Na$_2$SO$_4$ as the drying agent, for 3 hours. The solvent was evaporated and the residue extracted with EtOAc and washed with saturated aqueous NaHCO$_3$ solution.

af:- Methyl 4-[3-(2-benzyloxy-5-(1-phenylhydrazonoethyl) phenyl)propyl]benzoate was obtained using a similar method to that of Example 3 Footnote ae, with the modification that 3 drops of glacial acetic acid were added to the reaction mixture.

ag:- Methyl 4-[3-(2-benzyloxy-5-methoxymethylphenyl) propyl]benzoate was obtained as follows:—
To a solution of methyl 4-[3-(2-benzyloxy-5-hydroxymethylphenyl) propyl]benzoate (5.31 g) in methanol (100 ml) was added 4-methylbenzenesulphonic acid (3.11 g). The reaction was heated at reflux for 18 hours, the solvent evaporated, the residue dissolved in EtOAc, washed with brine and the solvent evaporated to give methyl 4-[3-(2-benzyloxy-5-methoxymethylphenyl)propyl]benzoate (3.64 g).

ah:- To a stirred solution of methyl 4-[3-(2-benzyloxy-5-hydroxymethylphenyl)propyl]benzoate (1.57 g) in CH$_2$Cl$_2$ (15 ml), at −20° C., was added methanesulphonyl chloride (0.37 ml), triethylamine (0.84 ml) and DMAP (0.29 g) . The reaction was stirred at −20° C. for 5 hours, diluted with CH$_2$Cl$_2$ (50 ml) and washed with water, saturated aqueous NaHCO$_3$ and brine. The organic layer was dried (MgSO$_4$), filtered and evaporated to give a white solid (1.37 g). To the white solid (1.37 g) in DMF (10 ml) was added sodium thiomethoxide (0.24 g) in DMF (10 ml). The reaction mixture was stirred for 8 hours, the solvent evaporated and the residue washed with water and extracted with ethyl acetate. The organic solution was washed with brine, dried (MgSO$_4$), filtered and evaporated, to give methyl 4-[3-(2-benzyloxy-5-methanethiomethylphenyl)propyl]benzoate (0.68 g) which crystallised on standing.

ai:- 4ethyl 4-[3-(2-benzyloxy-5-methanesulphinylmethylphenyl) propyl]benzoate and methyl 4-[3-(2-benzyloxy-5-methanesulphonylmethylphenyl)propyl]benzoate were prepared as a mixture from the methyl 4-[3-(2-benzyloxy-5-methanethiomethylphenyl) propyl]benzoate using a similar method to that of Example 49 and separated by MPLC, eluting with ethyl acetate.

aj:- Methyl 4-[3-(2-benzyloxy-5-(oxazol-5-yl)phenyl] benzoate was prepared as follows:-
To a mixture of methyl 4-[3-(2-benzyloxy-5-formylphenyl) propyl]benzoate (0.75 g) and potassium carbonate (0.696 g) in methanol (60 ml) was added tosylmethyl isocyanide (0.54 g). The reaction was heated at reflux for 30 minutes, the solvent evaporated and the residue partitioned between water and CH$_2$Cl$_2$. The CH$_2$Cl$_2$ was washed with H$_2$O, dried (MgSO$_4$), filtered and evaporated. The residue was purified by MPLC, eluting with 3% EtOAc/CH$_2$Cl$_2$ to give methyl 4-[3-(2-benzyloxy-5-(oxazol-5-yl)phenyl]benzoate (290 mg).

ak:- Methyl 4-[3-(2-benzyloxy-5-(diethylamino)phenyl) propyl]benzoate was prepared as follows:-
To a mixture of methyl 4-[3-(2-benzyloxy-5-aminophenyl) propyl]benzoate (250 mg) in DMF (5 ml) was added potassium carbonate (0.2 g) and iodoethane (0.16 ml). The reaction was stirred for 18 hours, diluted with EtOAc, washed with water and brine, dried (MgSO$_4$), filtered and evaporated. The residue was purified by flash chromatography to give the methyl 4-[3-(2-benzyloxy-5-(diethylamino) phenyl)propyl]benzoate as an oil (150 mg).

al:- Methyl 4-[2-(2-benzyloxy-5-bromophenyl)ethyl) benzoate was prepared from methyl 4-[2-(2-hydroxyphenyl) ethyl]benzoate using a similar method to that of Example 3 Footnote m.

EXAMPLE 4

4-[3-(2-Benzyloxy-5-hydroxyphenyl)propyl]benzoic acid (A) A mixture of benzyl 4-[3-(2-benzyloxy-5-(t-butylcarbonyloxyphenyl)propyl]benzoate and 2M NaOH (8 ml) in ethanol (20 ml) was stirred for 18 hours, a further 4 ml of 2 M NaOH was added and the reaction stirred for 3 hours. The solvent was evaporated, and the residue mixed with 1M HCl and extracted with ethyl acetate (100 ml). The solvent was evaporated and the residue was purified by chromatography on silica gel using ethyl acetate hexane (1;1) then methanol as eluant. There was thus obtained 4-(3-(2-benzyloxy-5-hydroxyphenyl)propyl]benzoic acid (700 mg) mp. 170°-171° C.

Benzyl 4-[3-(2-benzyloxy-5-(t-butylcarbonyloxy)phenyl) -propyl]benzoate was prepared as follows:
(B) To a mixture of 2,5-dihydroxybenzaldehyde (10 g) in dichloromethane (50 ml) at 0° C. was added triethylamine (5 ml) and pivaloyl chloride (4.4 ml). The mixture was stirred at room temperature for 18 hours, filtered and the filtrates washed with 2M HCl (100 ml), brine (100 ml) and sodium bicarbonate (100 m), dried (magnesium sulphate) filtered and evaporated. The residue was purified by chromatography on silica gel using dichloromethane:hexane (0:1 to 1:1 gradient) then ethyl acetate:hexane (1:9 to 3:7 gradient) as eluants to give 2-hydroxy-5-(t-butylcarbonyloxy) benzaldehyde (4 g) and some 2,5-dihydroxy-benzaldehyde.

(C) To a mixture of (4-carboxyphenyl)ethyl triphenylphosphonium bromide (see Example 3, note a) (6.04 g) in THF was added lithium hexamethyldisilazide (38 ml, 1.0M solution in THF). The mixture was stirred for 1 hour, and 2-hydroxy-5-(t-butylcarbonyloxy)benzaldehyde (2.6 g) was added, the mixture stirred for 18 hours, poured into 1M HCl (200ml) and extracted with ethyl acetate (3×100 ml). The combined organics were washed with brine (100 ml), dried (magnesium sulphate) filtered and evaporated. The residue was purified by chromatography on silica gel using ethyl acetate:hexane (1:9 to 8:2 gradient) as eluant. This material (3 g) was mixed with ethanol (300 ml) and 10% Pd-carbon (0.5 g) and stirred under 1 atm. of hydrogen for 18 hours. The mixture was filtered and the filtrate evaporated. There was thus obtained 4-[3-(2-hydroxy-5-(t-butylcarbonyloxy)phenyl)propyl]benzoic acid (3 g).

(D) To a mixture of 4-[3-(2-hydroxy-5-(t-butylcarbonyloxy)phenyl)propyl]benzoic acid (3 g) and potassium carbonate (3.5 g) in DMF (10 ml) was added benzyl bromide (2.97 ml). The mixture was stirred for 18 hours, poured into ethyl acetate (100 ml) and water (100 ml). The organic solution was washed with brine (100 ml), dried (magnesium sulphate) filtered and evaporated. The residue was purified by subjecting to chromatography on silica gel using ethyl acetate:hexane (1:9) as eluant. There was thus obtained benzyl 4-[3-(2-benzyloxy-5-(t-butylcarbonyloxy) phenyl)propyl]benzoate (2 g)

EXAMPLE 5
4-[3-(2-Benzyloxy-5-allyloxyphenyl)propyl]benzoic acid (A) Allyl 4-[3-(2-benzyloxy-5-(allyloxy)phenyl)-propyl] benzoate was converted to 4-[3-(2-benzyloxy-5-(allyl-oxy) phenyl)propyl]benzoic acid mp. 96°-97° C., using the method described in Example 4 for the conversion of benzyl 4-[3-(2-benzyloxy-5-(t-butylcarbonyloxy)phenyl)propyl] benzoate to 4-[3-(2-benzyloxy-5-hydroxyphenyl)propyl] benzoic acid.

Allyl 4-[3-(2-benzyloxy-5-(allyloxy)phenyl)propyl] benzoate was prepared as follows:

(B) To a mixture of 4-[3-(2-benzyloxy-5-hydroxyphenyl) propyl]- benzoic acid (150 mg) (prepared as described in Example 4) and potassium carbonate (125 mg) in DMF (5 ml) was added allyl bromide (0.076 ml). The mixture was stirred for 18 hours, then potassium carbonate (125 mg) and allyl bromide (0.076 ml) were added and the mixture stirred for a further 18 hours. The mixture was poured into water (50 ml) and extracted with ethyl acetate (2×20 ml). The combined organics solutions were washed with brine (25 ml) and sodium bicarbonate (25 ml), dried (magnesium sulphate) filtered and evaporated. There was thus obtained allyl 4-[3-(2-benzyloxy-5-(allyloxy)phenyl)propyl]benzoate (150 mg).

EXAMPLE 6
4-[3-(2-Benzyloxy-5-carbamoylmethoxyphenyl)propyl] benzoic acid (A) Methyl 4-[3-(2-benzyloxy-5-(carbamoylmethoxy) phenyl)propyl] benzoate was converted to 4-[3-(2-benzyloxy-5-(carboxymethoxy)phenyl)propyl]benzoic acid mp. 156°-157° C., using the method described in Example 4 for the conversion of benzyl 4-[3-(2-benzyloxy-5-(t-butylcarbonyloxy)phenyl)propyl]benzoate to 4-[3-(2-benzyloxy-5-hydroxyphenyl)propyl]benzoic acid.

Methyl 4-[3-(2-benzyloxy-5-(carbamoylmethoxy) phenyl)-propyl] benzoate was prepared from 4-[3-(2-benzyloxy-5-hydroxy-phenyl)propyl]benzoic acid (Example 4) as follows:

(B) To a mixture of 4-[3-(2-benzyloxy-5-hydroxyphenyl) propyl]-benzoic acid (225 mg) in methanol (25 ml) at 0° C. was added dropwise thionyl chloride (0.05 ml). The mixture was stirred for 18 hours, and a further 0.05 ml of thionyl chloride was added. After 4 hours the solvent was evaporated and the residue dissolved in ethyl acetate (100 ml) and washed with sodium bicarbonate (25 ml) and brine (25 ml), dried (magnesium sulphate) filtered and evaporated. There was thus obtained methyl 4-[3-(2-benzyloxy-5-hydroxyphenyl)propyl]benzoate (250 mg).

(C) To a mixture of methyl 4-[3-(2-benzyloxy-5-hydroxyphenyl)propyl]benzoate (510 mg) and potassium carbonate in DMF (10 ml) was added bromoacetamide (384 mg). The reaction was stirred for 48 hours, poured into ethyl acetate (50 ml), washed with 1M HCl (50 ml) and brine (50 ml), dried (magnesium sulphate) filtered and evaporated. The residue was purified by subjecting to chromatography on silica gel using ethyl acetate:hexane (75:25) as eluant. There was thus obtained methyl 4-[3-(2-benzyloxy-5-(carbamoylmethoxy)phenyl)propyl]benzoate (200 mg).

EXAMPLE 7
4-[3-(2-Benzyloxy-5-methylthiophenyl)]benzoic acid (A) Methyl 4-[3-(2-benzyloxy-5-methylthiophenyl)-propyl]benzoate was converted to 4-[3-(2-benzyloxy-5-methylthiophenyl)propyl]benzoic acid mp.: 110°-112° C., using the method described in Example 1 for the conversion of methyl 4-[3-(2-benzyloxyphenyl)propyl]benzoate to 4-[3-(2-benzyloxyphenyl)-propyl]benzoic acid except that the product was purified by crystallisation from methanol instead of chromatography.

Methyl 4-[3-(2-benzyloxy-5-methylthiophenyl)propyl] benzoate was prepared from 4-methylmercaptophenol as follows:

(B) To a mixture of 4-methylmercaptophenol (50 g) in trifluoroacetic acid (260 ml) was added hexamine (50 g) in small portions at below 50° C. The mixture was heated at 100° C. for 2 hours, cooled and 50% sulphuric acid (1 l) was added. The mixture was stirred for 1 hour, extracted with diethyl ether (4×200 ml), the combined extracts dried (magnesium sulphate) and evaporated. The residue was purified by subjecting to chromatography on silica gel using dichloromethane:hexane (3:2) as eluant. There was thus obtained 5-methylthio-2-hydroxybenzaldehyde (5.2 g).

(C) A mixture of 5-methylthio-2-hydroxybenzaldehyde (5.2 g), benzyl bromide (5.3 g), potassium carbonate (12.8 g) in acetone was heated at reflux for 4 hours, cooled, filtered and evaporated. The residue was purified by subjecting to chromatography on silica gel using dichloromethane:hexane (7:3) as eluant. There was thus obtained 5-methylthio-2-benzyloxybenzaldehyde (5.2 g).

(D) 5-Methylthio-2-benzyloxybenzaldehyde was converted to methyl 4-[3-(2-benzyloxy-5-methylthiophenyl) propenyl]benzoate (as a mixture of double bond isomers) by the first 2 stages of the method described in Example 1 as the second alternative method to synthesise methyl 4-[3-(2-hydroxyphenyl)propyl]benzoate except that in the second step to form the methyl ester sulphuric acid was used in place of thionyl chloride.

(E) A mixture of methyl 4-[3-(2-benzyloxy-5-methylthiophenyl)propenyl]benzoate (as a mixture of double bond isomers) (3.3 g) and Wilkinson's catalyst (330 mg) was stirred at 50° C. under 50 atm. of hydrogen for 18 hours. The solvent was evaporated and the residue was purified by subjecting to chromatography on silica gel using dichloromethane:hexane (4:1) as eluant. There was thus obtained methyl 4-[3-(2-benzyloxy-5-methylthiophenyl) propyl]benzoate (3.1 g).

EXAMPLE 8

4-[2-Benzyloxyphenethyl]-3-fluorobenzoic acid (A) Methyl 4-[2-(2-benzyloxyphenyl)ethyl)-3-fluorobenzoate was converted to 4-[2-(2-benzyloxyphenyl) ethyl]-3-fluorobenzoic acid mp. 141°-142° C., using the method described in Example 1 for the conversion of methyl 4-[3-(2-benzyloxyphenyl)propyl]benzoate to 4-[3-(2-benzyloxyphenyl)propyl]benzoic acid.

Methyl 4-[2-(2-benzyloxyphenyl)ethyl)-3-fluorobenzoate was prepared as follows:

(B) Methyl 3-fluoro-4-methylbenzoate was prepared from 3-fluoro-4-methylbenzoic acid by the process described in Example 6 for the synthesis of methyl 4-(3-(2-benzyloxy-5-hydroxyphenyl)propyl]-benzoate.

(C) A mixture of methyl 3-fluoro-4-methylbenzoate (4.3 g), N-bromosuccinimide (4.5 g) and AIBN (20 mg) in carbon tetrachloride was irradiated with a 100 W Tungsten lamp at reflux for 1 hour. The mixture was filtered through diatomaceous earth, and evaporated to give methyl 3-fluoro-4-(bromomethyl)benzoate (5.0 g).

(D) A mixture of methyl 3-fluoro-4-(bromomethyl) benzoate (4.0 g) and triphenylphosphine (5.4 g) in toluene (100 ml) was heated at reflux for 18 hours and filtered. The filtered solid was washed with toluene and dried. There was thus obtained (4-carboxymethyl-2-fluorophenyl) methyltriphenylphosphonium bromide (5.6 g).

(E) To a mixture of (4-carboxymethyl-2-fluorophenyl) methyltriphenylphosphonium bromide (5.5 g) in THF (100 ml) at 0° C. was added lithium hexamethyldisilazide (11.9 ml, 1.0M solution in THF). After 1 hour a solution of 2-benzyloxybenzaldehyde (commercially available, or prepared from salicylaldehyde and benzyl bromide using the method described above to synthesise 4-[3-(2-hydroxyphenyl)propyl]benzoate) (4.0 g) in THF (10 ml) was added and the mixture stirred for 2 hours. The mixture was poured into ethyl acetate (100 ml) and 1N HCl (100 ml), the layers separated and the organic solution washed with sodium bicarbonate (100 ml) and brine (100 ml), dried (magnesium sulphate), filtered and evaporated. The residue was purified by chromatography on silica gel using ethyl acetate:hexane (1:9) as eluant. There was thus obtained methyl 4-[2-(2-benzyloxyphenyl)-ethenyl]-3-fluorobenzoate (3.7 g).

(F) Methyl 4-[2-(2-hydroxyphenyl)ethyl]-3-fluorobenzoate was synthesised from methyl 4-(2-(2-benzyloxyphenyl) ethenyl]-3-fluorobenzoate using the hydrogenation method described in Example 1 (for the conversion of 4-[3-(2-benzyloxyphenyl)-3-carbonyl-1(E)-propenyl]-benzoate to methyl 4-[3-(2-hydroxyphenyl)-3-carbonylpropyl)benzoate but using ethanol as the reaction solvent).

(G) Methyl 4-(2-(2-benzyloxyphenyl)ethyl]-3-fluorobenzoate was prepared from methyl 4-[2-(2-hydroxyphenyl)ethyl]-3-fluorobenzoate using the method described in Example 1 for the synthesis of methyl 4-[3-(2-benzyloxyphenyl)propyl]benzoate.

EXAMPLE 9

4-[2-Benzyloxyphenethyl]-3-aminobenzoic acid (A) Methyl 4-[2-(2-benzyloxyphenyl)ethyl]-3-aminobenzoate was converted to 4-[2-(2-benzyloxyphenyl) ethyl]-3-aminobenzoic acid hydrochloride mp. 227°-229° C., using the method described in Example 1 for the conversion of methyl 4-[3-(2-benzyloxyphenyl)propyl] benzoate to 4-[3-(2-benzyloxyphenyl)propyl] benzoic acid except that the residue was purified by washing with 1M HCl and triturating with diethyl ether instead of by subjecting to chromatography.

(B) Methyl 4-[2-(2-benzyloxyphenyl)ethyl]-3-aminobenzoate was prepared as follows:

(C) Methyl 4-[2-(2-benzyloxyphenyl)ethenyl]-3-nitrobenzoate was prepared from 3-nitro-4-methylbenzoic acid using the methods described in Example 8 for the conversion of 3-fluoro-4-methylbenzoic acid to methyl 4-[2-(2-benzyloxyphenyl)ethenyl]-3-fluorobenzoate.

(D) A mixture of methyl 4-[2-(2-benzyloxyphenyl) ethenyl)-3-nitrobenzoate (2.5 g) and 5% Rhodium on alumina (520 mg) in ethanol (200 ml) was stirred under 1 atm. of hydrogen for 20 hours. The mixture was filtered and the solvent evaporated. The residue was purified by subjecting to chromatography using ethylacetate: dichloromethane (9:1) as eluant. There was thus obtained methyl 4-[2-(2-benzyloxyphenyl)ethyl]-3-aminobenzoate (1.71 g).

EXAMPLE 10

4-[2-(2-Benzyloxyphenyl)-(E)-ethenyl]-2-hydroxybenzoic acid (A) Methyl 4-[2-(2-benzyloxyphenyl)-(E)-ethenyl]-2-hydroxybenzoate was converted to 4-[2-(2-benzyloxyphenyl)-(E)-ethenyl]-2-hydroxybenzoic acid mp. 214°-216° C., using the method described in Example 1 for the conversion of methyl 4-[3-(2-benzyloxyphenyl)propyl) benzoate to 4-[3-(2-benzyloxyphenyl)propyl]benzoic acid purifying by crystallisation from dichloromethane/hexane rather than by subjecting to chromatography.

(B) Methyl 4-[2-(2-benzyloxyphenyl)-(E)-ethenyl]-2-hydroxy-benzoate was prepared as follows:

(C) Methyl 2-hydroxy-4-methylbenzoate was prepared from 2-hydroxy-4-methylbenzoic acid by the process described in Example 6 for the synthesis of methyl 4-(3-(2-benzyloxy-5-hydroxyphenyl)propyl]-benzoate.

(D) A mixture of methyl 2-hydroxy-4-methylbenzoate (7.19 g), acetic anhydride (25 ml) and pyridine (25 ml) was stirred for 18 hours, filtered and evaporated. There was thus obtained methyl 2-acetoxy-4-methylbenzoate (9.0 g).

(E) Methyl 2-acetoxy-4-methylbenzoate was converted to a mixture of methyl 4-[2-(2-benzyloxyphenyl)-(E)-ethenyl] -2-hydroxybenzoate and methyl 4-[2-(2-benzyloxyphenyl)-(Z)-ethenyl]-2-hydroxybenzoate using the procedures described in Example 8 for the synthesis of methyl 4-[2-(2-benzyloxyphenyl)ethenyl)-3-fluorobenzoate from methyl 3-fluoro-4-methylbenzoate (using 2 equivalents of lithium hexamethyldisilazide in the final step). The isomers were separated by subjecting to chromatography on silica gel using a dichloromethane:hexane (1:2) as eluant. Further purification of the isomers was achieved by crystallisation.

EXAMPLE 11

4-[2- 2-Benzyloxyphenyl)-(Z)-ethyl]-2-hydroxybenzoic acid (A) Methyl 4-[2-(2-benzyloxyphenyl)-(Z)-ethenyl]-2-hydroxy-benzoate (synthesised as described in Example 12) was converted to 4-[2-2-benzyloxyphenyl)-(Z)-ethenyl]-2-hydroxybenzoic acid mp. 113°-114° C., using the method described in Example 1 for the conversion of methyl 4-[3-(2-benzyloxyphenyl)propyl]benzoate to 4-[3-(2-benzyloxyphenyl)propyl]benzoic acid purifying by crystallisation from diethyl ether/hexane rather than by subjecting to chromatography.

EXAMPLE 12

4-[2-(2-Benzyloxyphenyl)-(E)-ethyenyl]-2-methoxybenzoic acid (A) Methyl 4-[2-(2-benzyloxyphenyl)-(E)-ethenyl]-2-methoxybenzoate was converted to 4-[2-(2-benzyloxyphenyl)-(E)-ethenyl]-2-methoxybenzoic acid mp. 154°-156° C., using the method described in Example 1 for the conversion of methyl 4-[3-(2-benzyloxyphenyl)propyl]benzoate to 4-[3-(2-benzyloxyphenyl)propyl]benzoic acid purifying by crystallisation from dichloromethane/ethyl acetate rather than by subjecting to chromatography.

Methyl 4-[2-(2-benzyloxyphenyl)-(E)-ethenyl]-2-methoxybenzoate was synthesised as follows:

(B) A mixture of methyl 4-[2-(2-benzyloxyphenyl)-(E)-ethenyl]-2-hydroxybenzoate (synthesised as described in Example 10) (0.5 g), methyl iodide (0.5 ml) and potassium carbonate (0.5 g) in DMF (10 ml) was stirred for 18 hours, poured into water (100 ml) and ethyl acetate (100 ml), the layers separated and the organic layer washed with brine and dried (magnesium sulphate). There was thus obtained methyl 4-[2-(2-benzyloxyphenyl)-E-ethenyl]-2-methoxybenzoate (0.52 g).

EXAMPLE 13

4-[2-(2-Benzyloxyphenyl)-(Z)-ethenyl]-2-methoxybenzoic acid (A) Methyl 4-[2-(2-benzyloxyphenyl)-(Z)-ethenyl]-2-methoxy-benzoate (obtained from methyl 4-[2-(2-benzyloxyphenyl)-(Z)-ethenyl]-2-hydroxybenzoate as described in Example 14) was converted to 4-[2-(2-benzyloxyphenyl)-(E)-ethenyl]-2-methoxybenzoic acid (containing 15% of the (Z) isomer and obtained as a gum; negative FAB mass peak 359) using the method described in Example 1 for the conversion of methyl 4-[3-(2-benzyloxyphenyl)propyl]benzoate to 4-[3-(2-benzyloxyphenyl)-propyl]benzoic acid.

EXAMPLE 14

4-[2-Benzyloxyphenethyl]-2-hydroxybenzoic acid (A) Methyl 4-[2-(2-benzyloxyphenyl)ethyl]-2-hydroxybenzoate was converted to 4-[2-(2-benzyloxyphenyl)ethyl]-2-hydroxybenzoic acid mp. 184°-186° C., using the method described in Example 1 for the conversion of methyl 4-[3-(2-benzyloxyphenyl)propyl]benzoate to 4-(3-(2-benzyloxyphenyl)propyl]benzoic acid purifying by crystallisation from diethyl ether/hexane rather than by subjecting to chromatography.

(B) Methyl 4-[2-(2-benzyloxyphenyl)ethyl]-2-hydroxybenzoate was prepared from a Z/E mixture of methyl 4-[2-(2-benzyloxyphenyl)-ethenyl]-2-hydroxybenzoate (prepared as described in Example 10) using the hydrogenation method described in Example 10 for the synthesis of methyl 4-[2-(2-benzyloxyphenyl)ethyl]-3-aminobenzoate.

EXAMPLE 15

4-[2-Benzyloxyphenethyl]-2-methoxybenzoic acid (A) Methyl 4-[2-(2-benzyloxyphenyl)ethyl]-2-methoxybenzoate was converted to 4-[2-(2-benzyloxyphenyl)ethyl]-2-methoxybenzoic acid mp. 124°-125° C., using the method described in Example 1 for the conversion of methyl 4-[3-(2-benzyloxyphenyl)propyl]benzoate to 4-[3-(2-benzyloxyphenyl)propyl]benzoic acid purifying by crystallisation from dichloromethane/hexane rather than by subjecting to chromatography.

(B) Methyl 4-[2-(2-benzyloxyphenyl)ethyl]-2-methoxybenzoate was prepared from methyl 4-[2-(2-benzyloxyphenyl)ethyl]-2-hydroxybenzoate (prepared as described in Example 14) using the method described in Example 14 for the preparation of methyl 4-[2-(2-benzyloxyphenyl)-(E)-ethenyl]-2-methoxybenzoate.

EXAMPLE 16

4-[3-(2-Benzyloxyphenyl)propyl]-2-hydroxybenzoic acid (A) Methyl 4-(3-(2-benzyloxyphenyl)propyl]-2-hydroxybenzoate was converted to 4-(3-(2-benzyloxyphenyl)propyl]-2-hydroxybenzoic acid mp. 130°-131° C., using the method described in Example 1 for the conversion of methyl 4-[3-(2-benzyloxyphenyl)propyl]benzoate to 4-[3-(2-benzyloxyphenyl)propyl]benzoic acid purifying by crystallisation from diethyl ether/hexane rather than by subjecting to chromatography.

Methyl 4-[3-(2-benzyloxyphenyl)propyl]-2-hydroxybenzoate was prepared as follows:

(B) Methyl 4-[3-(2-benzyloxyphenyl)propenyl]-2-hydroxybenzoate (as a mixture of double bond regio and stereoisomers) was prepared by the methods described in Example 12 for the synthesis of the E/Z mixture of methyl 4-[2-(2-benzyloxyphenyl;ethenyl]-2-hydroxybenzoates using (2-benzyloxyphenyl)acetaldehyde in place of 2-benzyloxybenzaldehyde.

(C) Methyl 4-[3-(2-benzyloxyphenyl)propyl]-2-hydroxybenzoate was prepared from methyl 4-[3-(2-benzyloxyphenyl)propenyl]-2-hydroxybenzoate by the method described in Example 9 for the synthesis of methyl 4-[2-(2-benzyloxyphenyl)ethyl]-3-aminobenzoate from methyl 4-[2-(2-benzyloxyphenyl)ethenyl]-3-nitrobenzoate.

EXAMPLE 17

4-[3-(2-Benzyloxyphenyl)propyl]-2-methoxybenzoic acid (A) Methyl 4-[3-(2-benzyloxyphenyl)propyl]2-methoxybenzoate was converted to 4-[3-(2-benzyloxyphenyl)propyl]-2-methoxybenzoic acid mp. 60°-62° C., using the method described in Example 1 for the conversion of methyl 4-[3-(2-benzyloxyphenyl)propyl]benzoate to 4-[3-(2-benzyloxyphenyl)propyl]benzoic acid purifying by crystallisation from diethyl ether/hexane rather than by subjecting to chromatography.

(B) Methyl 4-[3-(2-benzyloxyphenyl)-propyl]-2-methoxybenzoate was synthesised from methyl 4-[3-(2-benzyloxyphenyl)-propyl]-2-hydroxybenzoate (prepared as described in Example 15) as described in Example 14 for the synthesis of methyl 4-[2-(2-benzyloxyphenyl)-(E)-ethenyl]-2-methoxybenzoate from methyl 4-[2-(2-benzyloxyphenyl)-(E)-ethenyl]-2-hydroxybenzoate.

EXAMPLE 18

4-[3-(2-(1-Phenethyloxy)phenyl)propyl]benzoic acid (A) 4-[3-(2-(1-Phenethyloxy)phenyl)propenyl]benzoic acid as a mixture of double bond isomers was hydrogenated under the conditions described in Example 1 (for the conversion of 4-[3-(2-benzyloxyphenyl)-3-carbonyl-1(E)propenyl]benzoate to methyl 4-[3-(2-hydroxyphenyl)-3-carbonylpropyl]benzoate) ensuring that only one equivalent of hydrogen was taken up. There was thus obtained 4-[3-(2-(1-phenethyloxy)phenyl)propyl]benzoic acid mp. 103°-104° C.

4-[3-(2-(1-Phenethyloxy)phenyl)propenyl]benzoic acid was synthesised as follows:

(B) Salicylaldehyde and 1-bromo-1-phenylethane were converted to 2-(1-phenethyloxy)benzaldehyde using the process described in Example 1 for the conversion of 4-[3-(2-hydroxyphenyl)propyl)benzoate to methyl 4-[3-(2-benzyloxyphenyl)propyl]benzoate except that the reaction mixture was heated at 120° C. for 23 hours.

(C) 2-(1-Phenethyloxy)benzaldehyde was converted to 4-[3-(2-(1-phenethyloxy)phenyl)propenyl]benzoic acid (as a mixture of double bond isomers) by the first stage of the method described in Example 1 as the second alternative method to synthesise methyl 4-[3-(2-hydroxyphenyl)propyl]benzoate.

EXAMPLE 19

3-[3-(2-Benzyloxyphenyl)propyl]benzoic acid (A) Methyl 3-[3-(2-benzyloxyphenyl)propyl)benzoate was converted to 3-[3-(2-benzyloxyphenyl)propyl]benzoic acid mp. 88°-90° C., using the method described in Example 1 for the conversion of methyl 4-[3-(2-benzyloxyphenyl)propyl]benzoate to 4-[3-(2-benzyloxyphenyl)propyl]benzoic acid.

Methyl 3-[3-(2-benzyloxyphenyl)propyl]benzoate was prepared as follows:

(B) 1-Allyl-2-benzyloxybenzene was obtained from 2-allylphenol by the benzylation procedure described in Example 1 for the conversion of 4-[3-(2-hydroxyphenyl)propyl]benzoate to methyl 4-[3-(2-benzyloxyphenyl)propyl]benzoate.

(C) A mixture of 1-allyl-2-benzyloxybenzene (0.54 g), methyl 3-iodobenzoate (0.5 g), bistriphenylphosphine palladium dichloride (30 mg) and CuI (4 mg) in degassed triethylamine (25 ml) was heated at 60° C. for 18 hours. The solvent was evaporated and the residue dissolved in dichloromethane and washed with 1M HCl (2×20 ml) and brine (25 ml). The organic solution was evaporated and the residue purified by subjecting to chromatography on silica gel using ethyl acetate:hexane (8:92) as eluant. There was thus obtained methyl 3-[3-(2-benzyloxyphenyl)propenyl)benzoate (0.4 g).

(D) Methyl 3-[3-(2-benzyloxyphenyl)propenyl]benzoate was hydrogenated under the conditions described in Example 1 (for the conversion of 4-(3-(2-benzyloxyphenyl)-3-carbonyl-1(E)-propenyl]-benzoate to methyl 4-[3-(2-hydroxyphenyl)-3-carbonylpropyl)benzoate) using ethanol as the reaction solvent to give methyl 3-[3-(2-hydroxyphenyl)propylibenzoate.

(E) Methyl 3-(3-(2-benzyloxyphenyl)propyl]benzoate was prepared from methyl 3-(3-(2-hydroxyphenyl)propyl] benzoate using the method described in Example 1 for the synthesis of methyl 4-[3-(2-benzyloxyphenyl)propyl)benzoate.

EXAMPLE 20

5-{4-[2(2-Benzyloxyphenyl)ethenyl]phenyl}tetrazole (A) 2-(Pivaloyloxymethyl)-5-{[2-(2-benzyloxyphenyl)ethenyl]-4-phenyl}tetrazole was converted to 5-{4-[2-(2-benzyloxyphenyl)ethenyl]phenyl} tetrazole as a 55:45 mixture of E:Z isomers mp. 176°-177° C., using the method described in Example 1 for the conversion of methyl 4-[3-(2-benzyloxyphenyl)-propyl]benzoate to 4-[3-(2-benzyloxyphenyl)propyl]benzoic acid.

2-(Pivaloyloxymethyl)-5-{[2-(2-benzyloxyphenyl)ethenyl]-4-phenyl}-tetrazole was obtained as follows:

(B) 4-[2-(2-Benzyloxyphenyl)ethenyl]benzonitrile as a mixture of isomers was synthesised from 2-benzyloxybenzaldehyde using the method described in Example 8 for the conversion of 2-benzyloxybenzaldehyde to methyl 4-[2-(2-benzyloxyphenyl)ethenyl]-3-fluorobenzoate using (4-cyanophenyl) methyltriphenylphosphonium bromide in place of (4-methoxycarbonyl-2-fluorophenyl) methyltriphenylphosphonium bromide.

(C) A mixture of 4-[2-(2-benzyloxyphenyl)ethenyl]-benzonitrile as a mixture of isomers (7.88 g) and tri-n-butyltin azide (20.03 ml, 2.53M solution in toluene) in toluene 100 ml was heated at reflux for 66 hours. The mixture was cooled (ice bath) and added dropwise to excess sodium nitrite and stirred for 30 minutes. Sulphamic acid (9 g) was added and the mixture left to stand at 5° C. for 18 hours. The resulting yellow precipitate (9.7 g) was filtered off, dried and mixed with potassium carbonate (7.56 g) in DMF (20 ml) and stirred for 10 minutes. Pivaloyloxymethyl chloride (4.78 ml) was added to the mixture and it was stirred for 18 hours, diluted with ethyl acetate (200 ml), and washed with 1M HCl (100 ml), sodium bicarbonate (100 ml) and brine (100 ml), dried (magnesium sulphate), filtered and evaporated. The residue was purified by subjecting to chromatography on silica gel using methanol : dichloromethane (0:100 to 30:70 gradient) as eluant. There was thus obtained N-2-(pivaloyloxymethyl)-5-{-4-[2-(2-benzyloxyphenyl)ethenyl]-phenyl}tetrazole (7.64 g) and N-1-(pivaloyloxymethyl)-5-{-4-[2-(2-benzyloxyphenyl)ethenyl]-phenyl}tetrazole (1.67 g).

EXAMPLE 21

2-(Pivaloyloxymethyl)-5-{-4-[2-(2-benzyloxyphenyl)-ethyl]phenyl}tetrazole 2-(Pivaloyloxymethyl)-5-{-4-[2-(2-benzyloxyphenyl)-ethenyl]phenyl}tetrazole (synthesised as described in Example 20) was converted to 2-(pivaloyloxymethyl)-5-{-4-[2-(2-benzyloxyphenyl)-ethyl]phenyl}tetrazole by the process described in Example 1 (for the conversion of 4-[3-(2-benzyloxyphenyl)-3-carbonyl-1(E)-propenyl]-benzoate to methyl 4-[3-(2-hydroxyphenyl)-3-carbonylpropyl]benzoate) ensuring that only one equivalent of hydrogen was taken up.

EXAMPLE 22

5-{4-[2-Benzyloxyphenyl)ethyl]-phenyl}tetrazole 2-(Pivaloyloxymethyl)-5-{-4-[2-(2-benzyloxyphenyl)ethyl]-phenyl}tetrazole was converted to 5-{-4-[2-(2-benzyloxyphenyl)ethyl]-phenyl}tetrazole (mp. 223°-225° C.) using the method described in Example 1 for the conversion of methyl 4-(3-(2-benzyloxyphenyl)-propyl]benzoate to 4-[3-(2-benzyloxyphenyl)propyl]benzoic acid.

EXAMPLE 23

5-{-4-[2-(2-Benzyloxy-5-acetylphenyl)ethyl]phenyl}tetrazole (A) 2-(Pivaloyloxymethyl)-5-{-4-[2-(2-benzyloxy-5-acetylphenyl)ethyl]phenyl}tetrazole was converted to 5-{-4-[2-(2-benzyloxy-5-acetylphenyl)ethyl]phenyl}tetrazole mp. 193°-195° C., using the method described in Example 1 for the conversion of methyl 4-[3-(2-benzyloxyphenyl)propyl]benzoate to 4-[3-(2-benzyloxyphenyl)propyl)-benzoic acid.

2-(Pivaloyloxymethyl)-5-{-4-[2-(2-benzyloxy-5-acetylphenyl)ethyl]phenyl}tetrazole was obtained as follows:

(B) 2-(Pivaloyloxymethyl)-5-{-4-[2-(2-benzyloxyphenyl)-ethenyl]phenyl}tetrazole (obtained as described in Example 20) was converted to 2-(pivaloyloxymethyl)-5-{-4-[2-(2-hydroxyphenyl)-ethyl]phenyl}tetrazole by the process described in Example 1 (for the conversion of 4-[3-(2-benzyloxyphenyl)-3-carbonyl-1(E)-propenyl]-benzoate to methyl 4-[3-(2-hydroxyphenyl)-3-carbonylpropyl]benzoate)

(C) 2-(Pivaloyloxymethyl)-5-{-4-[2-(2-hydroxyphenyl) ethyl]-phenyl}tetrazole was converted to 2-(pivaloyloxymethyl)-5-{-4-[2-(2-hydroxy-5-acetylphenyl)ethyl]phenyl}tetrazole by the method described in example 3, footnote j, for the conversion of methyl 4-]3-(2-hydroxyphenyl)propyl]benzoate to methyl 4-(3-(2-hydroxy-5-acetylphenyl)propyl]benzoate.

(D) 2-(Pivaloyloxymethyl)-5-{-4-[2-(2-hydroxy-5-acetylphenyl)ethyl]phenyl}tetrazole was converted to N-2-(pivaloyloxymethyl)-5-{-4--2-(2-benzyloxy-5-acetylphenyl) ethyl]phenyl}tetrazole by the process described in Example 1 for the conversion of 4-[3-(2-hydroxyphenyl)propyl]benzoate to methyl 4-[3-(2-benzyloxyphenyl)propyl]benzoate.

EXAMPLE 24

5-{4-[2-(2-Benzyloxy-5-bromo-phenyl)ethyl]phenyl}tetrazole (A) 2-(Pivaloyloxymethyl)-5-{(-4-[2-(2-benzyloxy-5-bromophenyl)ethyl]phenyl}tetrazole was converted to 5-{-4-[2-(2-benzyloxy-5-bromophenyl)ethyl]phenyl}tetrazole mp. 256°-258° C., using the method described in Example 1 for the conversion of methyl 4-[3-(2-benzyloxyphenyl)propyl]benzoate to 4-[3-(2-benzyloxyphenyl)-propyl]benzoic acid.

2-(Pivaloyloxymethyl)-5-{-4-[2-(2-benzyloxy-5-bromophenyl)-ethyl]phenyl}-tetrazole was obtained as follows:

(B) 2-(Pivaloyloxymethyl)-5-{-4-[2-(2-hydroxyphenyl)ethyl]-phenyl}tetrazole (prepared as described in Example 23) was converted to N-2-(pivaloyloxymethyl)-5-{-4-[2-(2-hydroxy-5-bromophenyl)ethyl]-phenyl}tetrazole by the method described in example 3, footnote m, for the conversion of methyl 4-[3-(2-hydroxyphenyl)propyl]benzoate to methyl 4-[3-(2-hydroxy-5-bromophenyl)propyl]benzoate.

(C) 2-(Pivaloyloxymethyl)-5-{-4-[2-(2-hydroxy-5-bromophenyl)ethyl]phenyl tetrazole was converted to N-2-(pivaloyloxymethyl)-5-{-4-[2-(2-benzyloxy-5-bromophenyl)ethyl]-phenyl}tetrazole by the process described in Example 1 for the conversion of 4-[3-(2-hydroxyphenyl)propyl]benzoate to methyl 4-[3-(2-benzyloxyphenyl)propyl]benzoate.

EXAMPLE 25

5-{-4-[3-(2-Benzyloxyphenyl)-propyl]phenyl}tetrazole (A) 2-(Pivaloyloxymethyl)-5-{-4-[3-(2-benzyloxyphenyl)-propyl]phenyl}tetrazole was converted to 5-{-4-[3-(2-benzyloxyphenyl)-propyl3phenyl}tetrazole mp. 185.5°-186.5° C. using the method described in Example 1 for the conversion of methyl 4-[3-(2-benzyloxyphenyl)-propyl]benzoate to 4-[3-(2-benzyloxyphenyl)propyl]benzoic acid.

2-(Pivaloyloxymethyl)-5-{-4-[3-(2-benzyloxyphenyl)propyl]-phenyl}tetrazole was obtained-as follows:

(B) To a mixture of 2-(4-cyanophenyl)ethanol (5 g) in diethyl ether was added phosphorus tribromide (3.94 ml) dropwise. The mixture was heated at reflux for 3 hours, poured into water (200 ml) and the organic layer washed with sodium bicarbonate (100 ml) and brine (100 ml), dried (magnesium sulphate), filtered and evaporated. There was thus obtained (4-cyanophenethyl)bromide (3.34 g).

(C) A mixture of (4-cyanophenethyl)bromide (3.24 g) and triphenylphosphine (8.06 g) in toluene was heated at reflux for 72 hours. The suspension was filtered off and washed with toluene. The resulting solid was triturated with diethyl ether. There was thus obtained 2-(4-cyanophenyl)ethyltriphenylphosphonium bromide (5.7 g).

(D) 2-(4-Cyanophenyl)ethyltriphenylphosphonium bromide was converted to 2-(4-tetrazol-5-ylphenyl)ethyltriphenylphosphonium chloride using the method described in Example 20 for the conversion of 4-[2-(2-benzyloxyphenyl)ethenyl]benzonitrile to crude 5-{-4-[2-(2-benzyloxyphenyl)ethenyl]phenyl}tetrazole.

(E) 2-(4-Tetrazol-5-ylphenyl)ethyltriphenylphosphonium chloride and 2-benzyloxybenzaldehyde were converted to 5-{-4- (3-(2-benzyloxyphenyl)propenyl]phenyl}tetrazole as a mixture of double bond isomers using the first stage of the method described in Example 1 as the second alternative method to synthesise methyl 4-[3-(2-hydroxyphenyl)propyl]benzoate.

(F) 5-{-4-[3-(2-Benzyloxyphenyl)propenyl]phenyl}tetrazole as a mixture of double bond isomers was converted to 2-(pivaloyloxymethyl)-5-{-4-[3-(2-benzyloxyphenyl)propenyl]phenyl}-tetrazole by the method described in Example 19 for the synthesis of 2-(pivaloyloxymethyl)-5-{-4-[2-(2-benzyloxyphenyl)ethenyl]phenyl}-tetrazole.

(G) 2-(Pivaloyloxymethyl)-5-{-4-[3-(2-benzyloxyphenyl)-propenyl]-4-phenyl}tetrazole was converted to 2-(pivaloyloxymethyl)-5-{-4-[3-(2-hydroxyphenyl)propyl]phenyl}-tetrazole by the process described in Example 1 (for the conversion of 4-(3-(2-benzyloxyphenyl)-3-carbonyl-1(E)-propenyl]benzoate to methyl 4-[3-(7-hydroxyphenyl)-3-carbonylpropyl]benzoate).

(H) 2-(Pivaloyloxymethyl)-5-{-4-[3-(2-hydroxyphenyl)propyl]-phenyl}tetrazole was converted to 2-(pivaloyloxymethyl)-5-{-4-[3-(2-benzyloxyphenyl)propyl]phenyl}tetrazole by the process described in Example 1 for the conversion of 4-[3-(2-hydroxyphenyl)propyl]benzoate to methyl 4-[3-(2-benzyloxyphenyl)propyl]benzoate.

EXAMPLE 26

4-[4-(2-Benzyloxyphenyl)butyl]benzoic acid (A) 4-[4-(2-benzyloxyphenyl)butyl]benzoic acid (mpt.105° C.) was prepared using a similar process to that described in Example 1 (A) from the corresponding methyl ester.

(B) Methyl 4-[4-(2-benzyloxyphenyl)butyl]benzoate was obtained as follows: benzyl 2-benzyloxyphenylacetate was obtained from 2-hydroxyphenylacetic acid using a similar method to that of Example 1 (I) except that two equivalents of benzyl bromide were used.

(C) To a solution of benzyl 2-benzyloxyphenylacetate (3.32 g) in $CH_2Cl_2$ (35 ml) at −70° C. was added a 1M solution of DIBAL in $CH_2Cl_2$ (12 ml). The reaction was stirred at −70° C. for 1.5 hours washed with 2N HCl, water, saturated aqueous sodium hydrogen carbonate solution and brine. The solution was dried ($MgSO_4$) and evaporated. The residue was purified by chromatography on silica gel using $CH_2Cl_2$ as eluant. There was thus obtained 2-benzyloxyphenylacetaldehyde (1.68 g).

(D) 4-[4-(2-benzyloxyphenyl)but-2-enyl]benzoate was obtained from 2-benzyloxyphenylacetaldehyde and 1-{4-carboxyphenyl)ethyl triphenylphosphonium bromide (see Example 1 (G)) using a similar method to that of Example 8 (E).

(E) 4-[4-(2-benzyloxyphenyl)butyl]benzoic acid was obtained from 4-[4-(2-benzyloxyphenyl)but2-enyl]benzoate using a similar method to that of Example 7 (E).

EXAMPLE 27

2-[3-(2-Benzyloxyphenyl)propyl]thiazol-4-ylcarboxylic acid

A similar process to that described in Example 1 (A) but using ethyl 2-[3-(2-benzyloxyphenyl)propyl]thiazol-4-ylcarboxylate was used to give the title compound (mpt. 93°-96° C.). Ethyl 4-[3-(2-benzyloxyphenyl)propyl]thiazol-2-ylcarboxylate was obtained from 2-benzyloxyphenylacetaldehyde and 4-ethoxycarbonylthiazol-2-ylmethyltriphenylphosphonium bromide using a similar method to that of Example 8 (E) (the pendant benzyloxy group remained attached).

The "phosphonium bromide" was obtained from ethyl 2-methylthiazol-4-ylcarboxylate using similar methods to those of Example 8 (C) and Example 8 (D).

EXAMPLE 28

A similar process to that of Example 1(A) with the appropriate methyl benzoates was used to prepare the compounds in the following table with appropriate modifications described in the footnotes.
| Compound | R¹ | Link | Ar | mpt | Footnote |
|---|---|---|---|---|---|
| 1 | 5-Br | CH₂CH₂ |  | 208–209 | a |
| 2 | 5-Br | CH₂CH₂ | 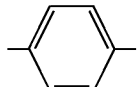 | 143–144 | b |
| 3 | 5-SMe | (E)CH=CH | " | 174–176 | c |
| 4 | 5-SMe | (E)CH=CH | 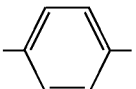 | 241–244 | d |
| 5 | 5-SMe | CH₂CH₂ | " | 190–191 | e |
| 6 | 5-SMe | CH₂CH₂ | 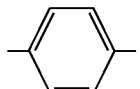 | 134–135 | f |
| 7 | 5-SO₂Me | CH₂CH2 | 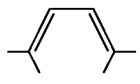 | 230–232 | g |
| 8 | 5-OMe | (E)CH=CH | " | 211–212 | h |
| 9 | 5-OMe | CH₂CH₂ | " | 162–163 | i |
| 10 | 5-CH₃ | CH₂CH₂ | " | 190–191 | j |
| 11 | H | CH₂CH₂ | 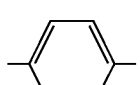 | 115–116 | k |
| 12 | H | —(CH₂)₃— | 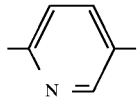 | — | l |
| 13 | H | (E)(CH=CH) | 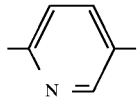 | 205–207 | m |
| 14 | H | —(CH₂)₂— | " | 167–170 | n |
| 15 | H | —(CH₂)₃— | " | — | o |
| 16 | H | (E)(CH=CH) | 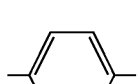 | 87–89 | p |

-continued

[Structure: benzene ring with positions 3,4,5,6 labeled; LINK—Ar—COOH at position 1; OCH₂Ph at position 2; R¹ at position 3]

| Compound | R¹ | Link | Ar | mpt | Footnote |
|---|---|---|---|---|---|
| 17 | H | —(CH₂)₃— | [1,4-phenylene-CH₂—] | 60–63 | q |
| 18 | H | —(CH₂)₃— | [2,5-thienyl] | — | r |
| 19 | H | (E)CH=CH | [pyrimidinyl] | 174 | s |
| 20 | 5-Br | (E)CH=CH | [pyridyl] | 194–200 | t |
| 21 | 5-Br | CH₂CH₂ | " | 196–199 | u |
| 22 | H | CH₂CH₂ | [pyridyl] | — | v |
| 23 | 5-SMe | (E)CH=CH | [pyridyl] | 200–206 | w |
| 24 | 5-SO₂Me | (E)CH=CH | " | 196–200 | x |
| 25 | 6-OH | —(CH₂)₃— | [phenylene] | 144–146 | y |
| 26 | 6-OCH₂Ph | —(CH₂)₃— | " | 142–143 | |
| 27 | 6-OMe | —(CH₂)₃— | " | 166–167 | z |
| 28 | 5-SMe | —(CH₂)₂— | [pyridyl] | 151–154 | (aa) |
| 29 | 5-SO₂Me | —(CH₂)₂— | " | 190–192 | (ab) |
| 30 | 5-SO₂Me | —(CH₂)₂— | [pyridyl N-oxide] | 206–210 | (ab) |
| 31 | H | (E)(CH=CH) | [hydroxyphenylene] | 160–161.5 | (ac) |

-continued
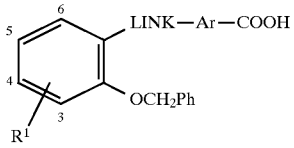
| Compound | R¹ | Link | Ar | mpt | Footnote |
|---|---|---|---|---|---|
| 32 | H | (E)CH=CH | 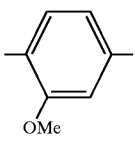 OMe | 181–182 | (ad) |
| 33 | H | —(CH₂)₂— | 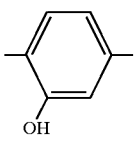 OH | 170–171 | (ae) |
| 34 | H | —(CH₂)₂— | 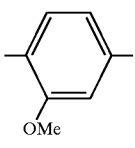 OMe | 131–131.5 | (af) |
| 35 | H | (Z)(CH=CH) | 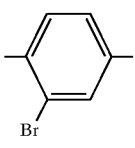 Br | 140–144 | (ag) |
| 36 | H | —(CH₂)₂— |  Br | 165.5–166.5 | (ah) |
| 37 | H | —(CH₂)₂— | 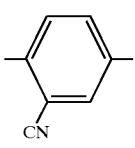 CN | 151.5–152.5 | (ai) |
| 38 | H | —(CH₂)₂— | 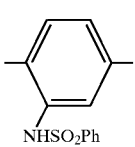 NHSO₂Ph | 186–187 | (aj) |
| 39 | H | —(CH₂)₂— | 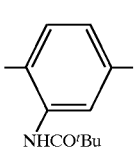 NHCOᵗBu | 187.5–188 | (ak) |
| 40 | H | —(CH₂)₃— | 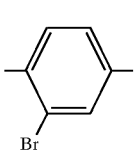 Br | 105–106.5 | (al) |
| 41 | H | —(CH₂)₃— | 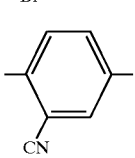 CN | 123–124 | (am) |

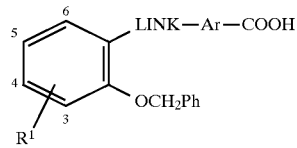

| Compound | R¹ | Link | Ar | mpt | Footnote |
|---|---|---|---|---|---|
| 42 | H | (E)CH=CH | Br-phenyl-Br (3,5-dibromo) | 214–215 | (an) |
| 43 | H | —(CH₂)₂— | " | 203–204 | (ao) |
| 44 | H | —(CH₂)₃— | OMe-phenyl | 121.5–122 | (ap) |
| 45 | 5-Cl | (Z)CH=CH | " | 191.5–192 | (aq) |
| 46 | 5-Cl | (E)CH=CH | " | 216.5–217 | (aq) |
| 47 | 5-Cl | —(CH₂)₂— | " | 158.5–159.5 | (ar) |
| 48 | 5-Br | —(CH₂)₂— | pyridinyl-NH₂ | 250–252 |  |
| 49 | H | —(CH₂)₂— | phenyl-NHCOCH₃ | 215.5–216.5 | (as) |

Footnotes a: -Methyl 4-(2-(benzyloxy-5-bromophenethyl)-2-hydroxybenzoate was prepared from a Z/E mixture of methyl 4-[2-(2-benzyloxy-5-bromo-phenyl)ethenyl]-2-hydroxybenzoate using a similar method to that of Example 7 (E). The alkenes were prepared from 2-benzyloxy-5-bromobenzaldehyde and 4-methoxycarbonyl-3-acetoxybenzyl-triphenylphosphonuim bromide by a similar method to that of Example 8 (E) in the course of which the acetate group was hydrolysed.
b: -Methyl 4-(2-benzyloxy-5-bromophenethyl)-2-methoxybenzoate was prepared from methyl 4-(2-benzyloxy-5-bromophenethyl)-2-hydroxybenzoate using a similar method to that of Example 2, Footnote C (A) replacing allyl bromide with methyl iodide.
c: -Methyl 4-{2-(2-benzyloxy-5-methanethiophenyl) ethenyl}-2-methoxybenzoate was prepared from methyl 4-[2-(2-benzyloxy-5-methanethiophenyl)ethenyl]-2-hydroxybenzoate using a similar method to that of Example 2, Footnote C (A) replacing allyl bromide with methyl iodide.
Methyl 4-[2-(2-benzyloxy-5-methanethiophenyl) ethenyl]-2-hydroxybenzoate was prepared from 2-benzyloxy-4-methanethio-benzaldehyde and 4-methoxycarbonyl-3-acetoxybenzyltriphenylphosphonium bromide using a similar method to that of Example 8, (E) in the course of which the acetate group was hydrolysed. The required E isomer was obtained from the mixture of Z and E isomers by separation using MPLC on silica gel.
d: -See second part of note (c).
e: -Methyl 4-[2-benzyloxy-5-methanethiophenethyl)-2-hydroxybenzoate was prepared from the corresponding alkenes using a similar method of that of Example 7, (E).
f: -Methyl 4-[2-benzyloxy-5-methanethiophenethyl)-2-methoxybenzoate was prepared from methyl 4-[2-benzyloxy-5-methanethiophenethyl)-2-hydroxybenzoate using a similar method to that a Example 2, Footnote c, (A) replacing allyl bromide with methyl iodide.
g: -Methyl 4-[2-benzyloxy-5-methanesulphonylphenethyl]-2-hydroxybenzoate was prepared from the corresponding sulphide using a modification of the method of Example 49, in which the reaction was carried out at 0° C.
h: -Methyl 4-[2-(2-benzyloxy-5-methoxyphenyl) ethenyl]-2-hydroxybenzoate was prepared by the second part of the method described in Footnote (c) using 2-benzyloxy-5-methoxybenzaldehyde in place of 2-benzyloxy-5-methylthiobenzaldehyde.
i: -Methyl 4-(2-benzyloxy-5-methoxyphenethyl)-2-hydroxybenzoate was prepared from the corresponding alkenes using method Example 7, (E).
j: -Methyl 4-(2-benzyloxy-5-methylphenethyl)-2-hydroxybenzoate was prepared as described in Footnote (a) replacing 2-benzyloxy-5-bromobenzaldehyde with 2-benzyloxy-5-methylbenzaldehyde.
k: -Ethyl 6-[2-benzyloxyphenethyl]-3-pyridazinecarboxylate was prepared as follows:-

-continued

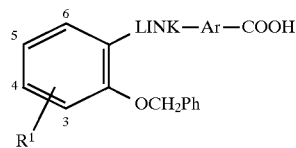

| Compound | R¹ | Link | Ar | mpt | Footnote |
|----------|-----|------|-----|-----|----------|

(A) 1-benzyloxy-2-iodobenzene (21.56 g), trimethylsilylacetylene (10.58 ml) (PPh₃)₂ Pd Cl₂ (972 mg) and CuI (133 mg) in ethylamine (150 ml) were stirred overnight. The solvent was evaporated, the residue extracted with diethyl ether, washed with 2N aqueous HCl and brine, then dried (MgSO₄), filtered and evaporated. The resulting residue was purified by MPLC on silica gel eluting with CH₂Cl₂:hexane (1:2) to give a brown solid (19.85 g).
(B) The brown solid (13.61 g) was dissolved in methanol (150 ml) and 2N aqueous NaOH (15 ml) was added. After 1 hour the solvent was evaporated and the residue extracted into diethyl ether, washed with brine, dried (MgSO₄), filtered and evaporated to give a product (9.93 g).
(C) A mixture of the product from the above step (9.93 g), ethyl 6-chloro-3-pyridazinecarboxylate [ref: Aust. J. Chem. 1977, 30, 2319] (4.45 g), (PPh₃)₂ Pd Cl₂ (335 mg) and CuI (45 mg) in triethylamine (100 ml) was stirred at 50° C. for 4 hours. The solvent was evaporated and the residue purified by MPLC silica gel eluting with CH₂Cl₂:ethyl acetate mixtures (0:1 to 1:1) followed by crystallisation from diethyl ether to give ethyl 6-(2-(2-benzyloxyphenyl)ethenyl)-3-pyridazinecarboxylate (2.46 g). The acetylene was converted to ethyl 6-[2-benzyloxyphenethyl]-3-pyridazinecarboxylate by method Example 9, (D).
1: -Methyl 5-[3-(2-benzyloxyphenyl)propyl]-2-pyridinecarboxylate was prepared using a similar sequence of methods to those described in Example 8, using 2-benzyloxyphenylacetaldehyde and methyl 5-hydroxymethyl-2-pyridinecarboxylate. The required phosphonium salt was prepared from methyl 5-methanesulphonyloxymethyl-2-pyridine-carboxylate which was made using standard procedures.
m: -Methyl 2-[2-(2-benzyloxyphenyl) ethenyl]-5-pyridinecarboxylate was prepared from methyl 2-methyl-5-pyridinecarboxylate using a similar method to that described in Example 8 to prepare methyl 4-[2-(2-benzyloxyphenyl)ethenyl]-3-fluorobenzoate.
n: -Methyl 2-[2-benzyloxyphenethyl]-5-pyridinecarboxylate was prepared from methyl 2-[2-(2-benzyloxyphenyl)ethenyl]-5-pyridinecarboxylate using a similar method to that of Example 1, (E) followed by benzylation of the phenol using a similar method to that of Example 1, (I).
o: -Methyl 2-[3-(2-benzyloxyphenyl)propyl]-5-pyridinecarboxylate was prepared using similar methods to those described in Example 8, using 2-benzyloxyphenylacetaldehyde and methyl 2-methyl-5-pyridinecarboxylate as starting materials.
p: -Methyl 5-[2-(2-benzyloxyphenyl)ethenyl]-2-pyridinecarboxylate was prepared from 2-benzyloxybenzyltriphenylphosphonium bromide and methyl 5-formyl-2-pyridinecarboxylate using similar methods to those described in Example 8.
q: -Methyl 4-[3-(2-benzyloxyphenyl)propyl]phenylacetate was prepared by similar methods to those described in Example 1, (G) and (H) from 2-benzyloxyphenylacetaldehyde and 4-carboxymethylbenzyltriphenylphosphonium bromide.
r: -Ethyl 5-[3-(2-benzyloxyphenyl)propyl]-2-thiophenecarboxylate was obtained as follows:- Ethyl 2-thiophenecarboxylate (25 g) was added to LDA (1 equivalent) in THF (150 ml) at −78° C. and stirred for 30 minutes. DMF (11.7 g) in THF (50 ml) was added and stirred at −78° C. for 30 minutes, then warmed to ambient temperature. The solvent was evaporated and the residue mixed with 2-benzyloxy-acetophenone (36.1 g) (prepared as described in Example 1, (B)) and potassium tert-butoxide (1 g) in ethanol (200 ml) and stirred at 20° C. for 16 hours. The solvent was evaporated, the residue dissolved in methylene chloride (100 ml) and filtered through silica, the solvent evaporated and the residue triturated to give ethyl 5-[2-(2-benzyloxybenzoyl)-ethenyl]-2-thiophenecarboxylate (47 g). Ethyl 5-[2-(2-benzyloxy-benzoyl)ethenyl]-2-thiophenecarboxylate was converted to ethyl 5-[2-(2-benzyloxybenzoyl)ethyl]-2-thiophenecarboxylate using a similar method to that of Example 1, (E) which was converted to ethyl 5-[3-(2-benzyloxyphenyl)propyl]-2-thiophenecarboxylate using a similar method to that of Example 1, (F).
s: -A mixture of methyl 5-methylpyrazinecarboxylate (1 g), 2-benzyloxybenzaldehyde (1.53 g), acetic acid (430 mg) and acetic anhydride (730 mg) was heated at 140° C. for 22 hours, cooled and purified by chromatography on silica gel, using CH₂Cl₂ ethyl acetate (99:1) as eluant. There was thus obtained methyl 2-[2-(2-benzyloxyphenyl)ethenyl]-5-pyrazinecarboxylate (1.1 g) mpt. 105° C.
t: -Methyl 2-[2-(2-benzyloxy-5-bromophenyl)ethenyl]-5-pyrazine-carboxylate was prepared from 2-benzyloxy-5-bromobenzaldehyde and methyl 2-methyl-5-pyridine carboxylate using a similar method to that of Example 28, Footnote s.
u: -Methyl 2-[2-benzyloxy-5-bromophenethyl)-5-pyridinecarboxylate was prepared from methyl 2-[2-(2-benzyloxy-5-bromophenyl)-ethenyl]-5-pyrazinecarboxylate using a similar method to that of Example 1, (E), separating the product from side products by MPLC, eluting with CH₂Cl₂:EtOAc (98:2).
v: -The ester methyl 2-[2-benzyloxyphenethyl]-5-pyridinecarboxylate was prepared from methyl 2-[2-(2-benzyloxyphenyl)ethenyl]-5-pyridinecarboxylate using a similar method to that of Example 7, (E).
w: -The ester methyl 2-[2-(2-benzyloxy-5-methanethiophenyl)-ethenyl]-5-pyrazinecarboxylate was prepared from 2-benzyloxy-5-methanethiobenzaldehyde and methyl 2-methyl-5-pyridinecarboxylate using a similar method to that of Example 28, Footnote k.
x: -The ester methyl 2-[2-(2-benzyloxy-5-methanesulphonylphenyl)ethenyl]-5-pyrazinecarboxylate was prepared from methyl 2-[2-(2-benzyloxy-5-methanethiophenyl)ethenyl]-5-pyrazinecarboxylate using a similar method to that of Example 49.
y: -The esters methyl 4-[3-(2-benzyloxy-6-hydroxyphenyl)-propyl]benzoate and methyl 4-[3-(2-benzyloxy-6-benzyloxy-phenyl)propyl]benzoate were prepared as follows:-

-continued

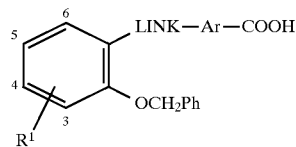

| Compound | R¹ | Link | Ar | mpt | Footnote |
| --- | --- | --- | --- | --- | --- |

(A) Methyl 4-[3-(2,6-dimethoxy)propyl]benzoate was prepared from 2,6-dimethoxybenzaldehyde and 4-carboxyphenethyltriphenylphosphonium bromide by similar methods to that of Example 1 (G) and (H).
(B) Boron tribromide was added to a stirred solution of methyl 4-[3-(2,6-dimethoxy)propyl]benzoate (11.31 g) at −78° C. in $CH_2Cl_2$, then stirred at ambient temperature for 15 hours. The mixture was cooled (−30° C.) and water added dropwise. The reaction was poured into EtOAc and the organic layer washed with water, dried ($MgSO_4$), filtered and evaporated to give methyl 4-[3-(2,6-dihydroxy)propyl]benzoate as a brown oil (14.65 g).
(C) A mixture of methyl 4-[3-(2,6-dihyroxy)propyl]benzoate (8.13 g), benzyl bromide (3.38 ml) and potassium carbonate (3.86 g) was stirred in DMF for 18 hours. The DMF was evaporated and the residue purified by MPLC on silica gel eluting with $CH_2Cl_2$. Methyl 4-[3-(2-benzyloxy-6-benzyloxyphenyl) propyl]benzoate (4.03 g), methyl 4-[3-(2-benzyloxy-6-hydroxyphenyl) propyl] benzoate (2.28 g) and methyl 4-[3-(2,6-dihydroxy)propyl]benzoate (2.77 g) were obtained.
z: -Methyl 4-[3-(2-benzyloxy-6-methoxyphenyl)propyl]benzoate was prepared as follows: methyl 4-[3-(2,6-dihydroxy, propyl]benzoate (2.92 g), prepared from the methyl ester by a similar method to that of Example 1 (A), and conc. $H_2SO_4$ (1 drop) in methanol (100 ml) were heated at reflux for 18 hours. The solvent was evaporated, the residue extracted with EtOAc, washed with water, dried, filtered and evaporated. The resulting gum was purified by MPLC on silica gel eluting with $CH_2Cl_2$ to give methyl 4-[3-(2-hydroxy-6-methoxyphenyl)propyl]benzoate (2.27 g).
Methyl 4-[3-(2-hydroxy-6-methoxyphenyl)propyl]benzoate was converted to methyl 4-[3-(2-benzyloxy-6-methoxyphenyl)propyl]benzoate by a similar method to that of Example 1, (B).
aa: -Methyl 2-[2-benzyloxy-5-methanethiophenethyl]-5-pyridine-carboxylate was prepared from the corresponding alkene (Example 28, compound 23) using a similar method to that of Example 7, (E).
ab: -Methyl 2-[2-benzyloxy-5-methanesulphonylphenethyl]-5-pyridinecarboxylate was prepared from the corresponding sulphide (see footnote (aa)) using a similar method to that of Example 49. Methyl 2-[2-benzyloxy-5-(methanesulphonylphenethyl]-5-(methoxycarbonyl)-pyridine-1-oxide was obtained as a side product from this reaction.
ac: -Methyl 4-[2-2-benzyloxyphenyl)ethenyl]-3-hydroxybenzoate was prepared from methyl 2-acetoxy-4-methylbenzoate and 2-benzyloxybenzaldehyde using similar processes to those described in Example 8 and purified by crystallisation from ethyl acetate/hexane mixtures.
ad: -Methyl 4-[2-(2-benzyloxyphenyl)ethenyl]-3-methoxybenzoate was prepared from methyl 4-[2-(2-benzyloxyphenyl)ethenyl]-3-hydroxybenzoate by a similar method to that of Example 1 (I).
ae: -Methyl 4-[2-benzyloxyphenethyl]-3-hydroxybenzoate was prepared from methyl 4-[2-(2-benzyloxyphenyl)ethenyl]-3-hydroxybenzoate by a similar method to that of Example 7, (E).
af: -Methyl 4-[2-benzyloxyphenethyl]-3-methoxybenzoate was made from methyl 4-[2-(2-benzyloxyphenyl)ethenyl]-3-methoxybenzoate by a similar method to that of Example 1, (E) using ethanol/THF as the solvent and stopping the reaction after the absorption of 1.1 equivalents of hydrogen gas.
ag: -Methyl 4-[2-(2-benzyloxyphenyl)-(Z)-ethenyl]-3-bromobenzoate was prepared from methyl 3-bromo-4-methylbenzoate and 2-benzyloxybenzaldehyde using similar processes to those described in Example 8. It was purified by MPLC on silica gel eluting with $CH_2Cl_2$:hexane (3:7) followed by crystallisation from diethyl ether/hexane mixtures (mpt 78.5–79.5° C).
ah: -Methyl 4-[2-benzyloxyphenethyl]-3-bromobenzoate was prepared from a mixture of the alkenes methyl 4-[2-(2-benzyloxyphenyl)ethenyl]-3-bromobenzoate using a similar method to that of Example 7, (E).
ai: -Methyl 4-[2-benzyloxyphenethyl]-3-cyanobenzoate was prepared from methyl 4-[2-benzyloxyphenethyl)-3-bromobenzoate by a similar method to that of Example 3, Footnote n.
aj: -Methyl 4-[2-benzyloxyphenethyl]-3-phenylsulphonylaminobenzoate was prepared from methyl 4-[2-benzyloxyphenethyl)-3-aminobenzoate using a similar method to that of Example 3, Footnote g, using triethylamine in place of potassium carbonate.
ak: -Methyl 4-[2-benzyloxyphenethyl]-3-(2,2-dimethylpropionylaminobenzoate was prepared from methyl 4-[2-benzyloxyphenethyl)-3-aminobenzoate by a similar method to that of example 2 footnote b. using tBuCOCl in place of acetic anhydride.
al: -Methyl 4-[3-(2-benzyloxyphenyl)propyl]-2-bromobenzoate was prepared from 2-benzyloxyphenylacetaldehyde and methyl 3-bromo-4-methylbenzoate using a similar process to that described in example 8. The final step to reduce the mixture of alkenes was carried out using a similar method to that of example 7 (E).
am: -Methyl 4-[3-(2-benzyloxyphenyl)propyl]-2-cyanobenzoate was prepared from methyl 4-[3-(2-benzyloxyphenyl)propyl]-2-bromobenzoate by a similar method to that of example 3 footnote n.
an: -Methyl 4-[2-(2-benzyloxyphenyl)ethenyl]-3,5-dibromobenzoate was prepared from 2-benzyloxybenzaldehyde and methyl 3,5-dibromo-4-methylbenzoate using a similar processe to that described in example 8.
ao: -Ethyl 4-[2-benzyloxyphenethyl]-3,5-dibromobenzoate was prepared from methyl 4-[2-(2-benzyloxyphenyl)ethenyl]-3,5-dibromobenzoate by a similar method to that of example 7(E), modifying the conditions by carrying out the reaction for 60 hours. During this time ester exchange occured giving the ethyl ester.
ap: -Methyl 4-[3-(2-benzyloxyphenyl)propyl]-3-methoxybenzoate was prepared from methyl 3-methoxy-4-methylbenzoate and 2-benzyloxyphenylacetaldehyde using a similar process to that described in Example 8. The final reduction step was carried out using a modification of the method of Example 1, (E) in which 5% $Pd/BaSO_4$ was added as the hydrogenation catalyst.

-continued

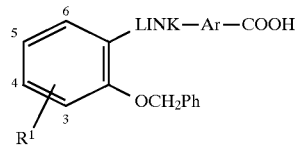

| Compound | R¹ | Link | Ar | mpt | Footnote |
| --- | --- | --- | --- | --- | --- | aq: -A mixture of (Z) and (E) alkenes of methyl 4-[2-(2-benzyloxy-5-chlorophenyl)ethenyl]-3-methoxybenzoate was prepared using similar processes to those described in Example 8, starting with 2-benzyloxy-5-chlorobenzaldehyde and methyl 3-methoxy-4-bromomethylbenzoate. The isomeric esters were separated and isolated by fractional crystallisation from ethyl acetate/hexane mixtures.
ar: -The ester methyl 4-[2-benzyloxy-5-chlorophenethyl]-3-methoxybenzoate was prepared from a mixture of the (Z) and (E) alkenes by a similar method to that of Example 7, (E).
as: -Methyl 4-[2-benzyloxyphenethyl]-3-acetylaminobenzoate was synthesised from methyl 4-[2-benzyloxyphenethyl]-3-aminobenzoate by a similar method to that of Example 2, Footnote b, using $CH_3COCl$ in place of $Ac_2O$.

Footnotes
a:- Methyl 4-(2-(benzyloxy-5-bromophenethyl)-2-hydroxybenzoate was prepared from a Z/E mixture of methyl 4-[2-(2-benzyloxy-5-bromopenyl)ethenyl]-2-hydroxybenzoate using a similar method to that of ample 7 (E). The alkenes were prepared from 2-benzyloxy-5-bromobenzaldehyde and 4-methoxycarbonyl-3-acetoxybenzyl-triphenylphosphonuim bromide by a similar method to that of Example 8 (E) in the course of which the acetate group was hydrolysed.
b:- Methyl 4-(2-benzyloxy-5-bromophenethyl)-2-methoxybenzoate was prepared from methyl 4-(2-benzyloxy-5-bromophenethyl)-2-hydroxybenzoate using a similar method to that of Example 2, Footnote C (A) replacing allyl bromide with methyl iodide.
c:- Methyl 4-{2-(2-benzyloxy-5-methanethiophenyl)ethenyl]-2-methoxybenzoate was prepared from methyl 4-[2-(2-benzyloxy-5-methanethiophenyl)ethenyl]-2-hydroxybenzoate using a similar method to that of Example 2, Footnote C (A) replacing allyl bromide with methyl iodide.
Methyl 4-[2-(2-benzyloxy-5-methanethiophenyl)ethenyl]-2-hydroxybenzoate was prepared from 2-benzyloxy-4-methanethiobenzaldehyde and 4-methoxycarbonyl-3-acetoxybenzyltriphenylphosphonium bromide using a similar method to that of Example 8, (E) in the course of which the acetate group was hydrolysed. The required E isomer was obtained from the mixture of Z and E isomers by separation using MPLC on silica gel.
d:- See second part of note (c).
e:- Methyl 4-[2-benzyloxy-5-methanethiophenethyl)-2-hydroxybenzoate was prepared from the corresponding alkenes using a similar method of that of Example 7, (E).
f:- Methyl 4-[2-benzyloxy-5-methanethiophenethyl)-2-methoxybenzoate was prepared from methyl 4-[2-benzyloxy-5-methanethiophenethyl)-2-hydroxybenzoate using a similar method to that a Example 2, Footnote c, (A) replacing allyl bromide with methyl iodide.
f:- Methyl 4-[2-benzyloxy-5-methanesulphonylphenethyl)-2-hydroxybenzoate was prepared from the corresponding sulphide using a modification of the method of Example 49, in which the reaction was carried out at 0° C.
h:- Methyl 4-[2-(2-benzyloxy-5-methoxyphenyl)ethenyl]-2-hydroxybenzoate was prepared by the second part of the method described in Footnote (c) using 2-benzyloxy-5-methoxybenzaldehyde in place of 2-benzyloxy-5-methylthiobenzaldehyde.
i:- Methyl 4-(2-benzyloxy-5-methoxyphenethyl)-2-hydroxybenzoate was prepared from the corresponding alkenes using method Example 7, (E).
j:- Methyl 4-(2-benzyloxy-5-methylphenethyl)-2-hydroxybenzoate was prepared as described in Footnote (a) replacing 2-benzyloxy-5-bromobenzaldehyde with 2-benzyloxy-5-methylbenzaldehyde.
k:- Ethyl 6-[2-benzyloxyphenethyl]-3-pyridizinecarboxylate was prepared as follows:
(A) 1-benzyloxy-2-iodobenzene (21.56 g), trimethylsilylacetylene (10.58 ml) $(PPh_3)_2$ Pd $Cl_2$ (972 mg) and CuI (133 mg) in ethylamine (150 ml) were stirred overnight. The solvent was evaporated, the residue extracted with diethyl ether, washed with 2N aqueous HCl and brine, then dried $(MgSO_4)$, filtered and evaporated. The resulting residue was purified by MPLC on silica gel eluting with $CH_2Cl_2$:hexane (1:2) to give a brown solid (19.85 g).
(B) The brown solid (13.61 g) was dissolved in methanol (150 ml) and 2N aqueous NaOH (15 ml) was added. After 1 hour the solvent was evaporated and the residue extracted into diethyl ether, washed with brine, dried $(MgSO_4)$, filtered and evaporated to give a product (9.93 g).
(C) A mixture of the product from the above step (9.93 g), ethyl 6-chloro-3-pyridazinecarboxylate [ref: Aust. J. Chem. 1977, 30, 2319] (4.45 g), $(PPh_3)_2$ Pd $Cl_2$ (335 mg) and CuI (45 mg) in triethylamine (100 ml) was stirred at 50° C. for 4 hours. The solvent was evaporated and the residue purified by MPLC on silica gel eluting with $CH_2Cl_2$: ethyl acetate mixtures (0:1 to 1:1) followed by crystallisation from diethyl ether to give ethyl 6-[2-(2-benzyloxyphenyl)ethenyl)-3-pyridazinecarboxylate (2.46 g). The acetylene was converted to ethyl 6-[2-benzyloxyphenethyl]-3-pyridazinecarboxylate by method Example 9, (D).
l:- Methyl 5-(3-(2-benzyloxyphenyl)propyl]-2-pyridinecarboxylate was prepared using a similar sequence of methods to those described in Example 8, using 2-benzyloxyphenylacetaldehyde and methyl 5-hydroxymethyl-2- pyridinecarboxylate. The required phosphonium salt was prepared from methyl 5-methanesulphonyloxymethyl-2-pyridine-carboxylate which was made using standard procedures.
m:- Methyl 2-[2-(2-benzyloxyphenyl)ethenyl]-5-pyridinecarboxylate was prepared from methyl 2-methyl-5-pyridinecarboxylate using a similar method to that described in Example 8 to prepare methyl 4-[2-(2-benzyloxyphenyl)ethenyl)-3-fluorobenzoate.
n:- Methyl 2-[2-benzyloxyphenethyl]-5-pyridinecarboxylate was prepared from methyl 2-[2-(2-benzyloxyphenyl)ethenyl]-5-pyridinecarboxylate using a similar method to that of Example 1, (E) followed by benzylation of the phenol using a similar method to that of Example 1, (I).
o:- Methyl 2-[3-(2-benzyloxyphenyl)propyl)-5-pyridinecarboxylate was prepared using similar methods to those described in Example 8, using 2-benzyloxyphenylacetaldehyde and methyl 2-methyl-5-pyridinecarboxylate as starting materials.

p:- Methyl 5-[2-(2-benzyloxyphenyl)ethenyl]-2-pyridinecarboxylate was prepared from 2-benzyloxybenzyltriphenylphosphonium bromide and methyl 5-formyl-2-pyridinecarboxylate using similar methods to those described in Example 8.

q:- Methyl 4-[3-(2-benzyloxyphenyl)propyl]phenylacetate was prepared by similar methods to those described in Example 1, (G) and (H) from 2-benzyloxyphenylacetaldehyde and 4-carboxymethylbenzyltriphenylphosphonium bromide.

r:- Ethyl 5-[3-(2-benzyloxyphenyl) propyl]-2-thiophenecarboxylate was obtained as follows:- Ethyl 2-thiophenecarboxylate (25 g) was added to LDA (1 equivalent) in THF (150 ml) at −78° C. and stirred for 30 minutes. DMF (11.7 g) in THF (50 ml) was added and stirred at −78° C. for 30 minutes, then warmed to ambient temperature. The solvent was evaporated and the residue mixed with 2-benzyloxy-acetophenone (36.1 g) (prepared as described in Example 1, (B)) and potassium tert-butoxide (1 g) in ethanol (200 ml) and stirred at 20° C. for 16 hours. The solvent was evaporated, the residue dissolved in methylene chloride (100 ml) and filtered through silica, the solvent evaporated and the residue triturated to give ethyl 5-[2-(2-benzyloxybenzoyl)-ethenyl]-2-thiophenecarboxylate (47 g). Ethyl 5-[2-(2-benzyloxybenzoyl)ethenyl]-2-thiophenecarboxylate was converted to ethyl 5-[2-(2-benzyloxybenzoyl)ethenyl]-2-thiophenecarboxylate using a similar method to that of Example 1, (E) which was converted to ethyl 5-[3-(2-benzyloxyphenyl)propyl]-2-thiophenecarboxylate using a similar method to that of Example 1, (F).

s:- A mixture of methyl 5-methylpyrazinecarboxylate (1 g), 2-benzyloxybenzaldehyde (1.53 g), acetic acid (430 mg) and acetic anhydride (730 mg) was heated at 140° C. for 22 hours, cooled and purified by chromatography on silica gel, using $CH_2Cl_2$ ethyl acetate (99:1) as eluant. There was thus obtained methyl 2-[2-(2-benzyloxyphenyl)ethenyl]-5-pyrazinecarboxylate (1.1 g) mpt. 105° C.

t:- Methyl 2-[2-(2-benzyloxy-5-bromophenyl)ethenyl]-5-pyrazine-carboxylate was prepared from 2-benzyloxy-5-bromobenzaldehyde and methyl 2-methyl-5-pyridine carboxylate using a similar method to that of Example 28, Footnote s.

u:- Methyl 2-[2-benzyloxy-5-bromophenethyl]-5-pyridinecarboxylate was prepared from methyl 2-[2-(2-benzyloxy-5-bromophenyl)-ethenyl]-5-pyrazinecarboxylate using a similar method to that of Example 1, (E), separating the product from side products by MPLC, eluting with $CH_2Cl_2$: EtOAc (98:2).

v:- The ester methyl 2-[2-benzyloxyphenethyl]-5-pyridinecarboxylate was prepared from methyl 2-[2-(2-benzyloxyphenyl)ethenyl]-5-pyridinecarboxylate using a similar method to that of Example 7, (E).

w:- The ester methyl 2-[2-(2-benzyloxy-5-methanethiophenyl)-ethenyl]-5-pyrazinecarboxylate was prepared from 2-benzyloxy-5-methanethiobenzaldehyde and methyl 2-methyl-5-pyridinecarboxylate using a similar method to that of Example 28, Footnote k.

x:- The ester methyl 2-(2-(2-benzyloxy-5-methanesulphonylphenyl) ethenyl]-5-pyrazinecarboxylate was prepared from methyl 2-[2-(2-benzyloxy-5-methanethiophenyl)ethenyl]-5-pyrazinecarboxylate using a similar method to that of Example 49.

y:- The esters methyl 4-(3-(2-benzyloxy-6-hydroxyphenyl)-propyl]benzoate and methyl 4-[3-(2-benzyloxy-6-benzyloxyphenyl)propyl]benzoate were prepared as follows:

(A) Methyl 4-(3-(2,6-dimethoxy)propyl]benzoate was prepared from 2,6-dimethoxybenzaldehyde and 4-carboxyphenethyltriphenylphosphonium bromide by similar methods to that of Example 1 (G) and (H).

(B) Boron tribromide was added to a stirred solution of methyl 4-(3-(2,6-dimethoxy)propyl]benzoate (11.31 g) at −78° C. in $CH_2Cl_2$, then stirred at ambient temperature for 15 hours. The mixture was cooled (−30° C.) and water added dropwise. The reaction was poured into EtOAc and the organic layer washed with water, dried ($MgSO_4$), filtered and evaporated to give methyl 4-(3-(2,6-dihydroxy)propyl] benzoate as a brown oil (14.65 g).

(C) A mixture of methyl 4-[3-(2,6-dihydroxy)propyl] benzoate (8.13 g), benzyl bromide (3.38 ml) and potassium carbonate (3.86 g) was stirred in DMF for 18 hours. The DMF was evaporated and the residue purified by MPLC on silica gel eluting with $CH_2Cl_2$. Methyl 4-[3-(2-benzyloxy-6-benzyloxyphenyl) propyl]benzoate (4.03 g), methyl 4-(3-(2-benzyloxy-6-hydroxyphenyl) propyl]benzoate (2.28 g) and methyl 4-(3-(2,6-dihydroxy)propyl]benzoate (2.77 g) were obtained.

z:- Methyl 4-(3-(2-benzyloxy-6-methoxyphenyl)propyl) benzoate was prepared as follows: methyl 4-[3-(2,6-dihydroxy)propyl]benzoate (2.92 g), prepared from the methyl ester by a similar method to that of Example 1 (A), and conc. $H_2SO_4$ (1 drop) in methanol (100 ml) were heated at reflux for 18 hours. The solvent was evaporated, the residue extracted with EtOAc, washed with water, dried, filtered and evaporated. The resulting gum was purified by MPLC on silica gel, eluting with $CH_2Cl_2$ to give methyl 4-[3-(2-hydroxy-6-methoxyphenyl) propyl]benzoate (2.27 g).

Methyl 4-[3-(2-hydroxy-6-methoxyphenyl)propyl] benzoate was converted to methyl 4-[3-(2-benzyloxy-6-methoxyphenyl)propyl]benzoate by a similar method to that of Example 1, (B).

aa:- Methyl 2-[2-benzyloxy-5-methanethiophenethyl]-5-pyridine-carboxylate was prepared from the corresponding alkene (Example 28, compound 23) using a similar method to that of Example 7, (E).

ab:- Methyl 2-[2-benzyloxy-5-methanesulphonylphenethyl] -5-pyridinecarboxylate was prepared from the corresponding sulphide (see footnote (aa) using a similar method to that of Example 49. Methyl 2-[2-benzyloxy-5-methanesulphonylphenethyl]-5-(methoxycarbonyl)-pyridine-1-oxide was obtained as a side product from this reaction.

ac:- Methyl 4-[2-(2-benzyloxyphenyl)ethenyl]-3-hydroxybenzoate was prepared from methyl 2-acetoxy-4-methylbenzoate and 2-benzyloxybenzaldehyde using similar processes to those described in Example 8 and purified by crystallisation from ethyl acetate/hexane mixtures.

ad:- Methyl 4-[2-(2-benzyloxyphenyl)ethenyl)-3-methoxybenzoate was prepared from methyl4-[2-(2-benzyloxyphenyl) ethenyl]-3-hydroxybenzoate by a similar method to that of Example 1 (I).

ae:- Methyl 4-(2-benzyloxlphenethyl]-3-hydroxybenzoate was prepared from methyl 4-[2-(2-benzyloxyphenyl) ethenyl)-3-hydroxybenzoate by a similar method to that of Example 7, (E).

af:- Methyl 4-(2-benzyloxlphenethyl]-3-methoxybenzoate was made from methyl 4-[2-(2-benzyloxyphenyl)ethenyl]-3-methoxybenzoate by a similar method to that of Example 1, (E) using ethanol/THF as the solvent and stopping the reaction after the absorption of 1.1 equivalents of hydrogen gas.

ag:- Methyl 4-[2-(2-benzyloxyphenyl)-(Z)-ethenyl]-3-bromobenzoate was prepared from methyl 3-bromo-4- methylbenzoate and 2-benzyloxybenzaldehyde using similar processes to those described in Example 8. It was purified by MPLC on silica gel eluting with $CH_2Cl_2$: hexane (3:7)-followed by crystallisation from diethyl ether/hexane mixtures (mpt 73.5°-79.5° C.).

ah:- Methyl 4-[2-benzyloxyphenethyl]-3-bromobenzoate was prepared from a mixture of the alkenes methyl 4-[2-(2-benzyloxyphenyl)ethenyl]-3-bromobenzoate using a similar method to that of Example 7, (E).

ai:- Methyl 4-[2-benzyloxyphenethyl]-3-cyanobenzoate was prepared from methyl 4-[2-benzyloxyphenethyl]-3-bromobenzoate by a similar method to that of Example 3, Footnote n.

aj:- Methyl 4-[2-benzyloxyphenethyl]-3-phenylsulphonylaminobenzoate was prepared from methyl 4-[2-benzyloxyphenethyl]-3-aminobenzoate using a similar method to that of Example 3, Footnote g, using triethylamine in place of potassium carbonate.

ak:- Methyl 4-[2-benzyloxyphenethyl]-3-(2,2-dimethylpropionylaminobenzoate was prepared from methyl 4-[2-benzyloxyphenethyl]-3-aminobenzoate by a similar method to that of example 2 footnote b. using tBuCOCl in place of acetic anhydride.

al:- Methyl 4-[3-(2-benzyloxyphenyl)propyl]-2-bromobenzoate was prepared from 2-benzyloxyphenylacetaldehyde and methyl 3-bromo-4-methylbenzoate using a similar process to that described in example 8. The final step to reduce the mixture of alkenes was carried out using a similar method to that of example 7(E).

am:- Methyl 4-[3-(2-benzyloxyphenyl)propyl)-2-cyanobenzoate was prepared from methyl 4-(3-(2-benzyloxyphenyl)propyl)-2-bromobenzoate by a similar method to that of example 3 footnote n.

an:- Methyl 4-[2-(2-benzyloxyphenyl)ethenyl]-3,5-dibromobenzoate was prepared from 2-benzyloxybenzaldehyde and methyl 3,5-dibromo-4-methylbenzoate using a similar process to that described in example 8.

ao:- Ethyl 4-[2-benzyloxyphenethyl]-3,5-dibromobenzoate was prepared from methyl 4-[2-(2-benzyloxyphenyl)ethenyl]-3,5-dibromobenzoate by a similar method to that of example 7(E), modifying the conditions by carrying out the reaction for 60 hours. During this time ester exchange occurred giving the ethyl ester.

ap:- Methyl 4-[3-(2-benzyloxyphenyl)propyl]-3-methoxybenzoate was prepared from methyl 3-methoxy-4-methylbenzoate and 2-benzyloxyphenylacetaldehyde using a similar process to that described in Example 8. The final reduction step was carried out using a modification of the method of Example 1, (E) in which 5% Pd/BaSO$_4$ was added as the hydrogenation catalyst.

aq:- A mixture of (Z) and (E) alkenes of methyl 4-[2-(2-benzyloxy-5-chlorophenyl)ethenyl]-3-methoxybenzoate was prepared using similar processes to those described in Example 8, starting with 2-benzyloxy-5-chlorobenzaldehyde and methyl 3-methoxy-4-bromomethylbenzoate. The isomeric esters were separated and isolated by fractional crystallisation from ethyl acetate/hexane mixtures.

ar:- The ester methyl 4-(2-benzyloxy-5-chlorophenethyl)-3-methoxybenzoate was prepared from a mixture of the (Z) and (E) alkenes by a similar method to that of Example 7, (E).

as:- Methyl 4-[2-benzyloxyphenethyl]-3-acetylaminobenzoate was synthesised from methyl 4-[2-benzyloxyphenethyl]-3-aminobenzoate by a similar method to that of Example 2, Footnote b, using CH$_3$COCl in place of Ac$_2$O.

EXAMPLE 29

The process of Example 84 (A) was repeated with the appropriate nitriles to give the compounds described in the following table:

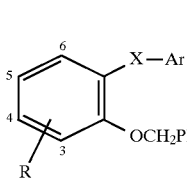

| Compound | R | X | Ar | mpt | Footnote |
|---|---|---|---|---|---|
| 1 | H | -(CH$_2$)$_2$- | 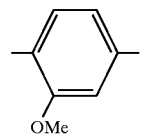 Br | 259.5–260.5 | a |
| 2 | H | -(CH$_2$)$_3$- | " | 181–182 | a |
| 3 | H | -(CH$_2$)$_2$- | OMe | 176–178 | a |
| 4 | H | -(CH$_2$)$_3$- | " | 181.5–183 | a |
| 5 | 5-Cl | -(CH$_2$)$_2$- | " | 184.5–186 | a |

-continued

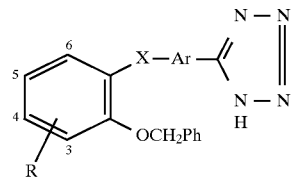

| Compound | R | X | Ar | mpt | Footnote |
|---|---|---|---|---|---|
| 6 | 5-Cl | -(CH₂)₂- | (phenyl) | 244–245 | b |
| 7 | 5-Br | -(CH₂)₂- | (N-Me-2-oxo-pyridinyl)-CONHCH₂- | 191–193 | |
| 8 | 5-Br | -(CH₂)₂- | (2-OMe-pyridinyl)-CONHCH₂- | 196–198 | |
| 9 | 5-Br | -(CH₂)₂- | (NH-2-oxo-pyridinyl)-CONHCH₂- | 250–255 | c |

Footnotes
a:- The relevant nitrile precursors were prepared from the corresponding primary amides as exemplified by the following method: Trifluoroacetic anhydride (0.75 ml) was added to a mixture of 4-[2-benzyloxyphenethyl]-3-bromobenzamide (1.46 g) and pyridine (0.86 ml) in THF at −20° C. The mixture was stirred at ambient temperature for 18 hours, diluted with ethyl acetate and washed with water, dried (MgSO₄), filtered and evaporated to dryness. The resulting residue was purified by MPLC on silica gel, eluting with CH₂Cl₂ to give 4-[2-benzyloxyphenethyl]-3-bromobenzonitrile as a white solid (1.34 g).
b:- p-tolunitrile (1.17 g) in THF (20 ml) was added to a solution of LDA (1.1 equivalents) in THF at −70° C. After 5 minutes, 2-benzyloxy-5-chlorobenzyl bromide (2.33 g) in THF (20 ml) was added dropwise to the reaction mixture at −70° C. The mixture was poured into 50% aqueous saturated ammonium chloride solution and extracted with ethyl acetate. The organic layer was washed (brine), dried and evaporated. The residue was subjected to chromatography an 7734 silica gel, (eluting with CH₂Cl₂: hexane mixture (2.5:97.5 to 50:50) to give 4-[2-benzyloxy-5-chlorophenethyl]benzonitrile (1.4 g) mpt 77–79° C.
c:- The nitrile N-cyanomethyl-6-[2-benzyloxy-5-bromophenethyl]-2-oxo-1H-pyridine-3-carboxamide was prepared from 6-[2-benzyloxy-5-bromophenethyl]-2-oxo-1H-pyridine-3-carboxylic acid by method.

Footnotes
a:- The relevant nitrile precursors were prepared from the corresponding primary amides as exemplified by the following method:
Trifluoroacetic anhydride (0.75 ml) was added to a mixture of 4-[2-benzyloxyphenethyl]-3-bromobenzamide (1.46 g) and pyridine (0.86 ml) in THF at −20° C. The mixture was stirred at ambient temperature for 18 hours, diluted with ethyl acetate and washed with water, dried (MgSO₄), filtered and evaporated to dryness. The resulting residue was purified by MPLC on silica gel, eluting with CH₂Cl₂ to give 4-[2-benzyloxyphenethyl]-3-bromobenzonitrile as a white solid (1.34 g).
b:- p-tolunitrile (1.17 g) in THF (20 ml) was added to a solution of LDA (1.1 equivalents) in THF at −70° C. After 5 minutes, 2-benzyloxy-5-chlorobenzyl bromide (2.33 g) in THF (20 ml) was added dropwise to the reaction mixture at −70° C. The mixture was poured into 50% aqueous saturated ammonium chloride solution and extracted with ethyl acetate. The organic layer was washed (brine), dried and evaporated. The residue was subjected to chromatography an 7734 silica gel, (eluting with CH₂Cl₂: hexane mixture (2.5:97.5 to 50:50) to give 4-[2-benzyloxy-5-chlorophenethyl]benzonitrile (1.4 g) mpt 77°-79° C.
c:- The nitrile N-cyanomethyl-6-(2-benzyloxy-5-bromophenethyl)-2-oxo-1H-pyridine-3-carboxamide was prepared from 6-[2-benzyloxy-5-bromophenethyl]-2-oxo-1H-pyridine-3-carboxylic acid by method.

EXAMPLE 30

4-[3-(2-Benzyloxy-4-bromophenyl)propyl]benzoic acid

4-[3-(2-Benzyloxy-4-bromophenyl)propyl]benzoic acid (mpt 141°-142° C.) was prepared from a mixture of 4-[3-(2-benzyloxy-4-bromophenyl)prop-2-enyl]benzoic acid and 4-[3-(2-benzyloxy-4-bromophenyl)prop-1-enyl]benzoic acid by a similar method to that of Example 7, (E). The mixture of alkenes was prepared from 2-benzyloxy-4-bromobenzaldehyde and 4-carboxyphenethyltriphenylphosphonium bromide by a similar method to that of Example 1, (G).

EXAMPLE 31

4-[3-(2-Benzyloxy-5-chlorophenyl)prop-1-enyl]benzoic acid

4-[3-(2-Benzyloxy-5-chlorophenyl)prop-1-enyl]benzoic acid (mpt 157°-150° C.) was prepared by a similar method to that of Example 1, (G) from 2-benzyloxy-5- chlorobenzaldehyde and was purified from a mixture of isomers by fractional crystallisation from ethyl acetate:hexane mixtures.

EXAMPLE 32

4-[3-(2-Benzyloxy-5-iodophenyl-propyl]benzoic acid

To a solution of 4-[3-(2-benzyloxyphenethyl)propyl] benzoic acid (3.5 g) in acetic acid 100 ml) was added benzyltrimethylammonium dichloroiodate (3.6 g) and anhydrous zinc dichloride (2.0 g). The mixture was stirred for 18 hours. A pink precipitate formed and was isolated by filtration and washed with cold acetic acid. The solid was partitioned between diethyl ether and 2N HCl solution. The organic layer was separated, dried ($MgSO_4$) and evaporated. The residue was purified by crystallisation from dichloromethane:hexane mixtures to give the title compound (2.5 g) (mpt. 139°–140 ° C.).

EXAMPLE 33

The following compounds were prepared using a similar procedure to that described in Example 30 with the modifications described in the notes.

| Compound | R | mpt | footnote |
|---|---|---|---|
| 1 | 4-Cl | 142–143 | a |
| 2 | 4-F | 143–144 | b |
| 3 | 4-CO$_2$CH$_2$Ph | — | c |
| 4 | 4,5-(CH$_2$)$_4$- | 134–135 | b |

Notes
a:- The mixture of alkenes was converted to the title compound as follows: A mixture of 4-[3-(2-benzyloxy-4-chlorophenyl)prop-2-enyl]benzoic acid and 4-[3-(2-benzyloxy-4-chlorophenyl)-prop-1-enyl]benzoic acid (1.6 g) and 5% Pd-BaSO$_4$ (200 mg) in ethyl acetate (70 ml) was stirred under 1 atmosphere of hydrogen for 1.5 hours. The catalyst was removed by filtration and the mixture evaporated to dryness. The residue was purified by flash chromatography on silica gel eluting with diethyl ether:hexane (1:1) to give compound 1 (0.5 g).
b:- The mixture of alkenes was converted to the title compound using a similar method to that of Example 33, Footnote a.
c:- The aldehyde benzyl 4-benzyloxy-3-formylbenzoate was made from 4-hydroxy-3-formylbenzoic acid (commercially available) by method Example 1, (I) using 2 equivalents of benzyl bromide.

EXAMPLE 34

4-[3-(2-Benzyloxy-4-hydroxyphenyl)-propyl] benzoic acid

The title compound was prepared from 4-[3-(2-benzyloxy-4-methoxyphenyl)propyl]benzoic acid as follows:

To a solution of 4-[3-(2-benzyloxy-4-methoxyphenyl)-propyl]benzoic acid (0.75 g) in DMSO (20 ml) was added sodium cyanide (0.5 g). The reaction mixture was heated at 190° C. for 40 hours, cooled, partitioned between 1N aqueous NaOH and diethyl ether. The aqueous layer was separated, acidified to pH1 (conc. HCl) and extracted with ethyl acetate. The organic solution was dried ($MgSO_4$), filtered and evaporated. The residue was purified by chromatography on silica gel eluting with diethyl ether, and crystallisation from $CH_2Cl_2$/hexane mixtures to give the title compound (150 mg).

EXAMPLE 35

4-[3-(2-Benzyloxy-4-cyanophenyl)propyl]benzoic acid (A) Benzyl 4-[3-(2-hydroxy-4-cyanophenyl)propyl) benzoate was converted to the title compound by a similar method to that of Example 1, (A). The product was purified by trituration with diethyl ether. Benzyl 4-[3-(2-hydroxy-4-cyanophenyl)propyl)benzoate was prepared as follows:

4-[3-(2-Hydroxy-4-cyanophenyl)propyl)benzoic acid was converted to benzyl 4-[3-(2-benzyloxy-4-cyanophenyl) propylbenzoate by a similar method to that of Example 1, (I) using two equivalents of benzyl bromide and potassium carbonate.

(B) 4-[3-(2-Hydroxy-4-cyanophenyl)propyl)benzoic acid was obtained as follows:

To a solution of 2-benzyloxy-4-bromobenzaldehyde (11.5 g) in toluene (100 ml) was added ethanediol (3.0 ml) and p-toluene sulphonic acid (100 mg). The mixture was heated under reflux for 2 hours, cooled, washed with aqueous $NaHCO_3$ solution, dried ($MgSO_4$), filtered and evaporated to give 2-(2-benzyloxy-4-bromophenyl)-3-dioxolane as an oil (12.5 g).

(C) A mixture of 2-(2-benzyloxy-4-bromophenyl)-3-dioxolane (3.0 g) and CuCN (1.4 g) in NMP (25 ml) was heated at 150° C. The mixture was cooled, poured into diethyl ether and 2N aqueous HCl solution and stirred. The layers were separated and the organic solution dried ($MgSO_4$), filtered and evaporated. The residue was purified by chromatography on silica gel eluting with diethyl ether to give 2-benzyloxy-4-cyanobenzaldehyde (300 mg).

(D) 2-Benzyloxy-4-cyanobenzaldehyde and 4-carboxyphenethyltriphenylphosphonium bromide were converted to a mixture of 4-[3-(2-benzyloxy-4-cyanophenyl)prop-2-enyl]benzoic acid and 4-[3-(2-benzyloxy -4-cyanophenyl)prop-1-enyl]benzoic acid by a similar method to that of Example 1, (G). The alkenes were converted to the required 4-[3-(2-hydroxy-4-cyanophenyl) propyl)benzoic acid by a similar method to that of Example 33, Footnote a.

EXAMPLE 36

4-[3-(2-Benzyloxy-5-(N-methylcarbamoyl)phenyl) propyl]benzoic acid

To a 33% solution (16 ml) of methylamine in ethanol was added 4-[3-(2-benzyloxy-5-benzyloxycarbonylphenyl) propyl]benzoic acid (1.25 g). The mixture was heated at 100° C. for 12 hours in an autoclave. The solvent was evaporated and the residue extracted with ethyl acetate (100 ml) and washed with 1N aqueous HCl (100 ml) , dried ($MgSO_4$), filtered and evaporated. The residue was subjected to chromatography on silica gel, eluting with EtOAc. The title product was purified by trituration with diethyl ether (150 mg) mpt. 163°–166° C.

EXAMPLE 37

4-[3-(2-benzyloxy-6-methoxynaphthyl),propyl] benzoic acid

To a solution of 4-[3-(2-hydroxy-5,6,7,8-(tetrahydro-1-naphthyl))propyl] benzoic acid (400 mg) in ethanol (50 ml), under argon, was added (DDQ) (500 mg). The solution was stirred for 2 hours, DDQ (200 mg) was added and the mixture stirred for 18 hours. The solvent was evaporated and the residue subjected to chromatography on silica gel, eluting with diethyl ether to give the title compound (200 mg).

EXAMPLE 38

4-[3-(3-Benzyloxy-8-oxo-5,6,7,8-tetrahydro-2-naphthyl)propyl]benzoic acid

To a solution of 4-[3-(3-benzyloxy-5,6,7,8-tetrahydro-2-naphthyl) propyl]benzoic acid (1.6 g) in ethyl acetate (50 ml) was added water (1 ml) and 2,3-dichloro-5,6-dicyanobenzoquinone (1.9 g). The mixture was stirred for 2 hours, the solvent evaporated and the residue subjected to chromatography on silica gel, eluting with 0.1% formic acid in EtOAc. The residue was purified by trituration with diethyl ether to give the title compound (0.3 g) mpt. 155°–160° C.

EXAMPLE 39

4-[3-(3-Benzyloxy-8-hydroxyimino-5,6,7,8-tetrahydro-2-naphthyl)propyl] benzoic acid 4-[3-(3-Benzyloxy-8-oxo-5,6,7,8-tetrahydro-2-naphthyl) propyl] benzoic acid was converted to the title compound by a similar method to that of Example 3, Footnote q.

EXAMPLE 40

4-[3-(2-Benzyloxy-4-acetylaminophenyl)propyl] benzoic acid

Ethyl 4-[3-(2-benzyloxy-4-acetylaminophenyl)propyl] benzoate was converted to the title compound by a similar method to that of Example 1, (A) (mpt. 179°–180° C.

Ethyl 4-[3-(2-benzyloxy-4-acetylaminophenyl)propyl] benzoate was prepared as follows:

A mixture of N-(3-allyloxyphenyl)acetamide (13.2 g) prepared by a similar method to that of Example 2, Footnote c (A), from N-(3-hydroxyphenyl)acetamide, in $Ph_2O$ (100 ml) was heated at 250° C. for 10 minutes, cooled and diluted with hexane (100 ml) to give crystals. The crystals were re-crystallised from ethyl acetate. The liquors were evaporated and dissolved in 0.2M aqueous NaOH, filtered though Celite, and acidified with 1M aqueous HCl solution to give N-(4-allyl-3- hydroxyphenyl)acetamide (3.6 g) mpt. 164°–165° C.

The phenol was converted to N-(4-allyl-3-benzyloxyphenyl)acetamide by a similar method to that of Example 1, (I).

The allyl compound and ethyl 4-iodobenzoate were converted to ethyl 4-[3-(2-benzyloxy-4-acetylaminophenyl) prop-1-enyl]benzoate by a similar method to that of Example 19 (c).

The olefin was converted to ethyl 4-[3-(2-benzyloxy-4-acetylaminophenyl)propyl]benzoate by a similar method to that of Example 33, Footnote a.

EXAMPLE 41

4-[3-(2-Benzyloxy-4-benzenesulphonamidophenyl) propyl]benzoic acid

The title compound was prepared from ethyl 4-[3-(2-benzyloxy-4-benzenesulphonamidophenyl)propyl]benzoate by a similar method to that of Example 1, (A).

The ethyl ester was prepared as follows:

To a solution of $PCl_5$ (1.25 g) and pyridine (1.13 ml) in $CH_2Cl_2$ (50 ml) and −30° C. was added a solution of ethyl 4-[3-(2-benzyloxy-4-acetylaminophenyl)propyl]benzoate (2.3 g) in $CH_2Cl_2$ (10 ml). The mixture was stirred at −20° C. for 30 minutes, ethanol (3.5 ml) was added, and the mixture stirred for 30 minutes at −10° C. Water (50 ml) was added the mixture stirred for 30 minutes at ambient temperature. The Layers were separated and the organic solution washed with saturated aqueous $NaHCO_3$. The solvent was evaporated, the residue dissolved in diethyl ether and a solution of toluenesulphonic acid monohydrate (500 mg) added in ethyl acetate (10 ml). Crystals of the tosic acid salt of ethyl 4-[3-(2-benzyloxy-4-aminophenyl)propyl]benzoate were formed (0.4 g) mpt. 134°–140° C.

The aniline was converted to ethyl 4-[3-(2-benzyloxy-4-benzenesulphonamidophenyl)propyl]benzoate by a similar procedure to that of Example 3, Footnote g.

EXAMPLE 42

N-(4-Nitrophenylsulphonyl)-4-[3-(2-benzyloxyphenyl),propyl]benzamide

A mixture of 4-[3-(2-benzyloxyphenyl)propyl)benzoic acid 0.2 g), 4-nitrobenzenesulphonamide (0.12 g), DMAP (0.15 g) and 1-(3-dimethylaminopropyl)-3-ethylcarbodiimide hydrochloride (0.12 g) was stirred for 65 hours. The mixture was diluted with EtOAc, washed with water and brine, dried ($MgSO_4$), filtered and evaporated. The residue was purified by flash chromatography on silica gel, eluting with ethyl acetate, to give the title compound (0.21 g) mpt. 112°–113° C.

EXAMPLE 43

N-(Phenylsulphonyl)-4-[3-(2-benzyloxy-5-chlorophenyl)propyl]benzamide

The title compound was synthesised from 4-[3-(2-benzyloxy-5-chlorophenyl)propyl]benzoic acid by a similar method to that of Example 42.

EXAMPLE 44

4-[3-(2-Benzyloxyphenyl)propyl]-N-(2-pyridylmethyl)benzenecarboxamide.

Oxalyl chloride (3.27 g) was added dropwise to a stirred solution of 4-[3-(2-benzyloxyphenyl)propyl]benzene carboxylic acid (6 g) in methylene chloride (100 ml) containing N,N-dimethylformamide (0.1 ml). The reaction mixture was stirred at 22° C. for 16 hours, the solvent was removed and the residue issolved in methylene chloride (90 ml).

The solution of the acid chloride in methylene chloride 15 ml) (described above) was added to a stirred solution of 2-aminomethylpyridine (0.13 g) and triethylamine (0.87 g) in methylene chloride (15 ml) and the mixture was stirred at ambient temperature for 2 hours. The reaction mixture was washed twice with water (20 ml each time) and dried over anhydrous magnesium sulphate. The residue obtained on removal of the solvent was subjected to 'flash' chromotography on silica (Merck 9385) eluting with a mixture of ethyl acetate and dichloromethane (1:1 v/v) to give 4-[3-(2-benzyloxyphenyl)propyl]-N-2-(2-pyridylmethyl) benzenecarboxamide (mp 70° C.; yield 48%).

EXAMPLE 45

The procedure outlined in example 44 was repeated using the appropriate carboxylic acid and amine of R' to give the following:

$$\underset{\underset{OCH_2Ph}{|}}{\overset{R}{\underset{|}{\bigcirc}}}\;\overset{(CH_2)_n-Ar-COR'}{}$$
| Compound | Ar | n | R | R' | MP °C. | Footnote |
|---|---|---|---|---|---|---|
| 1 |  | 3 | H | —NHC(Me)₂CH₂OH | 65 | |
| 2 | " | 3 | H | —NHCH₂CH₂OH | 112 | a |
| 3 | " | 3 | H | —NHCH₂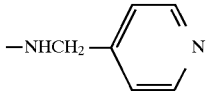 | 93 | |
| 4 | " | 3 | H | —NHCH₂CH₂OMe | 101 | |
| 5 | " | 3 | H | —NHCH₂CH₂OMe | 62–3 | |
| 6 |  | 3 | F | —NHCH₂CH₂OH | 107 | a |
| 7 | " | 3 | F | —NHC(Me)₂CH₂OH | | |
| 8 | " | 3 | F | —NHCH₂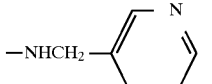 | 76 | |
| 9 | " | 3 | H | NH—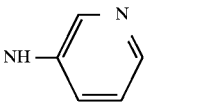 | 120–122 | |
| 10 | " | 3 | H | —NHCH₂CH₂CH₃ | 74–7 | |
| 11 | " | 2 | H | —NHCH₂CH₂OH | 102–4 | a |
| 12 | " | 2 | H | —NHCH₂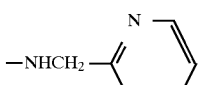 | 89–90 | |
| 13 | " | 3 | H | —NH—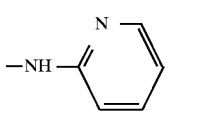 | oil | |
| 14 | " | 2 | H | —NHCH₂CH₃ | 93–4 | |
| 15 | " | 3 | H | —NHCH₂CH₂—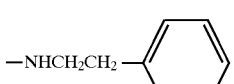 | 79–81 | |
| 16 | " | 3 | H | —NHnBu | 69 | |
| 17 | " | 3 | H | —NHiPr | 121–2 | |
| 18 | " | 3 | H | —NHMe | 109–110 | |
| 19 | " | 3 | H | —NHCH₂—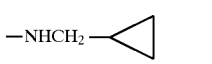 | 84 | |
| 20 | " | 3 | H | NHCH₂—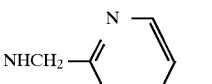 | 87 | |

-continued $$\underset{\underset{OCH_2Ph}{|}}{\overset{\overset{R}{|}}{C_6H_3}}(CH_2)_n\text{—Ar—COR'}$$

| Compound | Ar | n | R | R' | MP °C. | Footnote |
|---|---|---|---|---|---|---|
| 21 | " | 3 | H | NHCH₂–(pyrazinyl) | 100–1 | |
| 22 | " | 3 | H | NHCH₂CH₂–(1H-imidazol-4-yl) | 124–5 | |
| 23 | " | 3 | MeS | —NHCH₂CH₂CH₃ | 92 | |
| 24 | " | 2 | NO₂ | —NHCH₂CH₂OH | 134–5 | |
| 25 | " | 2 | NO₂ | NHCH₂–(2-pyridyl) | 117–8 | |
| 26 | " | 2 | NO₂ | NHCH₂–(3-pyridyl) | 156–8 | |
| 27 | " | 2 | Br | —NHCH₂CH₂OH | 143–4 | |
| 28 | " | 2 | Br | —NHCH₂–(2-pyridyl) | 123–4 | |
| 29 | " | 2 | Br | —NHCH₂–(3-pyridyl) | 162–3 | |
| 30 | " | 2 | CN | —NHCH₂CH₂OH | 115–6 | |
| 31 | " | 2 | CN | —NHCH₂–(2-pyridyl) | 129–30 | |
| 32 | " | 2 | CN | —NHCH₂–(3-pyridyl) | 160–1 | |
| 33 | " | 3 | Br | —NHCH₂CH₂OH | 112–3 | |
| 34 | " | 3 | Br | —NHCH₂–(2-pyridyl) | 107–8 | |
| 35 | " | 3 | Br | —NHCH₂–(3-pyridyl) | 130–1 | |
| 36 | " | 3 | CN | —NHCH₂CH₂OH | 132–3 | |
| 37 | " | 3 | CN | —NHCH₂–(2-pyridyl) | 137–8 | |

-continued

Structure: R-(CH₂)ₙ-Ar-COR' with OCH₂Ph substituent on benzene ring

| Compound | Ar | n | R | R' | MP °C. | Footnote |
|---|---|---|---|---|---|---|
| 38 | " | 3 | CN | —NHCH₂-(2-pyridyl) | 110–111 | |
| 39 | " | 3 | Cl | —NHCH₂-(3-pyridyl) | 135–135.5 | |
| 40 | " | 3 | Cl | —NHCH₂CH₂CH₃ | 94.5–95.5 | |
| 41 | " | 3 | H | —NHEt | 114–5 | |
| 42 | " | 3 | NO₂ | —NHCH₂CH₂OH | 127–9 | |
| 43 | " | 3 | NO₂ | —NHCH₂-(2-pyridyl) | 109–111 | |
| 44 | " | 3 | NO₂ | —NHCH₂-(3-pyridyl) | 149–150 | |
| 45 | " | 3 | CH₃CO— | —NHCH₂CH₂OH | 115–7 | |
| 46 | " | 3 | CH₃CO— | —NHCH₂-(2-pyridyl) | 155–6 | |
| 47 | " | 3 | CH₃CO— | —NHCH₂-(3-pyridyl) | 135–7 | |
| 48 | " | 3 | CH₃CO— | —NHCH₂CH₂CH₃ | 109–110 | |
| 49 | " | 3 | H | —NHCH₂CH₂NH₂ | 110 | |
| 50 | " | 3 | H | —NHCH₂CH₂NHCOMe | 147–149 | |
| 51 | " | 3 | H | —NHCH₂COOEt | Gum | |
| 52 | " | 3 | H | NHCH₂CH₂COOEt | Gum | |
| 53 | " | 3 | H | —NH-(tetrazolyl) | 255 | |
| 54 | " | 3 | H | —NHCH₂-cyclopropyl | 84 | |
| 55 | " | 3 | H | —NHCH₂-(pyrimidinyl) | 87 | |
| 56 | " | 3 | H | —NH-cyclobutyl | 104 | |
| 57 | " | 3 | —SMe | —NHCH₂-(2-pyridyl) | 124 | |

-continued $$\underset{\underset{OCH_2Ph}{|}}{R} \diagdown \underset{}{\bigcirc} \diagup (CH_2)_n-Ar-COR'$$

| Compound | Ar | n | R | R' | MP °C. | Footnote |
|---|---|---|---|---|---|---|
| 58 | " | 3 | —SMe | —NH—◁ | 105 | |
| 59 | " | 3 | —SMe | —NHCH₂-(3-pyridyl) | 123 | |
| 60 | " | 3 | —SO₂Me | —NHCH₂CH₂OH | 129–130 | |
| 61 | " | 3 | —SO₂Me | —NHCH₂-(2-pyridyl) | 146–148 | |
| 62 | " | 3 | —SO₂Me | —NHCH₂-(3-pyridyl) | 158–159 | |
| 63 | " | 3 | H | —NHNH-(2-pyridyl) | — | |
| 64 | " | 3 | H | —NHCH₂CF₂CF₃ | 110 | |
| 65 | " | 3 | H | —NHCH₂CH₂-(1-Me-imidazol-5-yl) | 83–85 | |
| 66 | " | 3 | H | —NHCH₂CH₂-(1-Me-imidazol-4-yl) | 95–98 | |
| 67 | " | 3 | H | —NHCH₂CH₂—N(imidazol-1-yl) | 74–78 | |
| 68 | " | 4 | H | —NHCH₂-(2-pyridyl) | 71 | |
| 69 | " | 4 | H | —NHCH₂CH₂OH | 52 | |
| 70 | " | 4 | H | —NHCH₂CH₂CH₃ | 54 | |
| 71 | " | 3 | H | —NHCH₂CH₂N(imidazol-1-yl) | 106 | |
| 72 | (thiazolyl) | 3 | H | —NHCH₂CH₂OH | — | |
| 73 | " | 3 | H | —NHCH₂-(2-pyridyl) | — | |

-continued $$\underset{\text{OCH}_2\text{Ph}}{\text{R}}\text{C}_6\text{H}_3\text{-(CH}_2)_n\text{-Ar-COR'}$$

| Compound | Ar | n | R | R' | MP °C. | Footnote |
|---|---|---|---|---|---|---|
| 74 | 2,5-dimethyl-OMe-phenyl | 2 | H | —NHCH$_2$CH$_2$CH$_3$ | 96–97 | |
| 75 | " | 2 | H | —NHCH$_2$-(2-pyridyl) | 69–70 | |
| 76 | " | 2 | H | —NHCH$_2$-(3-pyridyl) | 88–89 | |
| 77 | " | 2 | H | —NHCH$_3$ | 111–112 | |
| 78 | " | 2 | Br | —NHCH$_2$CH$_2$CH$_3$ | 102–103 | |
| 79 | " | 2 | Br | —NHCH$_2$-(3-pyridyl) | 95–98 | |
| 80 | " | 2 | Br | —NHCH$_2$CH$_2$OH | 96–98 | |
| 81 | " | 2 | Br | —NHCH$_2$-(2-pyridyl) | 159–160 | |
| 82 | " | 3 | H | —NHCH$_2$CH$_2$OH | 101–102 | |
| 83 | " | 3 | H | —NHCH$_2$-(2-pyridyl) | — | |
| 84 | " | 3 | H | —NHCH$_2$-(3-pyridyl) | — | |
| 85 | " | 3 | H | —NHCH$_2$CH$_2$CH$_3$ | — | |
| 86 | thienyl (S) | 3 | H | —NHCH$_2$CH$_2$OH | 112 | |
| 87 | " | 3 | H | —NHCH$_2$-(2-pyridyl) | — | |
| 88 | " | 3 | H | —NHCH$_2$-(3-pyridyl) | — | |
| 89 | phenyl | 3 | H | —NHCH$_2$-(pyridazinyl) | 134–135 | |
| 90 | " | 3 | H | —NHCH$_2$CH$_2$SEt | 63–65 | |

-continued
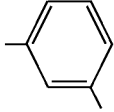
| Compound | Ar | n | R | R' | MP °C. | Footnote |
|---|---|---|---|---|---|---|
| 91 | " | 3 | H | —NHCH₂CN | 100–102 | |
| 92 | 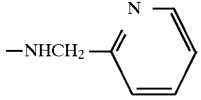 | 3 | H | —NHCH₂CH₂OH | — | |
| 93 | " | 3 | H | 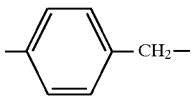 | — | |
| 94 | 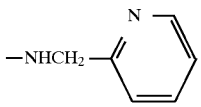 | 2 | H | —NHCH₂CH₂OH | 128–129 | |
| 95 | " | 2 | H | 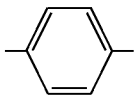 | 114–115 | |
| 96 | " | 2 | H | —NHCH₂CH₂CH₃ | 112–115 | |
| 97 | 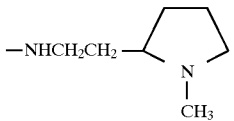 | 3 | H | 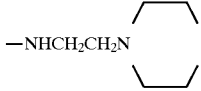 | 66–69 | |
| 98 | " | 3 | H | 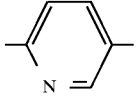 | 93–94 | |
| 99 | 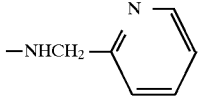 | 2 | H | 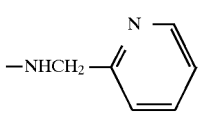 | 95–99 | |
| 100 | " | 2 | H | —NHCH₂CH₂OH | 133–134 | |
| 101 | " | 2 | H | —NHCH₂CH₂CH₃ | 68–72 | |
| 102 | " | 3 | H | 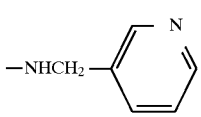 | — | |
| 103 | " | 2 | H | 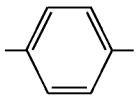 | 175–176 | |
| 104 | 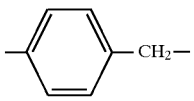 | 3 | H | —NHCH₂CH₂CH₂OH | 75–79 | |
| 105 | 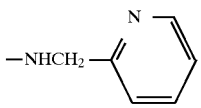 | 3 | H | 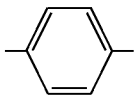 | 78–80 | |
| 106 | " | 3 | H | —NHCH₂CH₂OH | 79–83 | |
| 107 | " | 3 | H | —NHCH₂CH₂CH₃ | 71–74 | |

-continued
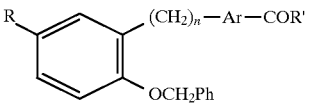
| Compound | Ar | n | R | R' | MP °C. | Footnote |
|---|---|---|---|---|---|---|
| 108 | " | 2 | Br | 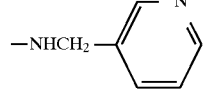 | 195–197 | |
| 109 | " | 2 | Br | —NHCH$_2$CH$_2$CH$_3$ | 140–144 | |
| 110 | " | 2 | Br | —NHCH$_2$CH$_2$OH | 139–143 | |
| 111 | 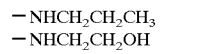 | 2 | H | 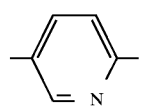 | — | |
| 112 | 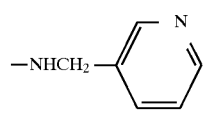 | 3 | H | " | 108–111 | |
| 113 | 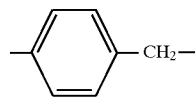 | 2 | —SMe | —NHCH$_2$CH$_2$CH$_3$ | 108–110 | |
| 114 | " | 2 | —SMe | —NHCH$_2$CH$_2$OH | 110–112 | |
| 115 | " | 2 | —SMe | 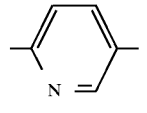 | 54–56 | |
| 116 | " | 2 | —SO$_2$Me | 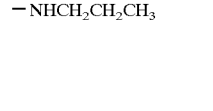 | 184–186 | |
| 117 | " | 2 | —Br | 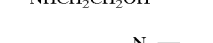 | 137–139 | |
| 118 | " | 2 | —SO$_2$Me | —NHCH$_2$CH$_2$CH$_3$ | 167–168 | |
| 119 | 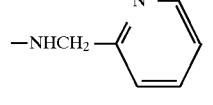 | 2 | Br | 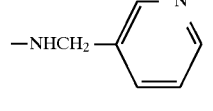 | 227–229 | |
| 120 | 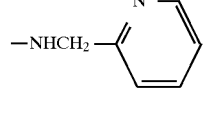 | 2 | Br | —NHCH$_2$CN | 226–228 | |
| 121 | 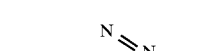 | 2 | Br | —NHCH$_2$CN | 132–134 | |
| 122 | " | 2 | Br | —NHCH$_2$CH$_2$CH$_3$ | 68–70 | |
| 123 | " | 2 | Br | —NHCH$_2$CH$_2$OH | 106–108 | |

-continued

Structure: R-(benzene with OCH₂Ph)-(CH₂)ₙ-Ar-COR'

| Compound | Ar | n | R | R' | MP °C. | Footnote |
|---|---|---|---|---|---|---|
| 124 | " | 2 | Br | —NHCH₂-(2-pyridyl) | 135–137 | |
| 125 | " | 2 | Br | —NHCH₂-(3-pyridyl) | 76–78 | |
| 126 | 1-methyl-2-oxo-pyridinyl | 2 | Br | —NH-(tetrazolyl) | 250–253 | |
| 127 | 1,4-phenylene | 3 | —CH₂OMe | —NHCH₂CH₂CH₃ | 81.5–84 | |
| 128 | " | 3 | oxazolyl | —NHCH₂CH₂CH₃ | 130–131.5 | |
| 129 | " | 3 | H | —NEt₂ | Oil | |
| 130 | " | 3 | H | NH₂ | 133–134 | |
| 131 | " | 3 | NO₂ | NH₂ | 168–169 | |
| 132 | " | 3 | NO₂ | —CH₂-(pyridyl) | 149–150 | |

EXAMPLE 46

The procedure outlined in example 44 was repeated using the appropriate carboxylic acid and amine to give the following:

Structure: benzene (positions 3,4,5,6 labeled) with R at 3, OCH₂Ph at 2, X—Ar—CONHR' at 1

| Compound | R | X | Ar | R1 | mpt |
|---|---|---|---|---|---|
| 1 | H | (E)CH=CH | pyridyl | —CH₂-(3-pyridyl) | 159–161 |
| 2 | H | (E)CH=CH | " | —CH₂CH₂CH₃ | 126–127 |
| 3 | H | (E)CH=CH | " | —CH₂-(2-pyridyl) | 120–122 |

-continued

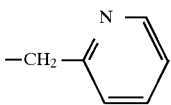

| Compound | R | X | Ar | R1 | mpt |
|---|---|---|---|---|---|
| 4 | 5-Br | (E)CH=CH | " | " | 144–148 |
| 5 | 5-Br | (E)CH=CH | " | —CH₂CH₂OH | 151–153 |
| 6 | 5-SMe | (E)CH=CH | " | —CH₂-(pyridyl) | 120–122 |
| 7 | 5-SMe | (E)CH=CH | " | —CH₂CH₂CH₃ | 144–147 |
| 8 | 5-SMe | (E)CH=CH | " | —CH₂CH₂OH | 125–128 |

EXAMPLE 47

4-[3-(2-Benzyloxy-5-methylthiophenyl)propyl]-N-(2-hydroxyethyl)benzene carboxamide (A) A mixture of methyl 4-[3-(2-benzyloxy-5-methylthiophenyl)-propyl]benzoate (0.55 g) and 2-aminoethanol (0.24 g) was stirred and heated at 140° C. for 2 hours. The cooled reaction mixture was subjected to chromatography on silica (Merck type 9385) eluting with ethyl actate. The required fractions were evaporated to dryness and the residue was triturated with diethyl ether to give 4-[3-(2-benzyloxy-5-methylthio)propyl]-N-(2-hydroxyethyl)benzenecarboxamide hemihydrate (mp 110°–112° C.; yield 53%)

The starting material was prepared as follows:

(B) The 4-[3-(2-benzyloxy-4-methylthio)propyl]-benzenecarboxylic acid was prepared from the corresponding 2-benzyloxy-4-methylthiobenzaldehyde. The 2-benzyloxy-4-methylthiobenzaldehyde was prepared by standard means from 2-hydroxy-4-methylthiobenzaldehyde, the preparation of which is described in Bull. Chem. Soc. Jap. 51 2435 1968.

EXAMPLE 48

4-[3-(2-Benzyloxy-5-methylsulphinylphenyl)propyl]-N-(2-hydroxyethyl)benzene carboxamide A slurry of 4-[3-(2-benzyloxy-5-methylthiophenyl)-propyl]-N-(2-hydroxyethyl)benzenecarboxamide (0.22 g) in methanol (10 ml) was added to a stirred solution of sodium metaperiodate (0.113 g) in water (1 ml) maintained at 0° C. by external cooling. The reaction mixture was stirred at 0° C. for 2 hours, then concentrated to a volume of approximately 2 ml. This residue was dissolved in ethyl acetate (10 ml), the ethyl acetate solution was dried (anhydrous magnesium sulphate) and the solution evaporated to dryness. The residue was subjected to chromatography on silica (Merck) eluted with a mixture of methanol/ethyl acetate (1:9 v/v). The only porduct obtained was triturated with ethyl acetate (2 ml) to give 4-[3-(2-benzyloxy-5-methylsulphinylphenyl)propyl]-N-(2-hydroxyethyl)-benzenecarboxamide (mp. 105°–108° C.; 43% yield).

EXAMPLE 49

4-[3-(2-Benzyloxy-5-methylsulphonylphenyl)propyl]-N-propylbenzene carboxamide

A mixture of 4-[3-(2-benzyloxy-5-methylthiophenyl)propyl]-N-propylbenzenecarboxamide (0.7 g) and metachloroperbenzoic acid (1.22 g) in methylene chloride (20 ml) was stirred at ambient temperature for 18 hours. The reaction mixture was washed four times with saturated aqueous sodium bicarbonate solution (20 ml each time), dried and evaporated to dryness. The residue was subjected to chromatography on silica (Merck 9385), eluting with a mixture of ethyl acetate and methylene chloride (1:9 v/v) to give 4-[3-(2-benzyloxy-5-methylsulphonylphenyl)propyl]-N-propylbenzenecarboxamide (mp. 121°–122 0° C.; yield 29%).

EXAMPLE 50

4-[3-(5-Amino-2-benzyloxyphenyl)ethyl]-N-(2-hydroxyethyl)benzene carboxamide

A mixture of 4-[3-(2-benzyloxy-5-nitrophenyl)ethyl]-N-(2-hydroxyethyl)benzenecarboxamide (0.5 g) and stannous chloride dihydrate (2.15 g) in ethanol (50 ml) was heated at 70° C. for 4 hours, and then stirred at ambient temperature for 16 hours. The reaction mixture was poured onto crushed ice and the pH adjusted to 8 with saturated aqueous sodium bicarbonate solution. The basic aqueous solution was extracted three times with ethyl acetate (50 ml each time) and the extracts were dried (MgSO₄). The solid obtained on removal of the solvent was subjected to 'flash' chromatography on silica (Merck 9385) eluting with ethyl acetate initially then a mixture of methanol and ethyl acetate (1:9 v/v) to give 4-[3-(5-amino-2-benzyloxyphenyl)ethyl]-N-(2-hydroxyethyl)benzenecarboxamide (mp. 127°–8° C.; yield 65%).

EXAMPLE 51

The procedure outlined in Example 50 was repeated using the appropriate 4-[3-(2-benzyloxy-5-nitrophenyl)alkyl]-N-substituted benzene-carboxamide to give:

| Compound | n | R | m.p | Footnote |
|---|---|---|---|---|
| 1 | 2 | —CH₂—(3-pyridyl) | 127–8 | a |
| 2 | 2 | —CH₂—(2-pyridyl) | 52–4 | b |
| 3 | 3 | —CH₂CH₂OH | 79–82 | c |
| 4 | 3 | —CH₂—(3-pyridyl) | 52–3 | d |
| 5 | 3 | —CH₂—(2-pyridyl) | 118–9 | e |
| 6 | 3 | H | 86–87 | |

Footnotes
(a) Prepared from example 45 compound 25.
(b) Prepared from example 45 compound 26.
(c) Prepared from example 45 compound 42.
(d) Prepared from example 45 compound 43.
(e) Prepared from example 45 compound 44.

EXAMPLE 52

4-[3-(2-Benzyloxy-5-(1-hydroxyiminoethyl)phenyl)propyl]-N-(2-hydroxyethyl)-benzene carboxamide A mixture of 4-[3-(5-acetyl-2-benzyloxyphenyl)propyl]-N-(2-hydroxyethyl)benzenecarboxamide (0.5 g) (example 2, compound 45) hydroxylamine hydrochloride (0.16 g) in pyridine (5 ml) was heated at 60° C. for 2 hours. The pyridine was removed and the residue subjected to flash chromatography on silica, eluting with a mixture of ethyl acetate/hexane (4:1 v/v) to yield in the appropriate fractions, 4-[3-(2-benzyloxy-5-(1-hydroxyiminoethyl)phenyl)propyl]-N-(2-hydroxyethyl)benzenecarboxamide (m.p. 131°–2° C.; yield 56%).

EXAMPLE 53

The procedure outlined in example 52 was repeated using the appropriate 4-[3-(5-acetyl-2-benzyloxyphenyl)propyl]-N-substituted benzenecarboxamide to give:

| Compound | R | M.p. °C. | Starting material |
|---|---|---|---|
| 1 | —CH₂—(3-pyridyl) | 170–20 | Example 45, compound 47 |
| 2 | —CH₂—(2-pyridyl) | 139–141 | |
| 3 | Pr$^n$ | 140–141 | Example 45, compound 48 |

EXAMPLE 54

4-[3-(2-Benzyloxyphenyl)propyl]-N-(4-imidazolyl)-2-ethyl)benzenecarboxamide

A mixture of 4-[3-(2-benzyloxyphenyl)propyl]-benzenecarboxylic acid (13.7 g), diphenylphosphoryl azide (10.9 g) and triethylamine (28 ml) in methylene chloride (500 ml) was stirred at ambient temperature for 1 hour. Solid histamine dihydrochloride was added and the reaction mixture was stirred for 16 hours. The reaction mixture was washed three times each with water (100 ml each time) and 2N sodium hydroxide solution (100 ml each time) and dried. The residue obtained on evaporation of the solvent was subjected to chromatography on silica, eluting with ethyl acetate and then with an ethyl acetate/methanol mixture (4:1 v/v). Concentration of the appropriate fractions yielded 4-[3-(2-benzyloxyphenyl)-propyl-N-(4-(imidazolyl)-2-ethyl)benzenecarboxamide [m.p. 124–5; yield 3.6 g (20%)].

EXAMPLE 55

(E)-4-[2-(2-Benzyloxyphenyl)ethenyl]-N-(2-hydroxyethyl)benzenecarboxamide (A) A solution of 4-[2-(2-benzyloxyphenyl)ethenyl]-benzenecarbonyl chloride (0.98 g) in dichloromethane (5 ml) was added dropwise to a solution of 2-aminoethanol (0.51 ml) in dichloromethane (15 ml) maintained at 0° C. The reaction mixture was allowed to warm to ambient temperature and was stirred for 16 hours. The reaction mixture was washed with water (20 ml) and saturated aqueous sodium bicarbonate (20 ml) and dried. Evaporation of the solvent left a solid residue which was crystallised twice from methanol to give (E)-4-[2-(2-benzyloxyphenyl)ethenyl]-N-(2-hydroxyethyl)benzenecarboxamide (m.p. 149°–151° C.; yield 19%) containing about 4% of the related Z-isomer.

(B) The methanol filtrates from the crystallisation described above were combined and evaporated to dryness to give a 5:1 mixture of Z:E 4-{2-(2-benzyloxyphenyl)ethenyl]-N-(2-hydroxyethylbenzene-carboxamide (m.p. 87–93° C.; yield 38%).

(C) Using the same procedure with 2-aminomethylpyridine as the amine component there was obtained 4-[2-(2-benzyloxyphenyl)ethenyl]-N-(2-pyridylmethyl)benzene carboxamide as a 13:1 mixture of E:Z isomers (m.p. 123°–127°; yield 18%) and 4-[2-(2-benzyloxyphenyl)ethenyl]-N-(2-pyridylmethyl)benzene carboxamide as a 7:1 mixture of Z:E isomers as a viscous gum (yield 21%).

(D) The 4-[2-(2-benzyloxyphenyl)ethenyl]benzenecarbonyl chloride used as starting material was prepared from the corresponding carboxylic acid and oxalyl chloride as described in example 1 and was used without further purification.

EXAMPLE 56

4-[3-(2-Benzyloxyphenyl)propyl]-N-(2-pyridylmethylcarbonyl)benzamine (A) Diphenylphosphoryl azide (0.46 ml) was added dropwise to a stirred suspension of 2-pyridylacetic acid (0.367 g) and triethylamine (0.3 ml) in N,N-dimethylformamide (10 ml) maintained at 0° C. A suspension of 4-[3-(2-benzyloxyphenyl)propyl]benzeneamine hydrochloride (0.75 g) in N,N-dimethylformamide (10 ml) containing triethylamine (0.9 ml) was added rapidly to the reaction mixture. Stirring was continued at ambient temperature for 16 hours and the reaction mixture was concentrated to small volume. The residue was partitioned between water and diethyl ether. The diethyl ether extract was washed once each with saturated aqueous sodium bicarbonate (20 ml) and brine (20 ml) and dried. The gum obtained on removal of the solvent was subjected to chromatography on silica (Merck 9385) eluted with a mixture of ethyl acetate and hexane (1:1 v/v). The gum obtained was triturated with ether at 0° C. to give 4-[3-(2-benzyloxy-phenyl)propyl]-N-(2-pyridylmethylcarbonyl)benzeneamine (m.p. 61°–2° C.; yield 0.63 g 68%).

(B) In the like manner using the appropriate carboxylic acid there was prepared 4-[3-(2-benzyloxyphenyl)propyl]-N-(3-pyridylmethylcarbonyl)benzeneamine (m.p. 99°–100° C.; yield 0.90 g 72%).

The 4-[3-(2-benzyloxyphenyl)propyl]benzeneamine used as starting material was prepared as follows:

(C) A mixture of 4-[3-(2-benzyloxyphenyl)propyl]benzene carboxylic acid (8.39 g), diphenylphosphoryl azide (5.74 ml) and triethylamine (7.1 ml) in t-butanol (80 ml) was heated under reflux in an argon atmosphere for 16 hours. The reaction mixture was evaporated to dryness and the residue partitoned between ethyl acetate and water. The ethyl acetate extract was washed once each with 2N HCl, water, saturated aqueous sodium bicarbonate solution and brine (20 ml each time) and dried (MgSO4). The solvent was evaporated and the residue subjected to flash chromatography eluted with a mixture of dichloromethane:hexane (1:1 v/v) to give N t-butyloxycarbonyl-4-{3-(2-benzyloxyphenyl)propyl]benzene-amine 7.69 g m.p. 86°–8° C. which was used directly in the next step.

(D) A solution of N-t-butoxycarbonyl-4-[3-(2-benzyloxyphenyl)-propyl]benzeneamine in chloroform (50 ml) was treated with trimethyl-silyl iodide (3.8 ml) at 0° C. and then stirred at ambient temperature for 10 minutes. The solvent was concentrated and the oily residue was dissolved in diethyl ether and washed consecutively with saturated aqueous sodium bicarbonate (50 ml) and water (50 ml). The diethyl ether solution was shaken with 3N aqueous HCl and the 4-[3-(2-benzyloxphenyl)propyl]benzeneamine hydrochloride was collected. Yield=5.94 g (91%).

EXAMPLE 57

4-[3-(2-Benzyloxyphenyl)propyl]-N-(3-methoxypropionyl)-benzeneamine

Oxalyl chloride (0.41 ml) was added to a stirred solution of 3-methoxypropanoic acid (0.45 ml) in methylene chloride (15 ml) containing 1 drop of N,N-dimethylformamide. The mixture was stirred at ambient temperature for 3 hours. A 5 ml aliquot of this reaction mixture was added dropwise to a solution of 4-[3-(2-benzyloxyphenyl)-propyl]-benzeneamine hydrochloride (0.63 g) in dichloromethane (20 ml) containing triethylamine (0.82 ml). Stirring was continued for 16 hours. The reaction mixture was evaporated to dryness and the residue was partitioned between diethyl ether and water. The diethyl ether extract was washed consecutively with aqueous 2N HCl (20 ml), saturated aqueous sodium bicarbonate (20 ml) and brine (20 ml) then dried (MgSO$_4$). The residue obtained on removal of the solvent was subjected to flash chromatography on silica (Merck 9385) eluted with ether, to give, after crystallisation from diethyl ether-hexane mixture, 4-[3-(2-benzyloxyphenyl)propyl]-N-(3-methoxypropionyl)-benzeneamine, m.p. 65°–6° C., yield 0.58 g (80%).

EXAMPLE 58

Using the procedure described in example 57 and the appropriate acid (RCO$_2$H) and 4-[3-(2-benzyloxyphenyl)propyl]benzeneamine hydrochloride there was prepared:

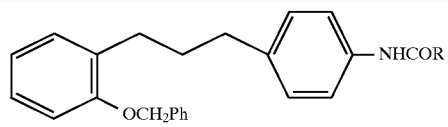

| Compound | R | pt | Footnote |
|---|---|---|---|
| 1 | —CH$_2$—(pyridyl) | 119–121 | |
| 2 | nPr | 98–99 | |
| 3 | —CH$_2$CH$_2$CO$_2$H | 138–139 | a |
| 4 | —CH$_2$—(succinimidyl) | 174–177 | b |

Notes
(a): -Mono-methylsuccinate was used to prepare the intermediate N-(4-(3-(2-benzyloxyphenyl)propyl)phenyl]-2-(methoxycarbonyl) propionam ide. This was hydrolysed to the corresponding carboxylic acid using a similar method to that of Example 1 (A).
(b): -The acid component was coupled to the benzeneamine using a similar method to that of Example 71.

EXAMPLE 59

4-[3-(2-benzyloxyphenyl)propyl]-N-[3-hydroxypropionyl]benzene amine

Propiolactone (0.23 ml) was added to a mixture of 4-[3-(2-benzyloxyphenyl]propyl]benzeneamine hydrochloride (1.26 g) and triethylamine (0.5 ml) in methylene chloride (10 ml) and the mixture was stirred for 18 hours. A further equivalent of propiolactone (0.23 ml) was added and stirring continued for a further 24 hours. The reaction mixture was concentrated and the residue was subjected to flash chromatography on silica eluted with a stepwise gradient of methanol in methylene chloride. The fractions eluting with 5% methanol in methylene chloride were collected, concentrated and subjected to chromatography again, eluting with ethyl acetate to give, after crystallisation from dichloromethane/hexane (1:20 v/v) 4-[3-(2-benzyloxyphenyl)propyl]-N-(3-hydroxypropionyl)]benzeneamine m.p. 109°–110°, 0.22 g (15%).

EXAMPLE 60

A similar procedure to that outlined in example 47 was repeated with the appropriate carboxylic ester and amine to give the compounds listed in the table. Reactions with ethanolamine were carried out neat. Ethanol was used as a solvent for other amines.

Structure: R—[benzene ring with (CH$_2$)$_n$—Ar—CONHR' substituent and OCH$_2$Ph substituent]

| Compound | Ar | n | R | R$^1$ | mpt °C. | footnote |
|---|---|---|---|---|---|---|
| 1 | 1,2,4-triazine (N—N, N, NH) | 2 | H | —CH$_2$CH$_2$OH | 169–170 | a |
| 2 | " | 2 | H | —CH$_2$-(2-pyridyl) | 121–124 | |
| 3 | pyridazine (N=N) | 2 | H | —CH$_2$CH$_2$CH$_3$ | 79–80 | |
| 4 | " | 2 | H | —CH$_2$-(2-pyridyl) | 72–74 | |
| 5 | " | 2 | H | —CH$_2$-(2-pyridyl) | 138–139 | |
| 6 | phenyl-OH | 2 | H | —CH$_2$CH$_2$OH | 101–102 | |
| 7 | " | 2 | H | —CH$_2$-(2-pyridyl) | 133–134 | |
| 8 | " | 2 | H | —CH$_2$-(2-pyridyl) | 174–175 | |
| 9 | " | 2 | H | CH$_3$ | 114–115 | |
| 10 | phenyl-OMe | 2 | H | —CH$_2$CH$_2$OH | 64–66 | |

-continued

R—[benzene ring with (CH₂)ₙ—Ar—CONHR' and OCH₂Ph substituents]

| Compound | Ar | n | R | R¹ | mpt °C. | footnote |
|---|---|---|---|---|---|---|
| 11 | [phenyl with OH] | 2 | Br | —CH₂CH₂CH₃ | 82–83 | |
| 12 | " | 2 | Br | —CH₂CH₂OH | 138–139 | |
| 13 | [phenyl with OH] | 2 | Br | —CH₂-(pyridyl) | 175–176 | |
| 14 | " | 2 | Br | —CH₂-(pyridyl) | 197–198 | |
| 15 | " | 3 | H | —CH₂CH₂CH₃ | 64–65 | |
| 16 | " | 3 | H | —CH₂CH₂OH | 101–102 | |
| 17 | " | 3 | H | —CH₂-(pyridyl) | 91–92 | |
| 18 | " | 2 | SMe | —CH₂CH₂CH₃ | 59–60 | |
| 19 | " | 2 | SMe | —CH₂-(pyridyl) | 150–151 | |
| 20 | " | 2 | SMe | —CH₂-(pyridyl) | 174–176 | |

Footnotes
a: A mixture of methyl 3-(2-benzyloxyphenyl)propionate (2.95 g; and hydrazine hydrate (1.0 ml) was heated at refulx in ethanol (30 ml) for 24 hours. The mixture was cooled and a solid crystallised (1.82 g). The solid (1.0 g) and ethyl aminothioxoacetate (0.5 g) were heated together at 120° C. for 15 minutes under reduced pressure to give a white solid (0.74 g) after washing with ethanol. This material was heated at 210° C. for 15 minutes to give ethyl 5-[2-benzyloxyphenethyl]-1,2,4-triazol-3-ylcarboxylate (0.41 g) after purification be flash chromatography, eluting with diethyl ether.

EXAMPLE 61

N-Propyl-4-[3-(2-benzyloxy-5-methanesulphinylphenyl)propyl]benzamide was prepared by oxidising the corresponding methylthio compound (compound 23, Example 45) using a similar method to that described in footnote u of Example 3 mpt. 101°–102° C.

EXAMPLE 62

N-Cyclopropyl-4-[3-(2-benzyloxy-5-methanesulphinylphenyl)propyl]benzamide was prepared by oxidising the corresponding methylthio compound (compound 58, example 45) using a similar method to that described in footnote u of example 2 mpt. 107°–108° C.

EXAMPLE 63

The processes described in example 56 were repeated using the appropriate carboxylic acids to give the following:

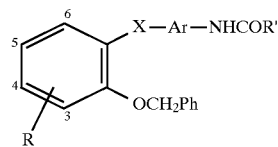

| Compound | R | X | Ar | R[1] | mpt °C. |
|---|---|---|---|---|---|
| 1 | H | (E)CH=CH | -CH2-pyridyl | -CH2-pyridyl | 142–145 |
| 2 | H | CH2CH2 | " | " | 160–162 |
| 3 | 5-NO2 | -(CH2)3- | -phenylene- | " | 155–156 |

EXAMPLE 64

The process described in example 54 was repeated using the appropriate carboxylic acids and amines to give the follow:

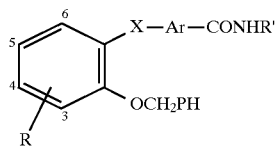

| Compound | R | X | Ar | R[1] | mpt (°C) |
|---|---|---|---|---|---|
| 1 | 5-SOMe | (CH2)3 | -phenylene- | -CH2-pyridyl | 136–137 |
| 2 | 5-SOMe | (CH2)3 | " | -CH2-pyridyl | 138 |
| 3 | H | (CH2)3 | " | -(CH2)3-imidazolyl | — |
| 4 | H | (CH2)3 | pyridyl | -CH2CH2OH | — |
| 5 | H | (CH2)3 | " | -CH2CH2CH3 | 66–68 |
| 6 | H | (CH2)3 | " | -CH2-pyridyl | 75–80 |
| 7 | 6-OH | (CH2)3 | -phenylene- | " | 172–174 |
| 8 | 6-OH | (CH2)3 | " | -CH2CH2OH | 105 |

EXAMPLE 65

N-(2Hydroxyethyl)-N-methyl-4-[3-(2-benzyloxphenyl)propyl]benzamide 1-(3-Dimethylaminopropyl)-3-ethylcarbodiimide hydrochloride (1.21 g) was added to a mixture of 4-[3-(2-benzyloxyphenyl)propyl]benzene carboxylic acid (2 g) and triethylamine (1.75 g) in methylene chloride (20 ml). The reaction mixture was stirred for 20 minutes at 20° C., and 2-methylaminoethanol (0.86 g) was added. The reaction mixture was stirred at 20° C. for 16 hours, washed with water (50 ml) and dried (MgSO$_4$). The residue obtained on removal of solvent was subjected to 'flash' chromatography on silica, eluting with ethyl acetate to give N-(2-hydroxyethyl)-N-methyl-4-[3-(2-benzyloxyphenyl)propyl] benzamide as a gum (yield 19%).

EXAMPLE 66

N-(2-Chloroethyl)-4-(3-(2-benzyloxyphenyl)propyl] benzamide

A similar process to that of Example 2, Footnote c (C), was repeated with example 53 compound 2 to give N-(2-chloroethyl)-4-(3-(2-benzyloxyphenyl)propyl]benzamide.

EXAMPLE 67

2-(3-[4-(3-(2-Benzyloxyphenyl)propyl)phenyl]ureido)ethanol

A similar process to that of Example 64 (C) was repeated, except that the t-butanol was replaced by ethanolamine, to give 2-(3-[4-(3-(2-benzyloxyphenyl)propyl)phenyl]ureido)ethanol.

EXAMPLE 68

A similar procedure to that outlined in Example 54 was repeated using compound 19 from Example 28 and the appropriate amine to give the following:

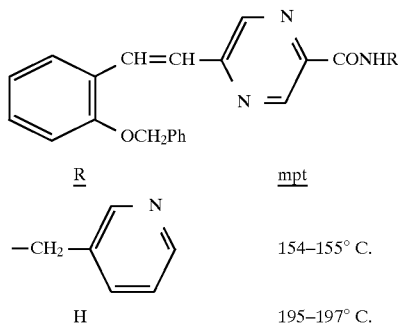

| R | mpt |
|---|---|
| —CH$_2$—(pyridyl) | 154–155° C. |
| H | 195–197° C. |

EXAMPLE 69

1,3-Dimethyl-4-[2-(4-[3-(2-benzyloxyphenyl)propyl]benzylamino)ethyl]imidazolium iodide A mixture of N-[2-(imidazol-4-yl)ethyl]-4-[3-(2-benzyloxyphenyl)propyl]benzamide (2.2 g) iodomethane (0.71 g) and potassium carbonate (1.38 g) were stirred in DMF (10 ml) for 18 hours. A further quantity of iodomethane (0.3 g) was added and the mixture was stirred for 18 hours. The solvent was evaporated and the residue purified by subjecting to chromatography on silica, eluting with methanol: CH$_2$Cl$_2$ (72:25), to give 1,3-dimethyl-4-[2-(4-[3-(2-benzyloxyphenyl)propyl]benzylamino)ethyl] imidazolium iodide as a gum (1.4 g).

EXAMPLE 70

1-Ethyl-3-[2-(4-[3-(2-benzyloxyphenyl)propyl] benzylamino)ethyl]pyridinium iodide A mixture of N-(2-(3-pyridyl)ethyl)-4-[3-(2-benzyloxyphenyl) propyl]benzamide(1 g) and ethyl iodide (0.54 g) was stirred in DMF (5 ml) at 100° C. for 4 hours. The solvent was evaporated and the residue crystallised from ethyl acetate to give 1-ethyl-3-[2-(4-[3-(2-benzyloxyphenyl)propyl]benzylamino)ethyl]pyridinium iodide (463 mg); mpt 89° C.

EXAMPLE 71

N-Methyl-N-hydroxy-4-(3-(2-benzyloxyphenyl)propyl)benzamide

A mixture of 4-(3-(2-benzyloxyphenyl)propyl]benzoic acid (1.0 g), 1-HOBT (0.39 g) and DCCI (0.595 g) in DMF (10 ml) was stirred for 3 hours, then added to a solution of N-methylhydroxylamine HCl (0.24 g) and Et$_3$N (0.29 g) in CH$_2$Cl$_2$ (10 ml) and stirred for 70 hours. The product was extracted in 2N aqueous KOH and washed with ethyl acetate. The aqueous solution was acidified with concentrated HCl and extracted with diethyl ether. The solvent was evaporated and the residue subjected to flash chromatography on silica gel (using diethyl ether:methanol (95:5) as eluant) to give N-methyl-N-hydroxy-4-(3-(2-benzyloxyphenyl)propyl)benzamide as a gum (0.39 g).

EXAMPLE 72

N-Hydroxy-4-(3-(2-benzyloxyphenyl)propyl)benzamide

The procedure described in Example 71 was repeated using hydroxylamine hydrochloride to give N-hydroxy-4-(3-(2-benzyloxyphenyl)propyl)benzamide. mpt. 103°–104° C.

EXAMPLE 73

1-[4-(3-(2-Benzyloxyphenyl)propyl)phenyl]-3-[2-chloroethyl]urea

2-Chloroethyl isocyanate (0.35 ml) was added dropwise to a stirred solution of 4-[3-(2-benzyloxyphenyl)propyl] benzamine (1.17 g) in CH$_2$Cl$_2$ (20 ml). After 30 minutes, the reaction mixture was evaporated to give a yellow gum which was subjected to medium pressure chromatography on silica gel, eluting with CH$_2$Cl$_2$:diethyl ether (3:1), to give, after crystallisation from diethyl ether, 1-[4-(3-(2-benzyloxyphenyl)propyl)phenyl]-3-[2-chloroethyl]urea (1.23 g); mpt 120°–121° C.

EXAMPLE 74

The procedure described in example 73 was repeated using the appropriate isocyanate (RNCO) and 'benzeneamine', to give the following compounds:

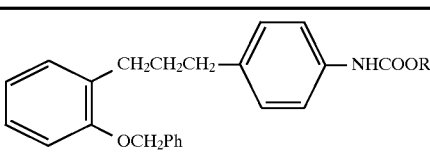

| Compound | R | mpt (°C.) | Footnote |
|---|---|---|---|
| 1 | CH₂CO₂Et | 111–112 | |
| 2 | CH₂CO₂H | 184–185 | a |

Footnote
a: Compound 2 was prepared from compound 1 using method Example 1 (A).

EXAMPLE 75

(A) 4-[3-(2-Benzyloxyphenyl)propyl]benzene isocyanate in dioxane (⅓ of the solution that was prepared as described in (B) below) was added to a stirred solution of 2-aminomethylpyridine (0.2 ml) in dichloromethane (10 ml) for 1 hour, evaporated to dryness and subjected to medium pressure chromatography on silica gel to give, after crystallisation from diethyl ether, 1-[4-(3-(2-benzyloxyphenyl)propyl)phenyl]-3-[2-pyridylmethyl]urea (0.62 g) mpt 126°–127° C.

(B) The solution of 4-[3-(2-benzyloxyphenyl)propyl]benzene isocyanate in dioxane was prepared by heating a mixture of 4-[3-(2-benzyloxyphenyl)propyl]benzoic acid (2.0 g), Et₃N (1.61 ml) and DPPA (1.31 ml) in dioxane (20 ml) for 3 hours.

EXAMPLE 76

The procedure described in example 75 was repeated using the appropriate amines (RNH₂) and 4-[3-(2-benzyloxyphenyl)propyl]benzene isocyanate.

| Compound | R | mpt (°C.) |
|---|---|---|
| 1 | —CH₂-(pyridyl) | 132–133 |
| 2 | —CH₂CH₂CH₃ | 90–91 |

EXAMPLE 77

A similar procedure to that of Example 72 (C) was repeated using the appropriate alcohol and modified by the addition of dioxane to give the following carbamate compounds.

| Compound | R | mpt (°C.) |
|---|---|---|
| 1 | (pyridyl) | 96–97 |
| 2 | —CH₂CH₂OMe | 45–47 |

EXAMPLE 78

N-(4-(3-(5-Amino-2-benzyloxyphenyl)propyl)phenyl)-3-pyridineacetamide

The title compound was prepared from Compound 3, Example 71 using a similar method to that of Example 2, Footnote a, mpt 110°–112° C.

EXAMPLE 79

N-[4-(3-(5-Acetylamino-2-benzyloxyphenyl)propyl)phenyl]-3-(pyridyl)acetamide

The title compound was prepared from Example 78, using a similar method to that of Example 2 Footnote b; mpt 172°–174° C.

EXAMPLE 80

N-(4-(3-(5-(2-Methyl-2-hydroxypropionylamino)-2-benzyloxyphenyl)-propyl)phenyl)-3-pyridineacetamide The title compound was prepared from Example 78, using a similar method to that of Example 56 (A).

EXAMPLE 81

N-(2-(Ethanesulphinyl)ethyl)-4-[3-(2-benzyloxyphenyl)propyl]benzamide

The title compound was prepared from Example 45 compound 90, using a similar method to that of Example 56.

EXAMPLE 82

N-(2-(Ethanesulphonyl)ethyl)-4-[3-(2-benzyloxyphenyl)propyl]benzamide

The title compound was prepared from Example 45 compound 90, using a similar method to that of Example 57.

EXAMPLE 83

N-(Tetrazol-5-ylmethyl)-4-[3-(2-benzyloxyphenyl)propyl]benzamide

The title compound was prepared from Example 45, compound 91 using a similar method to that of Example 92 (A).

EXAMPLE 84

6-[2-(2-Benzyloxyphenyl)-ethyl]-3-tetrazolyl-2(1 H)-pyridinone (A) A mixture of 6-[2-(2-benzyloxyphenyl)ethyl]-3-cyano-2(1 H)pyridinone (165 mg), sodium azide (130 mg)

and ammonium chloride (115 mg) in dry DMF (10 ml) was stirred and heated at 90° C. for 72 hours. The mixture was poured into water (100 ml) and extracted with ethyl acetate (100 ml). The extracts were washed with water (2×100 ml) and brine (1×100 ml), dried (sodium sulphate), filtered and evaporated to dryness. The residue was purified by chromatography on silica gel using dichloromethane: methanol: acetic acid (19:1:0, 95:5:1, 90:10:1) as eluant then triturated with diethyl ether, filtered and dried. There was thus obtained 6-[2-(2-benzyloxyphenyl)-ethyl]-3-tetrazolyl-2(1 H)-pyridinone (106 mg), m.p. >260° C.

The starting material was obtained as follows:

(B) A mixture of 2-benzyloxybenzaldehyde (5 g, Apin) and sodium borohydride (1.4 g) in ethanol (50 ml) was stirred under argon for 1 hour. The solvent was evaporated, the residue dissolved in ethyl acetate and added dropwise to 0.1M hydrochloric acid solution (200 ml) at 0° C. The organic solution was washed with saturated aqueous sodium hydrogen carbonate (100 ml) and brine (100 ml), dried (sodium sulphate), filtered and evaporated to give 2-benzyloxybenzyl alcohol (4.91 g) as an oil.

C) To a solution of 2-benzyloxybenzyl alcohol (4.83 g) in diethyl ether (40 ml) was added dropwise, at 0° C., a solution of phosphorus tribromide (6.27 g) in diethyl ether (10 ml). The mixture was warmed to ambient temperature, diluted with diethyl ether (100 ml) and filtered through a pad of silica gel washing with 1 litre of diethyl ether. The combined organic solution was washed with saturated aqueous sodium hydrogen carbonate (100 ml) and brine (100 ml), dried (sodium sulphate), filtered and evaporated to give 2-benzyloxybenzyl bromide (5.88 g) as an oil.

(D) 3-Cyano-6-methyl-2(1 H)-pyridinone (0.67 g, Aldrich) was added to a THF (50 ml) solution of lithium diisopropylamide (11 mmol, prepared by the standard method) and stirred under argon at −5° C. for 2 hours. 2-Benzyloxybenzyl bromide (1.39 g) in THF (10 ml) was added and the mixture stirred, at 0° C., for 1 hour. The solvent was evaporated, the residue dissolved in water (100 ml) and washed with diethyl ether (2×100 ml) and hexane (100 ml) and filtered. A precipitate was collected. The aqueous filtrate was cooled (ice bath) and acidified (acetic acid) to pH4. The resulting precipitate was filtered and combined with the other solid, triturated with 1:1 dichloromethane:diethyl ether and dried. There was thus obtained 6-[2-(2-benzyloxyphenyl)ethyl]-3-cyano-2(1 H)-pyridinone (0.94 g), m.p. 211°–213° C.

EXAMPLE 85

The process described in example 84 was repeated with the appropriate 6-[2-(2-benzyloxyphenyl)ethyl]-3-cyano-2(1 H)-pyridinone to give the compounds described in the following table with appropriate modifications described in the notes below.

| Compd. No. | R1 | R2 | R3 | m.p. | Footnotes |
|---|---|---|---|---|---|
| 1 | Br | H | H | >260° C. | a |
| 2 | Cl | H | H | 220–222° C. | b,c |
| 3 | NO$_2$ | H | H | >260° C. | d,e |
| 4 | Br | Me | H | 258–259° C. | f |
| 5 | Br | H | Br | >260° C. | g |
| 6 | NO$_2$ | Me | H | >260° C. | e,h |
| 7 | NO$_2$ | Me | Br | 257–259° C. | i |
| 8 | Br | Me | Br | 253–255° C. | j |

Footnotes a: 2-benzyloxy-5-bromobenzaldehyde, used as a starting material for the synthesis of 2-benzyloxy-5-bromobenzyl alcohol, was obtained as follows:
A mixture of 5-bromosalicylaldehyde (12 g), potassium carbonate (16.5 g) and benzyl bromide (7.8 ml) in dry DMF (50 ml) was stirred under argon for 18 hours, diluted with ethyl acetate (200 ml) and filtered. The filtrate was washed with 0.05M HCl (100 ml), saturated aqueous sodium hydrogen carbonate (100 ml) and brine (100 ml), dried (sodium sulphate), filtered and evaporated to give 2-benzyloxy-5-bromobenzaldehyde (15.8 g) m.p. 70–72° C.

b: 2-benzyloxy-5-chlorobenzaldehyde, used as a starting material for the synthesis of 2-benzyloxy-5-chlorobenzyl alcohol, was obtained as described in footnote a above using 5-chlorosalicylaldehyde as the starting material.

c: 6-[2-(2-benzyloxy-5-chlorophenyl)ethyl]-3-cyano-2(1H)-pyridinone was converted to 6-[2-(2-benzyloxy-5-chlorophenyl)ethyl]-3-tetrazolyl-2(1H)-pyridinone using a modification of the method in Example 1 as follows: A mixture o 6-[2-(2-benzyloxy-5-chlorophenyl)ethyl]-3-cyano-2(1H)-pyridinone (365 mg), sodium azide (200 mg) and triethylamine hydrochloride (206 mg) in dry N-methyl-pyrrolidinone (10 ml) was heated under argon at 150° C., for 1 hour, poured into saturated aqueous ammonium chloride (100 ml) and extracted with ethyl acetate (100 ml). The ethyl acetate was evaporated and the residue purified by chromatography on silica gel using dichloromethane:methanol:acetic acid (95:5:1) as eluant. The resulting solid was crystallised from DMF/water and there was thus obtained 6-[2-(2-benzyloxy-5-chloro-phenyl)ethyl]-3-tetrazolyl-2(1H)-pyridinone (180 mg).

d: 2-benzyloxy-5-nitrobenzaldehyde, used as a starting material for the synthesis of 2-benzyloxy-5-nitrobenzyl alcohol, was obtained as described as described in footnote a above using 5-nitrosalicylaldehyde as the starting material.

e: 6-[2-(2-benzyloxy-5-nitrophenyl)ethyl]-3-tetrazolyl-2(1H)-pyridinone was obtained as described in footnote c above.

f: 6-[2-(2-benzyloxy-5-bromophenyl)ethyl]-1-methyl-3-tetrazolyl-2(1H)-pyridinone was obtained from 6-[2-(2-benzyloxy-5-bromo-phenyl)ethyl]-3-tetrazolyl-2(1H)-pyridinone as follows:
A mixture of 6-[2-(2-benzyloxy-5-bromophenyl)ethyl]-3-tetrazolyl-2(1H)-pyridinone (810 mg), sodium hydrogen carbonate (300 mg) and chloromethyl pivalate (0.4 ml) in dry DMF (50 ml) was stirred under argon for 14 days, poured into saturated aqueous ammonium chloride (100 ml) and extracted with ethyl acetate (100 ml). The ethyl acetate solution was washed with water (100 ml), dried (magnesium sulphate), filtered and evaporated. The residue was purified by chromatography on silica gel using dichloromethane:methanol:acetic acid (97:3:1) as eluant. A mixture of the resulting oil (0.94 g), sodium carbonate (180 mg), and iodomethane (0.1 ml) in dry DMF (20 ml) was stirred under argon for 18 hours, poured into saturated aqueous ammonium chloride (100 ml) and extracted with ethyl acetate (100 ml). The ethyl acetate was washed with 0.05M HCl (100 ml), saturated aqueous sodium hydrogen carbonate (100 ml) and brine (100 ml), dried (sodium sulphate), filtered and evaporated to give a yellow foam (560 mg) after purification by chromatography on silica gel using dichloromethane:ethyl acetate (100:, 95:5, 90:10, 80:20) as eluant. To a solution of the foam (560 mg) in methanol (10 ml) was added a -continued solution of sodium hydroxide (0.1 g) in water (1.5 ml) and the mixture stirred for 18 hours. The solvents were evaporated and the residue was triturated with acetic acid (10 ml). The resulting solid was filtered and crystallised from DMF/water to give 6-[2-(2-benzyloxy-5-bromophenyl)ethyl]-1-methyl-3-tetrazolyl-2(1H)-pyridinone.

g: To a solution of compound 1 (0.75 g, see above for preparation) in dry DMF (40 ml) was added bromine (0.1 ml) dropwise. The mixture was stirred for 18 hours, the precipitate filtered off, washed with DMF and dried. There was thus obtained 6-[2-(2-benzyloxy-5-bromophenyl)ethyl]-5-bromo-3-tetrazolyl-2(1H)-pyridinone (447 mg).

h: 2-[2-benzyloxy-5-nitrophenethyl]-5-(5-tetrazolyl)-1-methylpyridine was obtained from 2-[2-benzyloxy-5-nitrophenethyl]-5-(5-tetrazolyl)pyridine by a similar process to that described in footnote f.

i: 6-[2-benzyloxy-5-nitrophenethyl]-5-bromo-1-methyl-3-(5-tetrazolyl)-2(1H)-pyridinone was obtained from 6-[2-benzyloxy-5-nitrophenethyl]-1-methyl-3-(5-tetrayolyl)-2-(1H)-pyridinone by a similar process to that described in footnote g.

j: 6-[2-benzyloxy-5-bromophenethyl]-5-bromo-1-methyl-3-(5-tetrazyolyl)-2(1H)-pyridinone was obtained from 6-[2-benzyloxy-5-bromophenethyl]-1-methyl-3-(5-tetrazolyl)-2-(1H)-pyridinone by a similar process to that described in footnote g.

EXAMPLE 86

6-[2-(2-Benzyloxy-phenyl)ethyl]-3-carboxy-2(1 H)-pyridinone (A) A solution of 6-[2-(2-benzyloxyphenyl)ethyl)-3-tertbutoxy-carbonyl-2(1 H)-pyridinone (400 mg) in 98% formic acid (1 ml) was left to stand for 44 hours, triturated with diethyl ether and the resulting solid filtered and dried. There was thus obtained 6-[2-(2-benzyloxyphenyl)ethyl]-3-carboxy-2(1 H)-pyridinone (266 mg) m.p. 214°–215° C.

6-[2-(2-Benzyloxyphenyl)ethyl]-3-tertbutoxycarbonyl-2(1 H)-pyridinone was obtained as follows:

(B) 3-tertbutoxycarbonyl-6-methyl-2(1 H)-pyridinone (1.49 g, J. Het. Chem., 1981, 18, 1611) was added to a THF (20 ml) solution of lithium diisopropylamide (14.3 mmol, prepared by the standard method) and stirred under argon, at −30° C., for 2.5 hours. 2-Benzyloxybenzyl bromide (2 g, prepared as described in Example 1) in THF (10 ml) was added and the mixture stirred, at −30° C., for 1 hour, then warmed to ambient temperature. The mixture was poured into saturated aqueous ammonium chloride (200 ml) and extracted with dichloromethane. The solvent was evaporated and crystallised from isopropranol. There was thus obtained 6-(2-[2-benzyloxyphenyl)ethyl]-3-tertbutoxycarbonyl-2(1 H)-pyridinone (1.85 g) m.p. 146°–147° C.

EXAMPLE 87

The process described in Example 86 was repeated with the appropriate 6-[2-(2-benzyloxyphenyl)ethyl]-3-tertbutoxycarbonyl-2(1 H)-pyridinones to give the compounds described in the following table with appropriate modifications described in the notes below.

| Compound | R | Ring | mpt | Footnotes |
|---|---|---|---|---|
| 1 | Br | 3-methyl-pyridinone (NH) | 233–235 | a |
| 2 | NO₂ | " | 225–227 | b |
| 3 | Br | N-Me pyridinone | 175–176 | a,c |
| 4 | NO₂ | " | 195–197 | b,d |
| 5 | CN | pyridinone (NH) | 220–222 | e |

Structure: R-substituted phenyl with CH₂CH₂-Ring-COOH and OCH₂Ph a: The preparation of 2-benzyloxy-5-bromobenzaldehyde is described in Example 2, footnote a. It was converted to 2-benzyloxy-5-bromobenzyl bromide by the general method described in Example 84, (B) and (C).

b: The preparation of 2-benzyloxy-5-nitrobenzaldehyde is described in Example 2, footnote d. It was converted to 2-benzyloxy-5-nitrobenzyl bromide by the general method described in Example 84, (B) and (C).

c: 6-[2-(2-benzyloxy-5-bromophenyl)ethyl]-3-tertbutoxycarbonyl-1-methyl-2(1H)-pyridinone was obtained from 6-[2-(2-benzyloxy-5-bromo-phenyl)-ethyl]-3-tertbutoxycarbonyl-2(1H)pyridinone as follows:

A mixture of 6-[2-(2-benzyloxy-5-bromophenyl)ethyl]-3-tertbutoxycarbonyl-2(1H)-pyridinone (2 g, prepared as described for compound 1 (Example 4) above), sodium carbonate (0.44 g) and iodomethane (0.26 ml) in dry DMF was stirred under argon for 18 hours, poured into water (100 ml) and extracted with ethyl acetate (2 × 100 ml). The organic solution was washed with brine (3 × 100 ml), dried (sodium sulphate), filtered and evaporated. The residue was purified by chromatography on silica gel using dichloromethane:methanol (100:0, 99:1) as eluant. The resulting solid was triturated with pentane/diethyl ether and dried. There was thus obtained 6-[2-(2-benzyloxy-5-bromophenyl)-ethyl]-3-tertbutoxycarbonyl-1-methyl-2(1H)-pyridinone (1.61 g) m.p. 147.5–148.5° C.

d: 6-[2-(2-benzyloxy-5-nitrophenyl)ethyl]-3-tertbutoxycarbonyl-1-methyl-2(1H)-pyridinone was obtained from 6-[2-(2-benzyloxy-5-nitrophenyl)ethyl]-3-tertbutoxycarbonyl-2(1H)-pyridinone by the method described in footnote c above.

e: 3-bromomethyl-4-benzyloxybenzonitrile was synthesised as follows:-
(A) 2-Hydroxy-5-formylbenzoic acid (commercially available) was converted to benzyl 2-benzyloxy-5-formylbenzoate by a similar method to that of Example 1, (I) (using two equivalents of K₂CO₃ and benzyl bromide). Benzyl 2-benzyloxy-5-formylbenzoate was converted to benzyl 2-benzyloxy-5-hydroxyiminomethylbenzoate by a similar method to that of Example 3 Footnote q.
(B) To a solution of DMAP (1.86 g) in CH₂Cl₂ (50 ml) at −10° C. was added thionyl chloride (0.98 ml) in CH₂Cl₂ (10 ml). The reaction was stirred for 5 minutes, then a solution of benzyl 2-benzyloxy-5-hydroxyiminomethylbenzoate (4.4 g) in CH₂Cl₂ (40 ml) was added, at −5° C. The reaction was stirred for 10 minutes at −10° C., then a solution of DMAP (1.86 g) in CH₂Cl₂ (20 ml) was added. The reaction was stirred at 20° C. for 10 minutes, poured into water and the organic layer washed with 0.05N aqueous HCl, saturated aqueous NaHCO₃ and brine, dried (MgSO₄), filtered and evaporated to give benzyl 2-benzyloxy-5-cyanobenzoate -continued (4.2 g).

(C) The benzyl ester was converted to the corresponding methyl ester by hydrolysis (method of Example 1 (A)), acid chloride formation and addition of methanol which was carried out using a similar method to that of Example 1 (A), replacing the amine with methanol.

(D) To a solution of methyl 2-benzyloxy-5-cyanobenzoate (17.2 g) in THF (200 ml) was added LiBH$_4$ (3.5 g). The reaction was heated at reflux for 1 hour, the solvent evaporated and the residue extracted with ethyl acetate and washed with 1N aqueous HCl, saturated aqueous NaHCO$_3$ and brine, dried (MgSO$_4$), filtered and evaporated. The residue was filtered through 7734 silica gel, eluting with 2.5% EtOAc/CH$_2$Cl$_2$, to give 2-benzyloxy-5-cyanobenzylalcohol as a white solid (12.1 g); mpt 98–100° C. The "benzyl alcohol" was converted to 3-bromomethyl-4-benzyloxy-benzonitrile by a similar method to that of Example 84 (C).

EXAMPLE 88

2-[2-(2-Benzyloxyphenyl)ethyl]pyrimidin-6(1 H)-one-5-carboxylic acid (A) To a mixture of ethyl 2-[2-(2-benzyloxyphenyl)ethyl]- pyrimidin-6(1 H)-one-5-carboxylate (3.3 g) in ethanol (100 ml) was added 2M sodium hydroxide (10 ml). The mixture was stirred for 18 hours, the solvents evaporated and the residue acidified with 1M HCl and the precipitate filtered off. There was thus obtained 2-[2-(2-benzyloxyphenyl) ethyl]pyrimidin-6(1 H)-one-5-carboxylic acid (2.38 g) mp. 192°–194° C.

Ethyl 2-[2-(2-benzyloxyphenol)ethyl]pyrimidin-6(1 H)-one-5-carboxylate was obtained as follows:

(B) 2-(2-Hydroxyphenyl)propionic acid was benzylated with two equivalents of benzyl bromide using the process described in Example 85, footnote a to give benzyl 2-(2-benzyloxyphenyl)propionate.

(C) Benzyl 2-(2-benzyloxyphenyl)propionate was converted to 2-(2-benzyloxyphenyl)propionic acid using a similar method to that described above for the hydrolysis of ethyl 2-[2-(2-benzyloxyphenyl)-ethyl]pyrimidin -6(1 H)-one-5-carboxylate.

(D) To a mixture of 2-(2-benzyloxyphenyl)propionic acid (42.81 g) in dichloromethane at 0° C. was added oxalyl chloride (17.37 ml) and 1 drop of DMF. The mixture was stirred for 2 hours at ambient temperature, evaporated to dryness and the residue dissolved in THF (50 ml). This solution was added to aqueous ammonia (200 ml) in THF (50 ml) at 0° C. and the mixture stirred at ambient temperature for 18 hours. The mixture was concentrated and the resulting precipitate filtered and dried. There was thus obtained 2-(2-benzyl-oxyphenyl)propionamide (33.74 g).

(E) To a mixture of 2-(2-benzyloxyphenyl)propionamide (33.74 g) in THF (50 ml) was added pyridine (32.03 ml). The mixture was cooled at 0° C. and trifluoroacetic anhydride was added. The mixture was stirred at ambient temperature for 18 hours. The solvents were evaporated and the residue dissolved in ethyl acetate (200 ml), and washed with water (100 ml) sodium bicarbonate (100 ml) and brine (100 ml). The organic solution was dried (magnesium sulphate), filtered and evaporated. The residue was dissolved in dichloromethane (200 ml) and filtered through a pad of silica gel and evaporated. There was thus obtained 2-(2-benzyloxyphenyl)propionitrile (28 g).

(F) To a mixture of ammonium chloride (4.49 g) in toluene (25.5 ml) at 5° C. was added trimethylaluminium (2M solution in toluene, 42 ml. The mixture was stirred for 2 hours. 2-(2-benzyloxyphenyl)-propionitrile (10 g) in toluene (50 ml) was added and the mixture heated at 80° C. for 18 hours. The cooled mixture was poured into a slurry of silica gel in chloroform, stirred for 5 minutes and filtered. The silica gel was washed with methanol and the combined organic solutions evaporated to give 2-(2-benzyloxyphenyl) propionamidine (16 g).

(G) Sodium (0.9 g) was added to ethanol (100 ml), the solution cooled to 0° C. and 2-(2-benzyloxyphenyl) propionamidine (10 g) and diethyl ethoxymethylene malonate (8.75 ml) added and the mixture heated under reflux for 3 hours. The solvent was evaporated and the residue acidified to pH4 with 1M HCl. The mixture was mixed with ethyl acetate (100 ml) and the precipitate filtered off to give ethyl 2-[2-(2-benzyloxyphenyl)ethyl]pyrimidin-6(1 H)-one-5-carboxylate (3.3 g).

EXAMPLE 89

The process described in example 88 was repeated with the modifications described in the footnotes to give the following compounds:

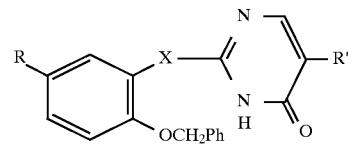

| Compound | R | X | R | R$^1$ | mpt | Footnote |
|---|---|---|---|---|---|---|
| 1 | Br | CH$_2$CH$_2$ | H | CO$_2$H | 192–194 | a |
| 2 | Br | CH$_2$CH$_2$ | Et | CO$_2$H | 135–136 | a,b |
| 3 | H | —(CH$_2$)$_3$— | H | CO$_2$H | 158–160 | c |
| 4 | H | —(CH$_2$)$_2$— | H | CH$_2$CO$_2$H | 190–191 | d | a: Methyl 2-(2-benzyloxy-5-bromophenyl)propionate was prepared as follows:
To a solution of 2-(2-hydroxyphenyl)propionic acid (50 g) in methanol at 0–5° C. was added dropwise thionyl chloride (22.4 ml). The mixture was warmed to ambient temperature, stirred for 18 hours, evaporated and the residue dissolved in ethyl acetate (200 ml) washed with sodium bicarbonate (2 x 100 ml) and brine (100 ml), dried (magnesium sulphate) and evaporated to give methyl 2-(2-hydroxyphenyl)propionate (54 g).
A mixture of methyl 2-(2-hydroxyphenyl)propionate (27.15 g) and tetrabutylammonium tribromide (80 g) in chloroform (100 ml) was stirred for 4 hours, the solution washed with sodium thiosulphate (2 x 100 ml) and water (2 x 200 ml). The organic solution was dried (magnesium sulphate) and evaporated. The resulting oil was purified by chromatography on silica gel using ethyl acetate: hexane (3:7) as eluant to give emthyl 2-(2-hydroxy-5-bromophenyl)propionate (22.9 g).
b:- A similar method to that of Example 88 (F) was used with ethylammonium chloride in the place of ammonium chloride.
c:- 4-(2-Benzyloxyphenyl)butanenitrile was prepared as follows:-
(A) Methyl 3-(2-benzyloxyphenyl)propionate was converted to 3-(2-benzyloxyphenyl)-1-propanol by a similar method to that of Example 87, Footnote e (D), using diethyl ether in place of THF as solvent.
(B) To a solution of 3-(2-benzyloxyphenyl)-1-propanol (25 g) in CCl$_4$ (100 ml) and CHCl$_3$ (100 ml) was added triphenylphosphine (50 g). The reaction was heated at reflux for 1 hour and filtered through silica gel to give an oil (48 g). The oil was dissolved in DMSO (150 ml) and sodium cyanide (10 g) added. The mixture was heated at 120° C. for 2 hours, cooled to 20° C., poured onto aqueous ferrous sulphate solution and extracted with diethyl ether. The organic layer was washed (water), dried (MgSO$_4$) filtered through silica gel and evaporated to give 4-(2-benzyloxyphenyl) butanenitrile (22.8 g) as an oil.
d:- Diethyl hydroxymethylene succinate was used in place of diethyl ethoxymethylene malonate.

EXAMPLE 90

N1-Methyl-2-[2-(2-Benzyloxyphenyl)-ethyl] pyrimidin-6(1 H)-one-5-carboxylic acid (A) To a mixture of methyl N1-methyl-2-[2-(2-benzyloxyphenyl)-ethyl]pyrimidin-6(1 H)-one-5- carboxylate (0.41 g) in pyridine (10 ml) was added LiI (0.3 g). The mixture was heated at 100° C. for 3 hours, LiI (0.3 g) was added and the mixture heated for a further 3 hours, and poured into 2M HCl. The resulting precipitate was filtered and dried. There was thus obtained N1-methyl-2-[2-(2-benzyloxyphenyl)-ethyl]pyrimidin-6(1 H)-one-5-carboxylic acid (190 mg) mp. 143°–144° C.

Methyl N1-methyl-2-[2-(2-benzyloxyphenyl)ethyl]pyrimidin-6(1 H)-one-5-carboxylate was obtained as follows:

(B) N-Methyl-2-(2-benzyloxyphenyl)propionamidine was prepared by the method described in Example 88 for the synthesis of 2-(2-benzyloxy-phenyl) propionamidine using methylamine hydrochloride instead of ammonium hydrochloride.

(C) Ethyl N1-methyl-2-(2-benzyloxyphenyl)ethyl]pyrimidin-6(1 H)-one-5-carboxylate was prepared from N-methyl-2-(2-benzyloxyphenyl)-propionamidine by a similar method to that described in Example 88 for the synthesis of ethyl 2-[2-(2-benzyloxyphenyl)ethyl]pyrimidin-6(1 H)-one-5-carboxylate using dimethyl methoxymethylene malonate instead of diethyl ethoxymethylene malonate.

(D) A mixture of ethyl N1-methyl-2-[2-(2-benzyloxyphenyl)-ethyl]pyrimidin-6(1 H)-one-5-carboxylate (0.5 g) and para-toluene sulphonic acid (30 mg) in methanol was heated under reflux for 18 hours, 150 mg of para-toluene sulphonic acid was added and the mixture heated under reflux for a further 24 hours. The solvent was evaporated to give methyl N1-methyl-2-[2-(2-benzyloxyphenyl)ethyl]-pyrimidin-6(1 H)-one-5-carboxylate (410 mg).

EXAMPLE 91

2-[(E)-2-(2-Benzyloxy-5-bromophenyl)ethenyl]-4(1 H)-oxo-5-pyridinecarboxylic acid (A) The title compound was prepared from ethyl 2-[(E)-2-(2-benzyloxy-5-bromophenyl)ethenyl]-4(1 H)-oxo-5-pyridinecarboxylate by a similar method to that of Example 1, (A) and purified by crystallisation from DMF/water mixtures; mpt 272°–272.5° C.

The ester was prepared as follows:

(B) A mixture of 2-benzyloxy-5-bromobenzaldehyde (18.49 g), malonic acid (13.22 g), piperidine (1.26 ml) and pyridine (200 ml) was heated at 100° C. for 3 hours, poured onto ice cold 2M aqueous HCl and the resulting solid isolated by filtration. The solid was dissolved in ethyl acetate, washed with 2M aqueous HCl (3 times) and brine, dried (MgSO$_4$), filtered and evaporated to give (E)-3-(2-benzyloxy-5-bromophenyl)prop-2-enoic acid as a white crystalline solid (19 g).

(C) (E)-3-(2-Benzyloxy-5-bromophenyl)prop-2-enoic was converted to (E)-3-(2-benzyloxy-5-bromophenyl) acryloyl chloride by the first part of the method of Example 44. The acid chloride (5.27 g) and ethyl 2-dimethylaminomethylene)-3-oxobutanoate (2.31 g) were added in THF to a 1M THF solution of LiN(SiMe$_3$)$_2$ (30.26 ml), at −70° C., dropwise over 2 minutes. The reaction was stirred at ambient temperature for 3 mintues, then acetic acid (25.1 ml) and ammonium acetate (1.25 g) added and the solvent evaporated. The residue was heated at 80° C. for 90 minutes, extracted with CH$_2$C$_2$, washed with water, dried (MgSO$_4$), filtered and evaporated. The residue was purified by flash chromatography on silica gel, eluting with CH$_2$Cl$_2$:hexane (9:1) to give ethyl 2-[(E)-2-(2-benzyloxy-5-bromophenyl)ethenyl]-4(1 H)-oxo-5-pyridinecarboxylate (1.55 g).

EXAMPLE 92

The compounds listed in the table were prepared by a similar method to that of Example 1 (A), from the appropriate ester derivatives.

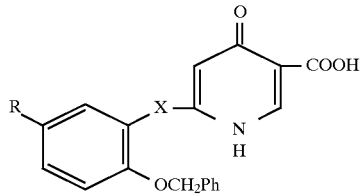

| Compound | R | Link | mpt | Footnote |
|---|---|---|---|---|
| 1 | Br | CH$_2$CH$_2$ | 217.5–219 | a |
| 2 | NO$_2$ | (E)CH═CH | 202.5–203 | b |
| 3 | NO$_2$ | —(CH$_2$)$_2$— | 240–240.5 | c |
| 4 | H | —(CH$_2$)$_2$— | 233.5–234 | d |

Footnotes a:- The ester, ethyl 2-[2-benzyloxy-5-bromophenethyl]-4(1H)-oxo-5-pyridinecarboxylate, was prepared from ethyl 2-[(E)-2-(2-benzyloxy-5-bromophenyl)ethenyl]-4(1H)-oxo-5-pyridine-carboxylate by a similar method to that of Example 7 (E).
b:- The ester, ethyl 2-[(E)-2-(2-benzyloxy-5-nitrophenyl)ethenyl]-4(1H)-oxo-5-pyridine carboxylate, was prepared from 2-benzyloxy-5-nitrobenzaldehyde using similar processes to those described in example Example 91.
c:- The ester, ethyl 2-[2-benzyloxy-5-nitrophenethyl]-4-(1H)-oxo-5-pyridine carboxylate, was prepared from ethyl 2-[(E)-2-(2-benzyloxy-5-nitrophenyl) ethenyl]-4(1H)-oxo-5-pyridine carboxylate by a similar method to that of Example 7 (E).
d:- The ester, ethyl 2-[2-benzyloxyphenethyl]-4-(1H)-oxo-5-pyridine carboxylate, was prepared from ethyl 2-[(E)-2-(2-benzyloxyphenyl)ethenyl]-4(1H)-oxo-5-pyridinecarboxylate by a similar method to that of Example 1 (E). The "olefin" was prepared from 3-(2-benzyloxyphenyl) propenoic acid by a similar method to that of Example 91(C).

EXAMPLE 93

2-[2-Benzyloxyphenethyl]-4-methoxy-5-pyridinecarboxylic acid (A) The title compound was prepared from methyl 2-[2-benzyloxyphenethyl)-4-methoxy-5-pyridinecarboxylate by a similar method to that of Example (A) and purified by crystallisation from ethyl acetate/hexane mixtures; mpt 181.5°–182° C.

The methyl ester was prepared as follows:

(B) Triphenylphosphine (0.27 g) and methanol (0.04 ml) were added to ethyl 2-[2-benzyloxyphenethyl]-4-(1 H)-oxo-5-pyridinecarboxylate (0.35 g) in toluene. After 5 minutes, diethyl azodicarboxylate (0.24 g) was added and the reaction mixture stirred for 18 hours. The mixture was diluted with ethyl acetate and washed with water and brine, dried (MgSO$_4$), filtered and evaporated. The residue was purified by MPLC on silica gel, eluting with ethyl acetate:hexane (2:8), to give methyl 2-[2-benzyloxyphenethyl)-4-methoxy-5-pyridinecarboxylate as a white solid (0.25 g).

EXAMPLE 94

3-[6-(2-Benzyloxy-5-cyanophenethyl)-2-(1 H)-oxo-3-pyridyl]ureidoacetic acid

The title compound was prepared from methyl 3-[6-(2-benzyloxy-5-cyanophenethyl)-2-(1 H)-oxo-3-pyridyl]ureidoacetate by a similar method to that of Example 1 (A).

The ester was prepared from 6-[2-benzyloxy-5-cyanophenethyl]-2(1 H)-oxo-3-pyridinecarboxylic acid and glycine methyl ester by a similar method to that of example 56 (A).

EXAMPLE 95

(A) A mixture of 6-[2-(2-benzyloxy-5-bromophenyl)ethyl]-3carboxy-2(1 H)pyridinone (1.0 g) and 1,1'-carbonyldiimidazole (0.76 g) in dry THF (40 ml) was heated at 50° C. for 3 hours under argon. The solvent was evaporated and the residue mixed with ethanolamine (0.6 ml) and dichloromethane (50 ml) and stirred for 18 hours. The mixture was purified by subjecting to chromatography on silica gel using dichloromethane:methanol (95:5) as eluant. The resulting residue was crystallised from isopropanol. There was thus obtained 6-[2-(2-benzyloxy-5-bromophenyl)ethyl]-3-(2-hydroxyethylcarbamoyl)-2(1 H)pyridinone (0.77 g), m.p. 164°–166° C.

6-[2-(2-Benzyloxy-5-bromophenyl)ethyl]-3-carboxy-2(1 H)-pyridinone was prepared as follows:

(B) A mixture of 5-bromosalicylaldehyde (12 g), potassium carbonate (16.5 g) and benzyl bromide (7.8 ml) in DMF (50 ml) was stirred for 18 hours, poured into ethyl acetate (100 ml), washed with 0.05M HCl (100 ml), sodium bicarbonate (100 ml) and brine (100 ml), dried (sodium sulphate), filtered and evaporated. The residue was triturated with hexane/diethyl ether to give 2-benzyloxy-5-bromobenzaldehyde (15.8 g) mp.70°–72° C.

(C) A mixture of 2-benzyloxy-5-bromobenzaldehyde (14.55 g) and sodium borohydride (2.6 g) in ethanol (250 ml) was stirred under argon for 1 hour. The solvent was evaporated, the residue dissolved in ethyl acetate and added dropwise to 0.1M hydrochloric acid solution (200 ml) at 0° C. The organic solution was washed with saturated aqueous sodium hydrogen carbonate (100 ml) and brine (100 ml), dried (sodium sulphate), filtered and evaporated to give 2-benzyloxy-5-bromobenzyl alcohol (14.85 g) as an oil. To a solution of 2-benzyloxy-5-bromobenzyl alcohol (14.75 g) in diethyl ether (150 ml) was added dropwise, at 0° C., to a solution of phosphorus tribromide (13.68 g) in diethyl ether (40 ml). The mixture was warmed to ambient temperature, diluted with diethyl ether (200 ml) and filtered through a pad of silica gel (200 g) washing with 1 litre of diethyl ether. The combined organic solution was washed with saturated aqueous sodium hydrogen carbonate (150 ml) and brine (150 ml), dried (sodium sulphate), filtered and evaporated to give 2-benzyloxy-5-bromobenzyl bromide (15.2 g).

(D) 3-Tertbutoxycarbonyl-6-methyl-2(1 H)-pyridinone (2.94 g) [J. Het. Chem., 1981, 18, 1611] was added to a THF (50 ml) solution of lithium diisopropylamide (32 mmol) [prepared by the standard method] and stirred under argon at −30° C. for 2.5 hours. 5-Bromo-2-benzyloxybenzylbromide (5 g) in THF (40 ml) was added and the mixture stirred at −30° C. for 1 hour then warmed to ambient temperature. The mixture was poured into saturated aqueous ammonium chloride (200 ml) and extracted with ethyl acetate (2×100 ml). The combined organic solutions were washed with brine (100 ml), dried (sodium sulphate) and evaporated. The residue was triturated with dichloromethane. There was thus obtained 6-[2-(2-benzyloxy-5-bromophenyl)ethyl)-3-tertbutoxycarbonyl-2(1 H)-pyridinone (5 g) mp. 190°–192° C.

(E) A solution of 6-[2-(2-benzyloxy-5-bromophenyl)ethyl]-3-tertbutoxycarbonyl-2(1 H)-pyridinone (3.23 g) in 98% formic acid (6 ml) was left to stand for 18 hours, triturated with diethyl ether and the resulting solid filtered and dried. There was thus obtained 6-[2-(2-benzyloxy-5-bromophenyl)ethyl]-3-carboxy-2(1 H)-pyridinone (2.68 g) m.p. 233°–235° C.

EXAMPLE 96

A similar method to that described in Example 95 (A) was used to prepare the compounds listed in the table from the appropriate carboxylic acid and amine derivatives.

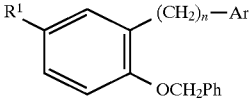

| Compound | R¹ | n | Ar | R² | mpt | Footnote |
|---|---|---|---|---|---|---|
| 1 | Br | 2 | 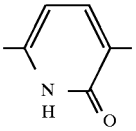 | —CH₂CH₂CH₃ | 123–125 | |
| 2 | Br | 2 | " | 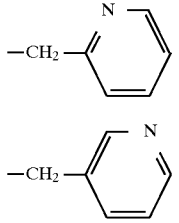 | 153–155 | |
| 3 | Br | 2 | " | 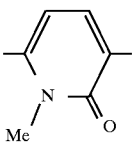 | 165–166 | |
| 4 | NO₂ | 2 | " | —CH₂CH₂OH | 199–201 | a |
| 5 | Br | 2 | (see structure) | " | 187–188 | b |

-continued structure: R¹-substituted phenyl with -(CH₂)ₙ-Ar-CONHR² and -OCH₂Ph

| Compound | R¹ | n | Ar | R² | mpt | Footnote |
|---|---|---|---|---|---|---|
| 6 | NO₂ | 2 | " | " | 228–229 | a, c |
| 7 | H | 2 | 3,6-dimethyl-2-pyridone | —CH₂CH₂CH₃ | 155–156 | d |
| 8 | H | 2 | " | —CH₂-(2-pyridyl) | 147–148 | d |
| 9 | H | 2 | " | —CH₂CH₂OH | 170–171 | d |
| 10 | NO₂ | 2 | " | —CH₂CH₂CH₃ | 151–153 | a |
| 11 | NO₂ | 2 | " | —CH₂-(2-pyridyl) | 155–160 | a |
| 12 | H | 3 | 2-hydroxy-5-methylphenyl | —CH₂-(2-pyridyl) | 93–94 | |
| 13 | Br | 2 | 3,6-dimethyl-2-pyridone | —(CH₂)₄OH | 164–165 | |
| 14 | Br | 2 | " | 2-hydroxycyclohexyl | 157–158 | |
| 15 | Br | 2 | " | 2-hydroxyphenyl | 194.5–195.5 | |
| 16 | Br | 2 | " | 4-hydroxyphenyl | 250–251.5 | |
| 17 | Br | 2 | " | trans-4-hydroxycyclohexyl | 203–203.5 | |
| 18 | Br | 2 | " | 3-hydroxyphenyl | 265–267.5 | |
| 19 | Br | 2 | " | —CH₂CH(OH)CH₃ | 163.5–164 | |

-continued

Structure: R¹-substituted phenyl with OCH₂Ph, (CH₂)ₙ—Ar—CONHR²

| Compound | R¹ | n | Ar | R² | mpt | Footnote |
|---|---|---|---|---|---|---|
| 20 | Br | 2 | 3-methyl-6-methyl-2-pyridinone | —(CH₂)₃OH | 121.5–122.5 | |
| 21 | Br | 2 | " | —CH₂CH(OH)CH₂OH | 162.5–163.5 | |
| 22 | H | 2 | 2,5-dimethyl-3-bromo-phenyl | H | 116–117 | |
| 23 | H | 3 | " | H | 114–114.5 | |
| 24 | H | 2 | 2,5-dimethyl-3-methoxy-phenyl | H | 137.5–138 | |
| 25 | H | 3 | " | H | 124.5–125.5 | |
| 26 | Cl | 2 | " | H | 125.5–128.5 | |
| 27 | Br | (E)CH=CH | 2,5-dimethyl-4-pyridinone | —CH₂CH₂OH | 254–255 | |
| 28 | Br | (E)CH=CH | " | —CH₂-(3-pyridyl) | 243.5–244 | |
| 29 | Br | (E)CH=CH | " | —CH₂CH₂CH₃ | 217.5–218 | |
| 30 | Br | (CH₂)₂ | " | —CH₂CH₂OH | 207.5–208 | |
| 31 | Br | (CH₂)₂ | " | —CH₂CH₂CH₃ | 172–172.5 | |
| 32 | Br | (CH₂)₂ | " | —CH₂-(3-pyridyl) | 195.5–196 | |
| 33 | Br | (CH₂)₂ | " | H | 222.5–223.5 | |
| 34 | H | (E)CH=CH | " | —CH₂CH₂OH | 216–218 | |
| 35 | H | (E)CH=CH | " | —CH₂CH₂CH₃ | 199.5–200.5 | |
| 36 | H | (E)CH=CH | " | —CH₂-(3-pyridyl) | 187.5–188.5 | |
| 37 | H | (CH₂)₂ | " | " | 149.5–150.5 | |
| 38 | H | (CH₂)₂ | " | —CH₂CH₂CH₃ | 132–132.5 | |
| 39 | CN | (CH₂)₂ | 3-methyl-6-methyl-2-pyridinone | " | 157–159 | |
| 40 | CN | (CH₂)₂ | " | —CH₂CH₂OH | 198–200 | |

-continued

R¹—[benzene ring with (CH₂)ₙ—Ar—CONHR² and OCH₂Ph substituents]

| Compound | R¹ | n | Ar | R² | mpt | Footnote |
|---|---|---|---|---|---|---|
| 41 | CN | (CH₂)₂ | " | —CH₂—[3-pyridyl] | 198–199 | |
| 42 | CN | (CH₂)₂ | " | —CH₂—[2-pyridyl] | 196–198 | |
| 43 | Br | (CH₂)₂ | " | [1,2,4-triazole-CH₂ group, N=N / N—NH] | >250 | | a: -5-Nitro-2-benzyloxybenzaldehyde was prepared from 5-nitro-2-hydroxybenzaldehyde by the method described in Example 1 for the synthesis of 2-benzyloxy-5-bromobenzaldehyde.
b: -1-Methyl-6-[2-(2-benzyloxy-5-bromophenyl)ethyl]-3-tertbutoxycarbonyl-2(1H)-pyridinone was synthesised from 6-[2-(2-benzyloxy-5-bromophenyl)ethyl]-3-tertbutoxycarbonyl-2(1H)-pyridinone as follows:
A mixture of 6-[2-(2-benzyloxy-5-bromophenyl)ethyl]-3-tertbutoxycarbonyl-2(1H)-pyridinone (2 g), sodium carbonate (0.44 g) and methyl iodide (0.26 ml) in DMF (40 ml) was stirred for 18 hours, poured into water (100 ml) and extracted with ethyl acetate (2 × 100 ml). The combined organic solutions were washed with brine (100 ml), dried (sodium sulphate), filtered and evaporated. The residue was purified by subjecting to chromatography on silica gel using dichloromethane: methanol (0:100 to 1.5:98.5 gradient) as eluant. There was thus obtained 1-methyl-6-[2-(2-benzyloxy-5-bromophenyl)-ethyl]-3-tertbutoxycarbonyl-2 (1H)-pyridinone (1.61 g) mp. 147.5–148.5° C.
c: -1-Methyl-6-[2-(2-benzyloxy-5-nitrophenyl)ethyl]-3-tertbutoxy-carbonyl-2(1H)-pyridinone was obtained from 6-[2-(2-benzyloxy-5-nitrophenyl)ethyl]- 3-tertbutoxycarbonyl-2(1H)-pyridinone using a similar method to that described in note b for the conversion of 6-[2-(2-benzyloxy-5-bromo-phenyl)ethyl]-3-tertbutoxycarbonyl-2(1H)-pyridinone to 1-methyl-6-[2-(2-benzyloxy-5-bromophenyl)ethyl]-3-tertbutoxycarbonyl-2(1H)-pyridinone.
d: -2-Benzyloxybenzaldehyde was obtained commercially from Apin.

EXAMPLE 97

2-[2-(2-Benyloxyphenyl)ethyl]-5-[(3-pyridyl)methylcarbamoyl]pyrimidin-6(1 H)-one (A) Using the method described in Example 95 for the conversion of 6-[2-(2-benzyloxyphenyl-5-bromo)ethyl]-3-carboxy-2(1 H)-pyridinone to 6-[2-(2-benzyloxyphenyl-5-bromo)ethyl]-3-(2-hydroxyethylcarbamoyl)-2(1 H)pyridinone, 2-[2-(2-benzyloxyphenyl)ethyl]pyrimidin-6(1 H)-one-5-carboxylic acid was converted to 2-[2-(2-benzyloxyphenyl)ethyl]-5-[(3-pyridyl)methylcarbamoyl]pyrimidin-6(1 H)-one m.p. 174°–176° C.

2-[2-(2-Benzyloxyphenyl)ethyl]pyrimidin-6(1 H)-one-5-carboxylic acid was obtained as descrbied in Example 89.

EXAMPLE 98

The process described in Example 97 was repeated with the appropriate substituted 2-[2-(2-benzyloxyphenyl)ethyl] pyrimidin-6(1 H)-one-5-carboxylic acid or N1-methyl-2-[2-(2-benzyloxyphenyl)ethyl]pyrimidin-6(1 H)-one-5-carboxylic acid and the appropriate amine to give the compounds described in the following table.

[Structure: R¹—phenyl with OCH₂Ph and (CH₂)₂ linker to pyrimidin-6(1H)-one bearing CONHR³, with R² on N]

| Compd. No | R1 | R2 | R3 | m.p. | Footnote |
|---|---|---|---|---|---|
| 1 | H | H | H | 198–199 | |
| 2 | H | H | n-propyl | 132–135 | |
| 3 | Br | H | 2-Hydroxyethyl | 205–207 | a |
| 4 | Br | H | 2-Pyridylmethy1 | 178–179 | a |
| 5 | Br | H | n-Propyl | 173–175 | a |
| 6 | Br | H | 2-Cyanoethyl | 189–200 | a |
| 7 | H | Me | 2-Pyridylmethyl | 102–104 | b |
| 8 | H | Me | n-Propyl | 95–96 | b |
| 9 | H | H | 2-Pyridylmethyl | 174–176 | | a: -Methyl 2-(2-benzyloxy-5-bromophenyl)propionate (used in the place of benzyl 2-(2-benzyloxyphenyl)propionate) was synthesised as follows:
To a solution of 2-(2-hydroxyphenyl)propionic acid (50 g) in methanol at 0–5° C. was added dropwise thionyl chloride (22.4 ml).
The mixture was warmed to ambient temperature, stirred for 18 hours, evaporated and the residue dissolved in ethyl acetate (200 ml) washed with sodium bicarbonate (2 × 100 ml) and brine (100 ml), dried (magnesium sulphate) and evaporated to give methyl 2-(2-hydroxyphenyl)propionate (54 g).

-continued

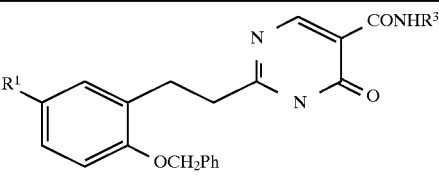

| Compd. No | R1 | R2 | R3 | m.p. | Footnote |
|---|---|---|---|---|---| a A mixture of methyl 2-(2-hydroxyphenyl)propionate (27.15 g) and tetrabutylammonium tribromide (80 g) in chloroform (100 ml) was stirred for 4 hours, the solution washed with sodium thiosulphate (2 × 100 ml) and water (2 × 200 ml). The organic solution was dried (magnesium sulphate) and evaporated. The resulting oil was purified by chromatography on silica gel using ethyl acetate:hexane (3:7) as eluant to give methyl 2-(2-hydroxy-5-bromophenyl)propionate (22.9 g).
b: -1-Methyl-2-[2-(2-benzyloxyphenyl)ethyl]pyrimidin-6(1H)-one-5-carboxylic acid was prepared as described in Example 88.

EXAMPLE 99

6-[2-Benzyloxy-5-bromophenethyl]-2-chloro-3-(N-(5-tetrazolyl)carbamoyl)pyridine

The title compound was prepared as follows:

A mixture of 6-[2-benzyloxy-5-bromophenethyl]-2-(1 H)-oxo-3-pyridinecarboxylic acid (1.1 g), thionyl chloride (10 ml) and DMF (0.1 ml) was heated at reflux for 1 hour, the thionyl chloride evaporated (as an azeotrope with toluene) and the residue dissolved in $CH_2Cl_2$. To this solution was added a mixture of triethylamine (3.25 ml) and 5-aminotetrazole (0.4 g) in $CH_2Cl_2$ at 5° C. The reaction mixture was stirred for 1 hour at 20° C., and washed with water twice. A white precipitate formed and was isolated by filtration and dried. There was thus obtained the title compound (0.57 g), mpt. 218°–220° C.

EXAMPLE 100

The process described in example 99, was repeated with 6-[2-benzyloxy -5-bromophenethyl]-2-(1 H)-oxo-3-pyridinecarboxylic aicd and the appropriate amine to give the compounds listed below. In each case the product was purified by chromtagraphy on silica gel.

| Compound | R | mpt |
|---|---|---|
| 1 | —CH₂CH₂OH | 106–108 |
| 2 | —CH₂CH₂CH₃ | 129–131 |
| 3 | —CH₂-(pyridyl) | 122–124 |
| 4 | —CH₂-(pyridyl) | 106–108 |

EXAMPLE 101

6-[2-Benzyloxy-5-bromophenethyl]-2-methoxy-3-pyridinecarboxylic acid

Methyl 6-(2-benzyloxy-5-bromophenethyl]-2-methoxy-3-pyridinecarboxylate was converted to the title compound (mpt 141°–143° C.) by a similar method to that of example 1 (A) which was modified by heating the reaction mixture at reflux for 3 hours and using MeOH as the solvent.

The methyl ester was produced as follows:

6-(2-benzyloxy-5-bromophenethyl]-2-(1 H)-oxo-3-pyridinecarboxylic acid was converted to methyl 6-[2-benzyloxy-5-bromophenethyl]-2-methoxy-3-pyridinecarboxylate by a similar method to that of Example 99 using methanol in the place of 5-aminotetrazole.

A mixture of methyl 6-[2-benzyloxy-5-bromophenethyl]-2-chloro-3-pyridinecarboxylate (7.0 g) and sodium methoxide (2.5 mole equivalents) in methanol was heated at 140° C. for 5 hours in a Carius Tube. The solvent was evaporated and the residue extracted with ethyl acetate and washed with saturated aqueous $NH_4Cl$, water and brine. The organic solution was dried ($Na_2SO_4$), filtered and evaporated. The residue was purified by chromatography on 7734 silica gel, eluting with 1% MeOH/$CH_2Cl_2$, to give methyl 6-[2-benzyloxy-5-bromophenethyl]-2-methoxy-3-pyridinecarboxylate (6.16 g).

EXAMPLE 102

6-[2-Benzyloxy-5-bromophenethyl]-2-chloro-3-pyridine carboxamide

A solution of methyl 6-[2-benzyloxy-5-bromophenethyl]-2-chloro-3-pyridinecarboxylate (2.0 g) in ethanol (60 ml) saturated with ammonia was heated at 177° C. under pressure for 6 hours. The solvent was evaporated and the residue subjected to chromatography on silica gel (7734). Two products were isolated. The first was eluted with 2.5% ethyl acetate/$CH_2Cl_2$ and the second with 5% MeOH/$CH_2Cl_2$. The first product was identified as a mixture of the methyl and ethyl esters of 6-[2-benzyloxy-5-bromophenethyl]-2-amino-3-pyridinecarboxylic aicd (0.3 g). The second produce was identified as the title compound (0.6 g) mpt. 142°–144° C.

EXAMPLE 103

4-[3-(2-(3-Pyridylmethyloxy)phenyl)propyl]benzoic acid

Methyl 4-[3-(2-(3-pyridylmethyloxy)phenyl)propyl] benzoate (1.03 g, 2.85 ml) was disolved in 1:1 MeOH/THF (20 ml total). The solution was treated with NaOH solution (2M, 3.4 ml, 6.8 mmol) and the reaction was allowed to stirred at ambient temperature for 18 hours. The pH was adjusted to pH7 with 1N HCl and the reaction was partially evaporated and partitioned between EtOAc/water. The aqueous layer was extracted with 1-propanol/$CH_2Cl_2$ (1:4). The organic extracts were combined and the residue was dried by evaporating off toluene at reduced pressure. EA $C_{22}$ $H_{21}$ $NO_3$. 0.33$H_2O$:calc 74.8% C 6.14% H 4.0% N found 74.8% C 6.0% H 3.7% N MS FAB(–ve):346 [M–H]–.

The following compounds were prepared using a similar method to that described above from the appropriate ester.

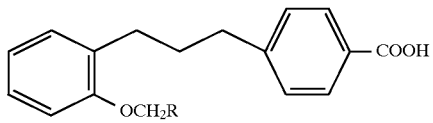

| R | MS | Footnotes |
|---|---|---|
| 2-thienyl | FAB(-ve):351[M - H]- | a,b |
| 4-pyridyl | FAB(-ve):346[M - H]- | c,d |
| 2-furanyl | FAB(+ve):337[M + H]+ | e,f |

Footnotes
a: -Elemental analysis: Calc for $C_{21}H_{20}SO_3$ 71.6% C, 5.72% H, found 71.2% C, 5.6% H.
b: -pH adjusted to pH5.
c: -Elemental analysis: Calc for $C_{22}H_{21}NO_3 \cdot 0.1H_2O$ 75.7% C, 6.12% H, 4.01% N; found 75.6% C, 6.2% H, 3.8% N.
d: -pH adjusted to pH6; product recrystallised from methanol/water.
e: -Elemental analysis: Calc for $C_{21}H_{20}O_4 \cdot 0.25H_2O$ 74.0% C, 5.94% H; found 74.0%, 6.1% H.
f: -pH adjusted to pH5; product m.p. 68–73° C.

The starting materials were prepared as follows:

Methyl 4-[3-(2-hydroxyphenyl)propyl]benzoate (1.35 g, 5 mmol) was dissolved in 0.2 ml of THF. The solution was treated with 3-hydroxymethylpyridine (0.6 g, 5.5 mmol) and triphenylphosphine (1.44 g, 5.5 mmol). To this mixture was added slowly diethylazodicarboxylate (0.96 g, 5.5 mmol). The reaction mixture was stired for 72 hours and the solvent was evaporated. The amide residue was purified by chromatography (methanol, dichloromethane) to give methyl 4-[3-(2-(3-pyridylmethyloxy)phenyl)propyl]benzoate as a pink oil (1.03 g, 57%) MS (CI+):362 [M+H]+.

The following compounds were prepared using a similar method to that described above from methyl 4-[3-(2-hydroxyphenyl) propyl]benzoate and the appropriate alcohol.

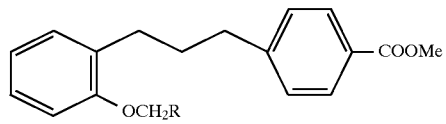

| R | MS | Footnotes |
|---|---|---|
| 1-thienyl | CI+:366[M]+ | a |
| 4-pyridyl | CI+:362[M + H]+ | b |
| 2-furanyl | CI+:350[M]+ | c |

Footnotes
a:- A total of 22 equivalents of DEAD was used. Reaction time 96 hours. Residue was purified by chromatography eluting with diethyl ether/hexane.
b:- Residue was purified by chromatography eluting with methanol/dichloromethane.
c:- Residue was purified by chromatography eluting with diethyl ether/hexane.

EXAMPLE 104

4-[3-(4-(Benzyloxy)pyrimid-5-yl)propyl]benzoic acid tert-Butyl 4-[3-(4-(benzyloxy)pyrimid-5-yl)propyl] benzoate (0.36 g, 0.92 mmol) was dissolved in dichloromethane (0.7 ml) and treated with trifluoro-acetic acid (1.05 g, 9.2 mmol). The reaction was stirred at amibent temperature for 2 hours. The mixture was partitioned between EtOAc/water and the aqueous layer extracted with EtOAc. The organic layers were combined, dried (MgSO$_4$) and evaporated and the solid was triturated with hexane and recrystallised from isopropanol/water. The cream coloured solid was taken up in THF, filtered through Celite and evaporated to give the title product.

EA:$C_{20}H_{18}N_2O_3 \cdot 1/8$ THF
Calc 71.7% C 5.5% H 8.16% N
Found 71.6% C 5.6% H 7.9% N
MS (CI+):335 [M+H]+

The starting material was prepared as follows:

5-Iodo-4-(3 H)-pyrimidinone (1.11 g, 5 mmol) and tert-butyl 4-ethynyl benzoate (1.11 g, 5.5 mmol) were dissolved in DMF (sieve dried, 2.8 ml) and treated with CuI (0.015 g, 0.0 mmol) and triethylamine (1.515 g, 15 mmol). The solution was de-gassed by bubbling argon through for 5 minutes. Palladium catayst (0.019 g, 0.027 mmol) was added and the reaction mixture placed in a oil bath preheated to 55° C. After 40 minutes the reaction mixture was removed from the heat and partitioned between ethyl acetate and water. The aqueous layer was acidified and extracted with ethyl acetate. The organic layers were combined, dried over MgSO$_4$ and evaporated to give a crude product which was purified by chromatography (MeOH, CH$_2$Cl$_2$) to give tert-butyl 4-[2-(pyrimidin-4(3 H)-one-5-yl)ethynyl] benzoate (0.602 g, 41%).
MS (17/4):CI+:297 (M+H)+

Tert-butyl 4-[2-(pyrimidin-4(3 H)-one-5-yl)ethynyl] benzoate (0.59 g, 2.0 mmol) was dissolved in EtOAc (20 ml) and treated with palladium-on-carbon (0.30 g, 10%]. The reaction was placed under a hydrogen atmosphere and stirred overnight at ambient temperature. The reaction was filtered and evaporated to give tert-butyl 4-[2-(pyrimidin-4(3 H)-on-5-yl)ethyl]benzoate which was used without further purification (0.6 g, quantitative).
MS: CI+:301 [M+H]+ tert-Butyl 4-[2-(pyrimidin-4(3 H)-on-5-yl)ethyl]benzoate (0.6 g,) was dissolved in N,N-dimethylaniline (5 ml) and treated with phosphorous-oxy-chloride (1.53 g 10 mmol). The reaction was heated to 100° C. for 2.5 hours and then evaporated at reduced pressure. The residue was diluted with EtOAc, washed (1N HCl 2x, H$_2$O, saturated brine), dried over MgSO$_4$ and evaporated to give tert-butyl 4-[2-(4-chloropyrimidin-5-yl)ethyl]benzoate as a brown oil (0.5 g, 64%) which was used without further purification.
MS CI:319 (M+H)-

Anhydrous benzyl alcohol (0.18 g, 1.74 mmol) was dissolved in THF (3 ml). Potassium tert-butoxide was added (0.213 g, 1.9 mmol) and the mixture was stirred for 5 minutes. tert-Butyl 4-[2-(4-chloropyrimidin-5-yl)ethyl] benzoate (0.49 g, 1.5 mmol) was added as a solution in THF (4 ml). The reaction was stirred at ambient temperature overnight and then partitioned between EtOAc/Water. The aqueous layer was extracted with EtOAc and the organic layers were combined, dried (MgSO$_4$) and evaporated to give an orange-yellow oil. Chromatography eluting wiht EtOAc hexane gave tert-butyl 4-[3-(4-(benzyloxy)pyrimid-5-yl)propyl]benzoic acid as a yellow oil (0.41 g, 70%).
MS CI+:391 [M+H]+

EXAMPLE 105

4-[2-(2-Benzyloxypyrid-3-yl)ethyl]benzoic acid

Methyl 4-[2-(2-benzyloxypyrid-3-yl)ethyl]benzoate was dissolved in EtOH (5 ml) and treated with NaOH (1N, 1.04 ml). The reaction was stirred at ambient temperature for 48 hours, 1N HCL (1.04 ml) was added and the precipitate was filtered and recystllised from iso-propanol to give 4-[2-(2-benzyloxypyrid-3-yl)ethyl]benzoic acid as a white solid (0.054 g, 38%).
MS (CI)+:334 [M+H]+

The starting material was prepared as follows:

Sodium hydride (60%, 2.89 g, 72.3 mmol) was washed with hexane (1x) and suspended in THF (50 ml). Anhydrous benzyl alcohol (8.57 g, 79.3 mmol) was added dropwise and the reaction mixture was stirred for 30 minutes. A solution of 2-chloronicotinonitrile (10.0 g, 72.2 mmol) in THF (50 ml) was added via a syringe (exotherm). The reaction was stirred at ambient temperature for 18 hours then water was added to quench the reaction. The reaction mixture was partitioned between EtOAc/water and the organic phase dried (MgSO$_4$) and evaporated. The residue was purified by chromatography (SiO$_2$, CH$_2$Cl$_2$) to give 2-benzyloxy-3-cyanopyridine as a pale yellow oil which crystallised on standing (11.4 g, 75%).

MS (CI+):211 [M+H]+

2-Benzyloxy-3-cyanopyridine (7.6 g, 36.2 mmol) was dissolved in dichloromethane (100 ml) and a solution of DIBAL (1M in CH$_2$Cl$_2$, 47 ml) was added dropwise over 40 minutes. The temperature of the reaction rose to 30° C. The reaction was stirred at ambient temperature (shielded from light) overnight. The reaction was quenched by pouring into a solution of silica on CH$_2$Cl$_2$. The solvent was evaporated and the silica was applied to the top of a column and eluted with CH$_2$Cl$_2$. Evaporation of the solvent from the appropriate fractions gave 2-benzyloxy-3-pyridinecarbaldehyde (7.3 g, 95%).

MS (CI+):214 [M+H]+

(4-Methoxycarbonylbenzyl)triphenylphosphonium bromide (16.6 g, 33.8 mmol) was suspended in THF (70 ml) under Argon. Lithium bis(trimethylsilyl)amide (1M in THF, 40.5 ml) was added. The reaction mixture was stirred for 1 hour at ambient temperature; the colour changed to orange. 2-Benzyloxy-3-pyridinecarbaldehyde (7.2 g, 33.8 mmol) was added as a solution in THF (50 ml) and the reaction mixture was stirred at amibent temperature overnight (shielded from light). The reaction mixture was partitioned between EtOAc/water, the organic phase was dried (MgSO$_4$) and evaporated. Purification by chromatography (SiO$_2$, eluting with CH$_2$Cl$_2$/hexane) gave methyl 4-[2-(2-benzyloxy-3-pyridyl)ethenyl]benzoate (9.2 g, 79%).

MS (CI+):346 [M+H]+.

A suspension of rhodium on alumina (5%, 0.1 g) in ethanol (20 ml) was flushed well with argon. A solution of the methyl 4-[2-(2-benzyloxypyrid-3-yl)ethenyl]benzoate (1.0 g, 2.9 mmol) in ethanol (60 ml) was added. The reaction was transferred to a manometer under an atmosphere of hydrogen and the reaction was stirred at ambient temperature until 1.4 equivalents hydrogen had been taken up. The reaction mixture was filtered and evaporated and the residue subjected to chromatography on SiO$_2$ (CH$_2$Cl$_2$/hexane) to give 4-[2-(2-benzyloxypyrid-3-yl)ethyl]benzoic acid (0.5 g, 49%).

MS (CI+):378 [M+H]+

EXAMPLE 106

4-[2-(3-Benzyloxy-2-pyridyl)ethyl]benzoic acid

A solution of methyl 4-[2-(3-benzyloxy-2-pyridyl)ethyl] benzoate (0.1 g, 0.3 mmol) in EtOH (1 ml) was treated with aqueous NaOH solution (0.6 ml 1N). The reaction was stirred at ambient temperature for 18 hours and then treated with HCl soltuion (0.6 ml, 1N). The resulting precipitate was filtered and recrystallised from isopropanol to give the title product.

MS (CI+):334 [M+H]+
EA:C$_{21}$ H$_{19}$ NO$_3$.0.25 iPrOH
Calc 75.0% C, 6.03% H, 4.02% N
Found 74.8% C, 5.7% H, 4.2% N
The starting material was prepared as follows:

To a suspension of 3-hydroxy-2-hydroxymethylpyridine hydrochloride (7.0 g, 12.4 mmol) in ethanol (37.5 ml) was added a solution of KOH pellets (85% 1.6 g, 24.7 mmol) in ethanol (25 ml). The reaction was stirred for 5 minutes at ambient temperature and then benzyl bromide was added (2.11 g, 12.36 mmol). The reaction mixture was stirred at ambient temperature for 48 hours, filtered and evaporated. The residue was purified by chromatography (EtOAc, CH$_2$Cl$_2$) to give 3-benzyloxy-2-hydroxymethylpyridine as a colourless solid (1.55 g, 58%) [J. Med. Chem., 15, (1972) 615] m.p. 78.7°–79.2° C.

MS (CI+):216 [M+H]+

A solution of 3-benzyloxy-2-hydroxymethylpyridine (0.25 g, 1.16 mmol) in chloroform (15 ml) was treated with manganese dioxide (0.45 g, 6.34 mmol). The reaction mixture was heated to reflux and held at reflux for 18 hours. The reaction mixture was then filtered through Celite and evaporated to give a yellow gum. This gum was purified by chromatography (EtOAc/CH$_2$Cl$_2$) to give 3-benzyloxy-2-pyridinecarbaldehyde as a colourless gum (0.15 g, 62%).

MS (CI+):214 [M+H]+

(4-Methoxycarbonylbenzyl)triphenylphosphonium bromide (4.42 g, 9.00 mmol) was suspended in THF (50 ml) under argon. Lithium bis-(trimethylsilyl)amide (1M in THF, 10.8 ml) was added and the deep orange reaction was stirred at ambient temperature for 1 hour. A solution of 3-benzyloxy-2-pyridinecarbaldehyde (2.0 g, 9.4 mmol) in THF (20 ml) was added and the reaction was stirred at ambient temperature for 2 hours 30 minutes. The reaction was partitioned between EtOAc/water, the aqueous phase was extracted with EtOAc, the organic layers were combined, dried (MgSO$_4$) and evaporated. The residue was purified by chromatography (EtOAc/CH$_2$Cl$_2$) to give methyl 4-[2-(3-benzyloxy-2-pyridyl)ethenyl]benzoate as a yellow oil. (3.01 g) .

MS (CI)+:346 [M+H]+

Methyl 4-[2-(3-benzyloxy-2-pyridyl)ethenyl]benzoate (2.0 g, 5.8 nnol) was partially dissolved in EtOAc (20 ml) and EtOH (10 ml). The reaction vessel was flushed with argon, palladium-on-carbon (0.2 g, 10%) was added and the reaction was flushed with argon followed by hydrogen. The reaction was stirred at ambient temperature for 18 hours, filtered and evaporated to give methyl 4-[2-(3-hydroxy-2-pyridyl)ethyl]benzoate as a pale orange solid (1.3 g, 90%) which was used without further purification.

MS (CI)+:258 [M+H]+

A solution of methyl 4-[2-(3-hydroxy-2-pyridyl)ethyl] benzoate (1.1 g, 4.3 mmol) in DMF (30 ml) was treated with benzyl bromide (0.89 g, 5.2 mmol) and potassium carbonate (0.72 g, 5.2 mmol). The reaction was stirred at ambient temperature overnight and then, partitioned between EtOAc/water. The organic phase was washed well with water, dried (MgSO$_4$) and evaporated. The residue was purified by chromatography (SiO$_2$) eluting with CH$_2$Cl$_2$/EtOAc to give methyl 4-[2-(3-benzyloxy-2-pyridyl)ethyl]benzoate (0.94 g, 53%) as a low melting yellow solid.

MS (CI+):348 [M+H]+

EXAMPLE 107

N-(2-Hydroxyethyl)-4-[2-(3-benzyloxy-2-pyridyl) ethyl]benzamide

Methyl 4-[2-(3-benzyloxy-2-pyridyl)ethyl]benzoate (0.20 g, 0.576 mmol) was dissolved in ethanolamine (3 ml) and heated to 160° C. under argon for 2 hours. Water was added (3 ml) and the aqueous layers were extracted with ethyl acetate and the organic phase was dried (MgSO$_4$) and evaporated. The residue was recrystallised from EtOAc/hexane and washed with ether to give the title product (0.064 g, 29%).

MS (CI+):377 [M+H]+
EA:C$_{22}$ H$_{24}$ N$_2$O$_3$.1/3 H$_2$O
Calc 72.25% C 6.45% H 7.33% N
Found 72.1% C 6.4% H 7.3% N

EXAMPLE 108

N-(2-Hydroxyethyl)-4-[2-(2-benzyloxy-3-pyridyl) ethyl]benzamide

The title compound was prepared using a similar method to that of Example 107 from the corresponding methyl ester.
MS CI+:377 [M+H]+
EA:C$_{22}$ H$_{24}$ N$_2$O$_3$ 1/7 H$_2$O
Calc 72.9% C, 6.41% H, 7.39% N
Found 72.9% C, 6.3% H, 7.3% N

EXAMPLE 109

N-(2-Pyridylmethyl)-4-[2-(2-benzyloxy-3-pyridyl) ethyl]benzamide

4-[2-(2-benzyloxy-3-pyridyl)ethyl]benzoic acid (0.48 g, 1.44 mmol) and 2-aminomethylpyridine (0.189 g, 1.748 mmol) were dissolved in DMF (20 ml) and cooled to 0° C. Triethylamine (0.15 g, 1.5 mmol) was added followed by diphenylphosphorylazide (0.41 g, 1.48 mmol). The reaction mixture was stirred under argon and allowed to warm to ambient temperature overnight. The reaction was partitioned between EtOAc/water, the organic phase was washed with aqueous sodium bicarbonate, water, dried (MgSO$_4$) and evaporated. The residue was purified by flash chromatography (MeOH/CH$_2$Cl$_2$) followed by recrystallisation from EtOAc/hexane and then from EtOH/water to give the title product.
MS (EI+):423 [M+]

EXAMPLE 110

N-(3-Pyridyl(methyl)-4-[2-benzyloxy-3-pyridyl) ethyl]benzamide

The title product was prepared using a similar method to that of Example 109 from the appropriate amine.
MS (EI+):423 [M+]

EXAMPLE 111

4-[3-(2-Benzyloxy-3-pyridyl)prop-2-enyl]benzoic acid (2-(4-Carboxyphenyl)ethyl)triphenylphosphonium bromide (10.9 g, 22.2 mmol) was suspended in THF (80 ml) and the flask was flushed with argon. Lithium bis(trimethylsilyl) amide (1M in THF, 48.8 ml) was added dropwise and the reaction stirred for 1 hour, becoming dark brown. A solution of 2-benzyloxy-3-pyridinecarbaldehyde (4.73 g, 22.2 mmol) in THF (20 ml) was added slowly. The reaction was stirred at ambient temperature for 18 hours (shielding from light alumimium foil). The reaction mixture was then partitioned between Et$_2$O/water, the organic layer was washed with water and the aqueous layers were combined, acidified with HCl and extracted with EtOAc. The organic phase was dried (MgSO$_4$) and evaporated and purified by colum chromtagraphy with MeOH/CH$_2$Cl$_2$to give the title product.
MS:346 [M+H] (279 [M+H] for Ph$_3$PO)

EXAMPLE 112

4-[3-(2-Benzyloxy-3-pyridyl)propyl]benzoic acid

Rhodium-on-alumina (0.69 mg, 5% Ph) was suspended in ethanol (5 ml). The reaction flask was flushed well with argon. 4-[3-(2-Benzyloxy-3-pryidyl)prop-2-enyl]benzoic acid (0.64 g) was dissolved in ethanol (25 ml) and added to the calalyst. The reaction was placed under an atmosphere of hydrogen (manometer) and hydrogenation continued until the reaction had taken up 1.45 equivalents of hydrogen (11 ml). The reaction mixture was then filtered and evaporated. The material obtained was purified by chromatography (EtOAc/CH$_2$Cl$_2$) and recrystallised from ethanol/water to give the title product (0.028 g, 4%).
MS (CI+):348 [M+H]+
EA:C$_{22}$ H$_{21}$ NO$_3$
Calc 76.1% C, 6.09% H, 4.03% N
Found 75.9% C, 6.1% H, 3.9% N

EXAMPLE 113

4-[3-(3-Benzyloxy-2-pyridyl)prop-2-enyl]benzoic acid (2-(4-Carboxyphenyl)ethyl)triphenylphosphonium bromide (0.58 g, 1.17 mmol) was suspended in THF (7 ml) and lithium bis(trimethylsilyl)amide was added (1M in THF, 2.46 ml). The reaction mixture turned orange and was allowed to stir for 1 hour at ambient temperature. A solution of 3-benzyloxy-2-pyridinecarbaldehyde (0.25 g, 1.17 mmol) in THF (3.5 ml) was added slowly. The reaction was stirred at ambient temperature for 1 hour. The reaction was quenched by the addition of water (8 ml) and ether (8 ml). The layers were separated, the ether layer was washed with water and the as aqueous layers were combined, acidified with 1N HCl and extracted with EtOAc (2×). The organic extracts were dried (MgSO$_4$) and evaporated to give the title product as a mixture of isomers (2.7 g 66%).
MS (CI+):346 [M+H]+

EXAMPLE 114

4-[3-(3-Benzyloxy-2-pyridyl)propyl)benzoic acid

Methyl 4-[3-(3-benzyloxy-2-pyridyl)propyl)benzoate (0.3 g, 0.83 mmol) was dissolved in EtOH (3 ml) and treated with 1N NaOH (1.66 ml). The reaction was stirred at ambient temperature for 18 hours. A solution of hydrochloric acid (1N, 1.66 ml) was added and the resulting precipitate was filted and recrystallised from ethanol to give the title product as a white solid (0.054 g).
MS (EI+):348 [M+H]+
The starting material was prepared as follows:
4-[3-(3-Benzyloxy-2-pyridyl)prop-2-enyl)benzoic acid (0.1 g, 0.29 mmol) was dissolved in methanol (5 ml) and cooled to 0° C. To the solution was added thionyl chloride (0.086 g, 0.73 mmol). The reaction was allowed to warm to ambient temperature and stirred at ambient temperature for 18 hours. The reaction mixture was then evaporated, the residue partitioned between ethyl acetate and water and the organic phase dried (MgSO$_4$) and evaporated. The residue was purified by chromatography (SiO$_2$ EtOAc/CH$_2$Cl$_2$) to give methyl 4-[3-(3-benzyloxy-2-pyridyl)prop-2-enyl] benzoate as an oil (0.05 g, 49%).
MS (CI)+:360 [M+H]+
Methyl 4-[3-(3-benzyloxy-2-pyridyl)prop-2-enyl] benzoate (1.5 g, 4.2 mmol) was dissolved in ethanol (5 ml) and EtOAc (15 ml), treated with 10% palladium on carbon (0.15 g) and placed under a hydrogen atmosphere. The mixture was stirred at ambient temperature for 10 hours and filtered and evaporated to give methyl 4-[3-(3-hydroxy-2-pyridyl)propyl]benzoate as a yellow oil (0.88 g, 77%).
MS (CI+):272 [M+H]+
Methyl 4-[3-(3-hydroxy-2-pyridyl)propyl]benzoate (0.87 g, 3.2 mmol) was dissolved in DMF (5 ml) and treated with benzyl bromide (0.66 g, 3.9 mmol) and potassium carbonate (0.53 g, 3.8 mmol). The reaction was stirred at ambient temperature potassium overnight and then partitioned between EtOAc/water. The organic phase was washed well with water, dried (MgSO$_4$) and evaporated. The residue was purified (SiO$_2$, CH$_2$Cl$_2$/EtOAc) to give methyl 4-[3-(3-benzyloxy-2-pyridyl)propyl]benzoate as a pale yellow oil. MS (CI+):362 [M+H]+

We claim:

1. A compound of the formula (I):

wherein:

A is selected from the group consisting of optionally substituted: phenyl, naphthyl, pyridyl, pyrimidyl, pyrazinyl, pyridazinyl, oxazolyl, thienyl, thiadiazolyl and thiazolyl;

wherein the —Z— and —OCH(R$^3$)— groups are positioned in a 1,2 relationship to one another on ring carbon atoms;

and provided that the ring atom in the 2-position relative to the ring carbon atom bearing the —OCH(R$^3$)— group and in the 3-position relative to the ring carbon atom bearing the —Z—B—R$^1$ group is unsubstituted and, when A is naphthyl, either the —Z—B—R$^1$ group is in the 1-position and the —OCH(R$^3$)— group is in the 2-position of the naphthyl group and the ring atom in the 3-position is not substituted, or the —Z—B—R$^1$— group is in the 2-position and the —OCH(R$^3$)— group is in the 3-position of the naphthyl group and the ring atom in the 4-position is not substituted (according to the IUPAC system);

B is selected from the group consisting of optionally substituted: phenyl, pyridyl, thiazolyl, thienyl, thiadiazolyl, imidazolyl, oxazolyl, pyrazinyl, pyridazinyl, pyrimidinyl, pyridone, pyridazinone, furan, pyrrole and pyrimidinone; wherein the A—Z— and —R$^1$ groups are positioned in either a 1,3 or a 1,4 relationship to one another on ring carbon atoms in B in 6 membered rings and in a 1,3 relationship to one another on ring carbon atoms in B in 5-membered rings;

D is selected from the group consisting of optionally substituted: phenyl, thienyl, furyl, pyridyl, thiazolyl and oxazolyl;

R$^1$ is carboxy, optionally substituted tetrazolyl, carboxyC$_{1-4}$alkyl, optionally substituted tetrazolylC$_{1-4}$alkyl, hydroxamic acid, sulphonic acid or tetronic acid, or R$^1$ is of the formula —CONR$^6$R$^7$ wherein R$^6$ is hydrogen, C$_{1-6}$alkyl, C$_{3-7}$cycloalkyl, C$_{3-7}$cycloalkylC$_{1-3}$alkyl, C$_{5-7}$cycloalkenyl or C$_{5-7}$cycloalkenylC$_{1-3}$alkyl and R$^7$ is hydrogen, C$_{1-6}$alkoxycarbonyl, hydroxy or optionally substituted: C$_{1-10}$alkyl, C$_{1-10}$alkenyl, C$_{1-10}$alkynyl, C$_{3-7}$cycloalkyl, C$_{3-7}$cycloalkylC$_{1-6}$alkyl, C$_{3-7}$cycloalkylC$_{2-6}$alkenyl, C$_{3-7}$cycloalkylC$_{2-6}$alkynyl, C$_{5-7}$cycloalkenyl, C$_{3-7}$cycloalkenylC$_{1-6}$alkyl, C$_{5-7}$cycloalkenylC$_{2-6}$alkenyl, C$_{5-7}$cycloalkenylC$_{2-6}$alkynyl, 5- or 6-membered heteroaryl, 5- or 6-membered heteroarylC$_{1-6}$alkyl, 5- or 6-membered saturated or partially saturated heterocyclyl, 5- or 6-membered saturated or partially saturated heterocyclylC$_{1-6}$alkyl, 5- or 6-membered heteroarylium or 5- or 6-membered heteroaryliumC$_{1-6}$alkyl; or wherein R$^6$ and R$^7$ together with the amide nitrogen to which they are attached (NR$^6$R$^7$) form an amino acid residue or ester thereof, or R$^1$ is of the formula —NR$^6$COR$^8$ wherein R$^6$ is as hereinabove defined and R$^8$ is of the formula OR$^9$ wherein R$^9$ is hydrogen, optionally substituted C$_{1-6}$alkyl, 5- or 6-membered monocyclic heteroaryl or a 5- or 6-membered monocyclic saturated or partially saturated heterocyclyl, or R$^8$ is of formula NR$^{10}$R$^{11}$ wherein R$^{10}$ is hydrogen or C$_{1-6}$alkyl and R$^{11}$ is optionally substituted C$_{1-6}$alkyl or R$^8$ is optionally substituted C$_{1-6}$alkyl, or R$^1$ is of the formula —CONR$^6$SO$_2$R$^{12}$ wherein R$^6$ is as hereinabove defined and R$^{12}$ is optionally substituted: C$_{1-10}$alkyl, C$_{2-10}$alkenyl, C$_{2-10}$alkynyl, C$_{3-7}$cycloalkyl, C$_{3-7}$cycloalkylC$_{1-6}$alkyl, C$_{3-7}$cycloalkylC$_{2-6}$alkenyl, C$_{3-7}$cycloalkylC$_{2-6}$alkynyl, C$_{5-7}$cycloalkenyl, C$_{3-7}$cycloalkenylC$_{1-6}$alkyl, C$_{5-7}$cycloalkenylC$_{2-6}$alkenyl, C$_{5-7}$cycloalkenylC$_{2-6}$alkynyl, 5- or 6-membered heteroaryl, 5- or 6-membered heteroylarylC$_{1-6}$alkyl, phenyl, phenylC$_{1-6}$alkyl, 5- or 6-membered saturated or partially saturated heterocyclyl, 5- or 6-membered saturated or partially saturated heterocyclylC$_{1-6}$alkyl, 8–10 membered heteroarylC$_{1-6}$alkyl or 5- or 6-membered heteroarylC$_{1-4}$alkyl, or R$^1$ is of the formula —CONR$^6$N(R$^{16}$)R$^{17}$ wherein R$^6$ is as hereinabove defined, R$^{16}$ is hydrogen or C$_{1-6}$alkyl and R$^{17}$ is hydrogen, hydroxy or optionally substituted: C$_{1-10}$alkyl, C$_{2-10}$alkenyl, C$_{2-10}$alkynyl, C$_{3-7}$cycloalkyl, C$_{3-7}$cycloalkylC$_{1-6}$alkyl, C$_{3-7}$cycloalkylC$_{2-6}$alkenyl, C$_{3-7}$cycloalkylC$_{2-6}$alkynyl, C$_{5-7}$cycloalkenyl, C$_{5-7}$cycloalkenylC$_{1-6}$alkyl, C$_{5-7}$cycloalkenylC$_{2-6}$alkenyl, C$_{5-7}$cycloalkenylC$_{2-6}$alkynyl, 5- or 6-membered heteroaryl, 5- or 6-membered heteroarylC$_{1-6}$alkyl, 5- or 6-membered saturated or partially saturated heterocyclyl, 5- or 6-membered saturated or partially saturated heterocyclylC$_{1-6}$alkyl, or R$^{16}$ and R$^{17}$, together with the nitrogen atom to which they are attached, form a 4 to 8-membered saturated or partially saturated heterocyclic ring or form an amino acid residue or ester thereof, and wherein any 5- or 6-membered heteroaryl group in R$^1$ is a monocyclic ring system having 5 or 6 ring atoms wherein 1, 2 or 3 ring atoms are selected from the group consisting of nitrogen, oxygen and sulphur, any 5- or 6-membered saturated or partially saturated heterocyclyl group in R$^1$ is a ring system having 5 or 6 ring atoms wherein 1, 2 or 3 of the ring atoms are selected from the group consisting of nitrogen, oxygen and sulphur, any 5- or 6-membered heteroarylium group in R$^1$ is selected from the group consisting of pyridinium, pyrimidinium, pyrazinium, pyridazinium and imidazolium, any 8–10 membered heteroaryl group in R$^1$ is a bicyclic ring system having 8 to 10 ring atoms wherein 1, 2, 3 or 4 ring atoms are selected from the group consisting of nitrogen, oxygen and sulphur, and any 4 to 8-membered saturated or partially saturated heterocyclic ring in R$^1$ is a ring system having 4 to 8 ring atoms wherein 1, 2 or 3 of the ring atoms are selected from the group consisting of nitrogen, oxygen and sulphur;

R$^3$ is selected from the group consisting of hydrogen and C$_{1-4}$alkyl;

Z is selected from the group of formulae consisting of —(CH(R$^5$))$_m$—, —(CHR$^5$)$_p$CR$^5$=CR$^5$(CHR$^5$)$_q$—, —(CHR$^5$)$_r$C(=O)CR$^5$=CR$^5$(CHR$^5$)$_s$— and —(CHR$^5$)$_t$C(=O)(CHR$^5$)$_u$—, wherein m is 2, 3 or 4, p and q are independently 0, 1 or 2 providing p+q is not greater than 2, one of r and s is 0 and the other is 1 and t and u are independently 0, 1, 2 or 3 providing t+u is not less than 1 or greater than 3, and R$^5$ is selected from the group consisting of hydrogen, methyl, ethyl, hydroxy, methoxy and ethoxy;

or N-oxides thereof;

or S-oxides thereof;

or a pharmaceutically acceptable salt or an in vivo hydrolysable ester or amide thereof;

provided that when ring B is optionally substituted phenyl and R$^1$ is an amide of formula —CONR$^6$R$^7$ wherein R is hydrogen or C$_{1-6}$alkyl and R$^7$ is hydrogen, then ring B bears no more than one optional substituent.

2. A compound of the formula (I) according to claim 1 wherein A is optionally substituted: phenyl, thienyl, naphthyl or thiadiazolyl.

3. A compound of the formula (I) according to claim 1 wherein B is optionally substituted: pyridyl, phenyl, thiazolyl, thienyl, pyrazinyl, oxazolyl, pyridazinyl or 2-pyridone.

4. A compound of the formula (I) according to claim 1 wherein D is optionally substituted: phenyl, thienyl or furyl.

5. A compound according to claim 1 of the formula (III):

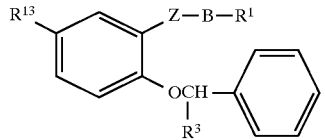

(III)

wherein

R$^1$,R$^3$, and Z are as defined in claim 1, R$^{13}$ is hydrogen, halo, trifluoromethyl, nitro, hydroxy, amino, C$_{1-4}$alkylamino, di[C$_{1-6}$alkyl]amino, cyano, C$_{1-6}$alkoxy, carboxy, allyloxy, S(O)$_p$C$_{1-6}$alkyl (p is 0, 1 or 2), S(O)$_p$-phenyl (p is 0, 1 or 2), C$_{1-6}$alkyl (optionally substituted by hydroxy, C$_{1-4}$alkoxy, amino, halo, nitro, S(O)$_p$C$_{1-4}$alkyl (p is 0, 1 or 2), S(O)$_p$-phenyl (p is 0, 1 or 2) or cyano), carbamoyl, C$_{1-4}$alkylcarbamoyl, di(C$_{1-4}$alkyl)carbamoyl, C$_{2-6}$alkenyl, C$_{2-6}$alkynyl, C$_{3-7}$cycloalkyl, C$_{3-7}$cycloalkylC$_{1-3}$alkyl, C$_{3-7}$cycloalkylC$_{2-3}$alkenyl, C$_{5-7}$cycloalkenyl, C$_{5-7}$cycloalkenylC$_{2-3}$alkenyl, benzyl, benzoyl, benzyloxy, C$_{1-4}$alkoxycarbonylamino, C$_{1-4}$alkanoylamino, (wherein the alkanoyl group is optionally substituted by hydroxy), C$_{1-4}$alkanoyl(N—C$_{1-4}$alkyl)amino, wherein the alkanoyl group is optionally substituted by hydroxy), C$_{1-4}$alkanesulphonamido, benzenesulphonamido, aminosulphonyl, C$_{1-4}$alkylaminosulphonyl, di(C$_{1-4}$alkyl)aminosulphonyl, C$_{1-4}$alkoxycarbonyl, C$_{2-4}$alkanoyloxy, C$_{1-6}$alkanoyl, formylC$_{1-4}$alkyl, trifluoroC$_{1-3}$alkylsulphonyl, 1-(hydroxyimino)-1-(phenyl)methyl, 1-(C$_{1-4}$alkoxyimino)-1-(phenyl)methyl, hydroxyiminoC$_{1-6}$alkyl, C$_{1-4}$alkoxyiminoC$_{1-6}$alkyl, C$_{1-6}$alkylcarbamoylamino, carboxyC$_{1-4}$alkoxy, C$_{2-6}$alkenyl (substituted by halo), N-(amino)iminoC$_{1-4}$alkyl, N-(C$_{1-4}$alkylamino)iminoC$_{1-4}$alkyl, N-[di(C$_{1-4}$alkyl)amino]iminoC$_{1-4}$alkyl, N-(phenyl)aminoiminoC$_{1-4}$alkyl, 5-membered heteroaryl containing 1 or 2 heteroatoms selected from nitrogen, oxygen and sulphur, tetramethylene, and diradicals of the formula —(CH$_2$)$_3$CO—, —(CH$_2$)$_3$C(=N—OH)— and —(CH$_2$)$_3$C(=N—OC$_{1-4}$alkyl)— and B is phenyl or hydroxypyridyl.

6. A compound of the formula (III) according to claim 5 wherein R$^3$ is hydrogen.

7. A compound of the formula (III) according to claim 5 wherein Z is —(CH$_2$)$_2$—, —(CH$_2$)$_3$— or —CH=CH—.

8. A compound of the formula (III) according to claim 5 wherein R$^1$ is carboxy, tetrazolyl, methanesulphonylaminocarbonyl, benzenesulphonylaminocarbonyl, (optionally substituted on the phenyl ring by nitro, hydroxy, halo, amino, C$_{1-4}$alkyl, C$_{1-4}$alkoxy, cyano or trifluoromethyl), or R$^1$ is of the formula —CONR$^6$R$^7$ wherein R$^6$ is hydrogen or methyl and R$^7$ is propyl, 2-pyridylmethyl, 3-pyridylmethyl, 2-hydroxyethyl, tetrazolyl, tetrazolylmethyl, carboxymethyl, 1-carboxyethyl, 1-carboxypropyl or 1-carboxy-3-hydroxypropyl.

9. A compound according to claim 1 which is:

4-[3-(2-benzyloxy-5-fluorophenyl)butyl]benzoic acid;
4-[3-(2-(4-methoxybenzyloxy)phenyl)propyl]benzoic acid;
N-(4-nitrobenzenesulphonyl)-4-[3-(2-benzyloxyphenyl) propyl]-benzenecarboxamide;
4-[3-(2-benzyloxy-5-fluorophenyl)propyl]benzoic acid;
5-[4-(2-benzyloxyphenethyl)phenyl]tetrazole;
4-[2-benzyloxyphenethyl)-3-fluorobenzoic acid;
5-[4-(2-(2-benzyloxyphenyl)ethenyl)phenyl]tetrazole;
4-[3-(2-benzyloxy-5-chlorophenyl)propyl]benzoic acid;
4-[3-(2-(3-chlorobenzyloxy)phenyl)propyl]benzoic acid;
4-[3-(2-benzyloxynaphth-1-yl)propyl]benzoic acid;
4-[3-(2-benzyloxy-5-acetylphenyl)propyl]benzoic acid;
4-[3-(2-benzyloxy-5-nitrophenyl)propyl]benzoic acid;
4-[2-benzyloxy-5-chlorophenethyl]benzoic acid;
5-[4-(5-acetyl-2-benzyloxyphenethyl)phenyl]tetrazole;
5-[4-(2-benzyloxy-5-bromophenethyl)phenyl]tetrazole;
5-[6-(2-benzyloxy-5-bromophenethyl)-1-methyl-1,2-dihydro-2-oxopyridin-3-yl]tetrazole;
4-[3-(2-benzyloxy-5-(1-hydroxyiminoethyl)phenyl)propyl] benzoic acid;
4-[2-benzyloxyphenethyl]-2-hydroxybenzoic acid;
4-[3-(2-benzyloxyphenyl)propyl]-2-hydroxybenzoic acid;
4-[3-(2-benzyloxy-5-methylthiophenyl)propyl]benzoic acid;
2-[2-benzyloxy-5-bromophenethyl]-3,4-dihydro-3-ethyl-4-oxopyrimidin-5-carboxylic acid;
4-[2-(2-benzyloxyphenyl)ethenyl]-3-bromobenzoic acid;
4-[2-(2-benzyloxyphenyl)ethenyl]-3-methoxybenzoic acid;
4-[3-(2-benzyloxy-5-(2-methylpropionyl)phenyl)propyl] benzoic acid;
5-[4-(2-benzyloxy-5-chlorophenethyl)phenyl]tetrazole;
4-(2-benzyloxy-5-bromophenethyl)-2-hydroxybenzoic acid;
4-(2-benzyloxyphenethyl)-3-bromobenzoic acid;
4-[3-(2-benzyloxy-5-(1-(phenyl)hydroxyiminomethyl) phenyl)propyl]-benzoic acid;
4-(2-benzyloxy-5-bromophenylethyl)-2-methoxybenzoic acid;
4-[3-(2-benzyloxy-5-fluorophenyl)propyl]benzoic acid;
N-benzenesulphenyl-4-[3-(2-benzyloxy-5-chlorophenyl) propyl]-benzenecarboxamide;
4-[3-(2-benzyloxy-5-(1-(2-phenylhydrazino)ethyl)phenyl) propyl]benzoic acid;
4-[2-(2-benzyloxy-5-methylthiophenyl)ethenyl]-2-hydroxybenzoic acid;

5-[4-(2-benzyloxyphenethyl)-3-methoxyphenyl]tetrazole;
4-[3-(2-benzyloxyphenyl)propyl]-3-bromobenzoic acid;
5-[4-(2-benzyloxyphenethyl)-3-bromophenyl]tetrazole;
4-[3-(2-benzyloxyphenyl)propyl]-3-cyanobenzoic acid;
5-[4-(3-(2-benzyloxyphenyl)propyl)-3-bromophenyl]tetrazole;
4-(2-benzyloxy-5-methylthiophenethyl)-2-hydroxybenzoic acid;
5-[4-(3-(2-benzyloxyphenyl)propyl)-3-methoxyphenyl]tetrazole;
4-(2-benzyloxy-5-chlorophenethyl)-3-methoxy benzoic acid;
5-[4-(2-benzyloxy-5-chlorophenethyl)-3-methoxyphenyl]tetrazole;
4-(2-benzyloxy-5-methoxyphenethyl)-2-hydroxybenzoic acid; or
4-(2-benzyloxy-5-methylphenethyl)-2-hydroxybenzoic acid; or
a pharmaceutically acceptable salt thereof.

10. A pharmaceutical composition which comprises a compound according to claim 1 and a pharmaceutically acceptable carrier.

11. A method for the treatment of pain in an animal body in need of such treatment which comprises administering to said animal body an effective amount of a compound according claim 1.

* * * * *